United States Patent
Thaxton et al.

(10) Patent No.: US 11,285,106 B2
(45) Date of Patent: Mar. 29, 2022

(54) SYNTHETIC NANOSTRUCTURES INCLUDING NUCLEIC ACIDS AND/OR OTHER ENTITIES

(71) Applicant: Northwestern University, Evanston, IL (US)

(72) Inventors: C. Shad Thaxton, Chicago, IL (US); Chad A. Mirkin, Wilmette, IL (US); Kaylin M. McMahon, Chicago, IL (US); Sushant Tripathy, Evanston, IL (US); Raja Kannan Mutharasan, Chicago, IL (US); David M. Leander, St. Louis, MO (US); Andrea Luthi, Evanston, IL (US)

(73) Assignee: Northwestern University, Evanston, IL (US)

( * ) Notice: Subject to any disclaimer, the term of this patent is extended or adjusted under 35 U.S.C. 154(b) by 408 days.

(21) Appl. No.: 16/384,749

(22) Filed: Apr. 15, 2019

(65) Prior Publication Data
US 2019/0365648 A1 Dec. 5, 2019

Related U.S. Application Data

(60) Continuation of application No. 14/963,881, filed on Dec. 9, 2015, now Pat. No. 10,328,026, which is a continuation of application No. 14/215,569, filed on Mar. 17, 2014, now Pat. No. 9,216,155, which is a division of application No. 13/522,827, filed as application No. PCT/US2011/021753 on Jan. 19, 2011, now abandoned.

(60) Provisional application No. 61/424,904, filed on Dec. 20, 2010, provisional application No. 61/365,987, filed on Jul. 20, 2010, provisional application No. 61/296,373, filed on Jan. 19, 2010.

(51) Int. Cl.
| | |
|---|---|
| *A61K 9/127* | (2006.01) |
| *A61K 31/7088* | (2006.01) |
| *B82Y 5/00* | (2011.01) |
| *C12N 15/87* | (2006.01) |
| *A61K 47/54* | (2017.01) |
| *A61K 47/69* | (2017.01) |
| *A61K 9/51* | (2006.01) |
| *C12N 15/11* | (2006.01) |

(52) U.S. Cl.
CPC ............ *A61K 9/127* (2013.01); *A61K 9/1271* (2013.01); *A61K 9/5115* (2013.01); *A61K 9/5123* (2013.01); *A61K 31/7088* (2013.01); *A61K 47/544* (2017.08); *A61K 47/554* (2017.08); *A61K 47/6917* (2017.08); *A61K 47/6923* (2017.08); *B82Y 5/00* (2013.01); *C12N 15/87* (2013.01); *C12N 15/111* (2013.01); *C12N 2310/113* (2013.01); *C12N 2310/3515* (2013.01); *C12N 2320/32* (2013.01)

(58) Field of Classification Search
CPC ...................................................... A61K 9/127
See application file for complete search history.

(56) References Cited

U.S. PATENT DOCUMENTS

| | | |
|---|---|---|
| 5,472,881 A | 12/1995 | Beebe et al. |
| 5,814,666 A | 9/1998 | Green et al. |
| 5,955,589 A | 9/1999 | Cook et al. |
| 6,274,337 B1 | 8/2001 | Parce et al. |
| 6,361,944 B1 | 3/2002 | Mirkin et al. |
| 6,506,564 B1 | 1/2003 | Mirkin et al. |
| 6,677,153 B2 | 1/2004 | Iversen |
| 7,691,414 B2 | 4/2010 | Sligar et al. |
| 7,951,453 B2 | 5/2011 | Debertret et al. |
| 8,323,686 B2 * | 12/2012 | Mirkin ................. A61K 9/1275 424/450 |
| 8,933,046 B2 | 1/2015 | Machuy et al. |
| 9,216,155 B2 | 12/2015 | Thaxton et al. |
| 9,532,948 B2 | 1/2017 | Mirkin et al. |
| 9,693,957 B2 | 7/2017 | Lin et al. |
| 9,999,673 B2 | 6/2018 | Rajeev et al. |
| 10,078,092 B2 | 9/2018 | Mutharasan et al. |
| 10,328,026 B2 | 6/2019 | Thaxton et al. |

(Continued)

FOREIGN PATENT DOCUMENTS

| | | |
|---|---|---|
| CN | 1474831 A | 2/2004 |
| CN | 102036652 A | 4/2011 |

(Continued)

OTHER PUBLICATIONS

Wolfrum et al. (Nature Biotechnology. Oct. 2007; 25(10): 1149-1157). (Year: 2007).*
Kim et al. (Molecular Pharmaceutics. 2008; 5(4): 622-631). (Year: 2008).*
Thaxton et al. (J. Am. Chem. Soc. 2009; 131: 1384-1385, published on web Jan. 9, 2009) (Year: 2009).*
Akhtar et al. (J Clin Invest. 2007; 117(12): 3623-3632). (Year: 2007).*
Chinese Office Action for CN 200980118614.7 dated Aug. 23, 2011.
Chinese Office Action for CN 200980118614.7 dated Jul. 9, 2012.
International Search Report and Written Opinion for International Application No. PCT/US2009/002540 dated Jul. 22, 2010.

(Continued)

*Primary Examiner* — Scott Long
(74) *Attorney, Agent, or Firm* — Wolf, Greenfield & Sacks, P.C.

(57) ABSTRACT

Articles, compositions, kits, and methods relating to nanostructures, including synthetic nanostructures, are provided. Certain embodiments described herein include structures having a core-shell type arrangement; for instance, a nanostructure core may surrounded by a shell including a material, such as a lipid bilayer, and may include other components such as oligonucleotides. In some embodiments, the structures, when introduced into a subject, can be used to deliver nucleic acids and/or can regulate gene expression. Accordingly, the structures described herein may be used to diagnose, prevent, treat or manage certain diseases or bodily (Continued)

conditions. In some cases, the structures are both a therapeutic agent and a diagnostic agent.

18 Claims, 21 Drawing Sheets

Specification includes a Sequence Listing.

(56) References Cited

U.S. PATENT DOCUMENTS

| | | | |
|---|---|---|---|
| 10,413,565 | B2 | 9/2019 | Plebanek et al. |
| 10,517,927 | B2 | 12/2019 | Braddock et al. |
| 10,568,898 | B2 | 2/2020 | Thaxton et al. |
| 10,967,072 | B2 | 4/2021 | Thaxton et al. |
| 2003/0147966 | A1 | 8/2003 | Franzen et al. |
| 2004/0038891 | A1 | 2/2004 | Bisgaier et al. |
| 2004/0053384 | A1 | 3/2004 | Sligar et al. |
| 2004/0158051 | A1 | 8/2004 | Ozkan et al. |
| 2005/0130167 | A1 | 6/2005 | Bao et al. |
| 2006/0083781 | A1 | 4/2006 | Shastri et al. |
| 2006/0292174 | A1 | 12/2006 | de los Rios et al. |
| 2007/0218501 | A1 | 9/2007 | Fogelman et al. |
| 2007/0243136 | A1 | 10/2007 | Fisher et al. |
| 2007/0249555 | A1 | 10/2007 | Barbaras et al. |
| 2007/0298257 | A1 | 12/2007 | Ludwig et al. |
| 2008/0181928 | A1 | 7/2008 | Hakimi-Mehr et al. |
| 2008/0194463 | A1 | 8/2008 | Weller et al. |
| 2008/0274454 | A1 | 11/2008 | Mirkin et al. |
| 2008/0306016 | A1 | 12/2008 | Mirkin et al. |
| 2008/0311182 | A1 | 12/2008 | Ferrari et al. |
| 2009/0018028 | A1 | 1/2009 | Lindsay et al. |
| 2009/0209629 | A1 | 8/2009 | Mirkin et al. |
| 2009/0317802 | A1 | 12/2009 | Bhatia et al. |
| 2009/0324706 | A1* | 12/2009 | Mirkin ................. A61K 9/1275 424/450 |
| 2010/0003317 | A1 | 1/2010 | Akinc et al. |
| 2010/0136682 | A1 | 6/2010 | Mirkin et al. |
| 2010/0144848 | A1 | 6/2010 | Vogel et al. |
| 2010/0166842 | A1 | 7/2010 | Lu et al. |
| 2010/0184844 | A1 | 7/2010 | Mirkin et al. |
| 2010/0233141 | A1 | 9/2010 | Polach et al. |
| 2010/0233270 | A1 | 9/2010 | Mirkin et al. |
| 2011/0052680 | A1 | 3/2011 | Hendrickson et al. |
| 2011/0059156 | A9 | 3/2011 | Mirkin et al. |
| 2011/0111974 | A1 | 5/2011 | Mirkin et al. |
| 2011/0237435 | A1 | 9/2011 | Ryan |
| 2011/0256224 | A1 | 10/2011 | Sigalov |
| 2012/0149843 | A1 | 6/2012 | Chien et al. |
| 2012/0244230 | A1 | 9/2012 | Mirkin et al. |
| 2013/0034599 | A1 | 2/2013 | Thaxton et al. |
| 2013/0089614 | A1 | 4/2013 | Zhang et al. |
| 2013/0101512 | A1 | 4/2013 | Mirkin et al. |
| 2013/0195759 | A1 | 8/2013 | Mirkin et al. |
| 2013/0196951 | A1 | 8/2013 | Schoenfisch et al. |
| 2013/0252852 | A1 | 9/2013 | Pfeiffer et al. |
| 2013/0295129 | A1 | 11/2013 | Irvine et al. |
| 2014/0005258 | A1 | 1/2014 | Mirkin et al. |
| 2014/0065425 | A1 | 3/2014 | Bogdanov |
| 2014/0134658 | A1 | 5/2014 | Ahrens et al. |
| 2014/0294927 | A1 | 10/2014 | Thaxton et al. |
| 2015/0064255 | A1 | 3/2015 | Thaxton et al. |
| 2015/0086985 | A1 | 3/2015 | Giljohann et al. |
| 2015/0111790 | A1 | 4/2015 | Ategeka et al. |
| 2016/0194642 | A1 | 7/2016 | Gryaznov et al. |
| 2016/0274134 | A1 | 9/2016 | Mutharasan et al. |
| 2016/0310425 | A1 | 10/2016 | Mirkin et al. |
| 2018/0074080 | A1 | 3/2018 | Thaxton et al. |
| 2018/0311176 | A1 | 11/2018 | Ozsolak et al. |
| 2019/0079105 | A1 | 3/2019 | Mutharasan et al. |
| 2019/0365648 | A1 | 12/2019 | Thaxton et al. |
| 2020/0281962 | A1 | 9/2020 | Rink et al. |
| 2020/0330655 | A1 | 10/2020 | Thaxton et al. |
| 2020/0363437 | A1 | 11/2020 | Thaxton et al. |
| 2021/0244826 | A1 | 8/2021 | Thaxton et al. |

FOREIGN PATENT DOCUMENTS

| | | | |
|---|---|---|---|
| EP | 1 889 911 | A2 | 2/2008 |
| EP | 2399608 | A1 | 12/2011 |
| JP | 2011-507807 | A | 3/2011 |
| WO | WO 92/21330 | A1 | 12/1992 |
| WO | WO 93/21528 | A1 | 10/1993 |
| WO | WO 1996/034876 | A1 | 11/1996 |
| WO | WO 1998/004740 | A1 | 2/1998 |
| WO | WO 2000/020645 | A1 | 4/2000 |
| WO | WO 2001/003709 | A1 | 1/2001 |
| WO | WO 2003/008539 | A2 | 1/2003 |
| WO | WO 2006/110350 | A2 | 10/2006 |
| WO | WO 2006/110350 | A3 | 10/2006 |
| WO | WO 2006/128121 | A2 | 11/2006 |
| WO | WO 2006/138145 | A1 | 12/2006 |
| WO | WO 2007/008463 | A2 | 1/2007 |
| WO | WO 2007/089607 | A2 | 8/2007 |
| WO | WO 2007/106683 | A2 | 9/2007 |
| WO | WO 2008/014979 | A2 | 2/2008 |
| WO | WO 2008/106660 | A2 | 9/2008 |
| WO | WO 2008/127789 | A2 | 10/2008 |
| WO | WO 2008/141230 | A1 | 11/2008 |
| WO | WO 2009/012786 | A2 | 1/2009 |
| WO | WO 2009/051451 | A2 | 4/2009 |
| WO | WO 2009/061515 | A1 | 5/2009 |
| WO | WO 2009/073984 | A1 | 6/2009 |
| WO | WO 2009/105260 | A2 | 8/2009 |
| WO | WO 2009/120887 | A2 | 10/2009 |
| WO | WO2009/131704 | * | 10/2009 ............. A61K 9/127 |
| WO | WO 2009/131931 | A1 | 10/2009 |
| WO | WO 2010/017152 | A2 | 2/2010 |
| WO | WO 2010/017154 | A2 | 2/2010 |
| WO | WO 2010/091293 | A1 | 8/2010 |
| WO | WO 2010/120420 | A1 | 10/2010 |
| WO | WO 2011/017456 | A2 | 2/2011 |
| WO | WO 2011/017690 | A2 | 2/2011 |
| WO | WO 2011/053940 | A2 | 5/2011 |
| WO | WO 2011/079290 | A1 | 6/2011 |
| WO | WO 2012/022948 | A1 | 2/2012 |
| WO | WO 2012/068470 | A2 | 5/2012 |
| WO | WO 2014/025795 | A1 | 2/2014 |
| WO | WO 2015/168393 | A1 | 11/2015 |
| WO | WO 2015/195628 | A2 | 12/2015 |
| WO | WO 2017/011662 | A1 | 1/2017 |
| WO | WO 2017/035278 | A1 | 3/2017 |
| WO | WO 2017/193087 | A1 | 11/2017 |
| WO | WO 2018/053368 | A1 | 3/2018 |
| WO | WO 2018/237182 | A1 | 12/2018 |
| WO | WO 2020/154705 | A1 | 7/2020 |
| WO | WO 2020/219833 | A1 | 10/2020 |
| WO | WO 2020/231860 | A1 | 11/2020 |
| WO | WO 2021/055788 | A1 | 3/2021 |

OTHER PUBLICATIONS

International Preliminary Report on Patentability for International Application No. PCT/US2009/002540 dated Nov. 4, 2010.
International Search Report and Written Opinion for International Application No. PCT/US2011/021753 dated Oct. 7, 2011.
International Preliminary Report on Patentability for International Application No. PCT/US2011/021753 dated Aug. 2, 2012.
International Search Report and Written Opinion for International Application No. PCT/US2013/027431 dated Jun. 13, 2013.
International Preliminary Report on Patentability for International Application No. PCT/US2013/027431 dated Sep. 4, 2014.
International Search Report and Written Opinion for International Application No. PCT/US2014/050963 dated Dec. 3, 2014.
International Preliminary Report on Patentability for International Application No. PCT/US2014/050963 dated Feb. 25, 2016.
International Search Report and Written Opinion for International Application No. PCT/US2015/062431 dated Feb. 25, 2016.
International Preliminary Report on Patentability for International Application No. PCT/US2015/062431 dated Jun. 8, 2017.
International Search Report and Written Opinion for International Application No. PCT/US2016/067243 dated Apr. 11, 2017.
International Search Report and Written Opinion for International Application No. PCT/US2017/021293 dated Jun. 19, 2017.

(56) References Cited

OTHER PUBLICATIONS

Agbasi-Porter et al., Transcription inhibition using oligonucleotide-modified gold nanoparticles, Bioconjugate Chem., 17(5):1178-83 (2006).

Aurasense Therapeutics, NIH grant, "Topically-delivered Target Gene Suppression of Immune Activation in Psoriasis—David Giljohann", Accessed on Aug. 2, 2017 from <http://grantome.com/grant/NIH/R41-AR066438-01> Accessible online on Feb. 21, 2016 as verified through Wayback Machine. X Aims 1-3.

Banchelli et al., Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.

Bhattarai et al., "Enhanced Gene and siRNA Delivery by Polycation-Modified Mesoporous Silica Nanoparticles Loaded with Chloroquine," Pharm. Res., 2010, 27, 2556-2568.

Boudreault et al., Nanoscale tools to selectively destroy cancer cells. Chem Commun. May 14, 2008;(18):2118-20. doi: 10.1039/b800528a. Epub Apr. 7, 2008.

Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.

Cheng et al., Interdigitated phospholipid/alkanethiol bilayers assembled on APTMS-supported gold colloid electrodes. Electroanalysis. 2004;16(1-2):127-31. doi: 10.1002/elan.200302929.

Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.

Cho et al., Therapeutic nanoparticles for drug delivery in cancer. Clin Cancer Res. Mar. 1, 2008;14(5):1310-6. doi: 10.1158/1078-0432.CCR-07-1441.

Chromy, B. et al., "Different Apolipoproteins Impact Nanolipoprotein Particle Formation," J. Am. Chem. Soc., 2007, 129 (46), 14348-14354.

Cormode, D.P. et al., "Nanocrystal Core High-Density Lipoproteins: A Multimodality Contrast Agent Platform," Nano Lett., 2008, 8 (11), 3715-3723.

Cutler et al., Polyvalent nucleic acid nanostructures. J Am Chem Soc. Jun. 22, 2011;133(24):9254-7. doi:10.1021/ja203375n. Epub Jun. 1, 2011.

Cutler et al., Polyvalent oligonucleotide iron oxide nanoparticle "click" conjugates. Nano Lett. Apr. 14, 2010;10(4):1477-80. doi: 10.1021/nl100477m.

Cutler et al., Spherical nucleic acids. J Am Chem Soc. Jan. 25, 2012;134(3):1376-91. doi: 10.1021/ja209351u. Epub Jan. 9, 2012.

Daniel et al., Gold nanoparticles: assembly, supramolecular chemistry, quantum-size-related properties, and applications toward biology, catalysis, and nanotechnology. Chem Rev. Jan. 2004;104(1):293-346.

Dave et al., Programmable assembly of DNA-functionalized liposomes by DNA. ACS Nano. Feb. 22, 2011;5(2):1304-12. doi: 10.1021/nn1030093. Epub Jan. 4, 2011.

Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.

Elbakry, A. et al., "Layer-by-Layer Assembled Gold Nanoparticles for siRNA Delivery," Nano Lett., 2009, 9 (5), 2059-2064.

Frias, J. C. et al., "Properties of a Versatile Nanoparticle Platform Contrast Agent to Image and Characterize Atherosclerotic Plaques by Magnetic Resonance Imaging," Nano Lett., 2006, 6 (10), 2220-2224.

Frias, J. C. et al., "Recombinant HDL-Like Nanoparticles: A Specific Contrast Agent for MRI of Atherosclerotic Plaques," J. Am. Chem. Soc., 2004, 126 (50), 16316-16317.

Giljohann et al., Gene regulation with polyvalent siRNA-nanoparticle conjugates. J Am Chem Soc. Feb. 18, 2009;131(6):2072-3.

Giljohann et al., Gold nanoparticles for biology and medicine. Angew Chem Int Ed Engl. Apr. 26, 2010;49(19):3280-94. doi: 10.1002/anie.200904359.

Giljohann et al., Oligonucleotide loading determines cellular uptake of DNA-modified gold nanoparticles. Nano Lett. Dec. 2007;7(12):3818-21. Epub Nov. 13, 2007.

Gissot et al., Nucleoside, nucleotide and oligonucleotide based amphiphiles: a successful marriage of nucleic acids with lipids. Org. Biomol. Chem. 2008;6:1324-33.

Godard et al., Antisense Effects of Cholesterol-Oligodeoxynucleotide Conjugates Associated with Poly(alkylcyanoacrylate) Nanoparticles. Eur. J. Biochem., 1995, 232 (2), 404-410.

Gryaznov, Oligonucleotide n3'-->p5' phosphoramidates and thiophoshoramidates as potential therapeutic agents. Chem Biodivers. Mar. 2010;7(3):477-93. doi: 10.1002/cbdv.200900187. Review.

Han et al., Drug and gene delivery using gold nanoparticles. NanoBiotechnology. Mar. 2007;3(1):40-5.

Hartmann et al., Delineation of a CpG phosphorothioate oligodeoxynucleotide for activating primate immune responses in vitro and in vivo. J Immunol. Feb. 1, 2000;164(3):1617-24.

He et al., Phospholipid-stabilized Au-nanoparticles. Biomacromolecules. May 2005-Jun.;6(3):1224-5.

Houot et al., T-cell modulation combined with intratumoral CpG cures lymphoma in a mouse model without the need for chemotherapy. Blood. Apr. 9, 2009;113(15):3546-52. doi: 10.1182/blood-2008-07-170274. Epub Oct. 21, 2008.

Hurst, S. et al., "Maximizing DNA Loading on a Range of Gold Nanoparticle Sizes," Anal. Chem., 2006, 78 (24), 8313-8318.

Jones, Simultaneous labeling of lipoprotein intracellular trafficking in pigeon monocyte-derived macrophages. Am J Pathol. Mar. 1997;150(3):1113-24.

Kandimalla et al., Secondary structures in CpG oligonucleotides affect immunostimulatory activity. Biochem Biophys Res Commun. Jul. 11, 2003;306(4):948-53.

Kerkmann et al., Immunostimulatory properties of CpG-oligonucleotides are enhanced by the use of protamine nanoparticles. Oligonucleotides. 2006 Winter;16(4):313-22.

Khmelinskaia et al., Effect of anchor positioning on binding and diffusion of elongated 3D DNA nanostructures on lipid membranes. J. Phys. D: Appl. Phys. Apr. 13, 2016;49(19):194001.

Kim et al., "Systemic and Specific Delivery of Small Interfering RNAs to the Liver Mediated by Apolipoprotein A-I," Mol. Ther., 2007, 15 (6), 1145-1152.

Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.

Kong et al., Unique Roles of Gold Nanoparticles in Drug Delivery, Targeting and Imaging Applications. Molecules. Aug. 31, 2017;22(9):1445. doi: 10.3390/molecules22091445.

Leander, Mixed-Monolayer Gold Nanoparticles for Cancer Therapeutics, Nanoscape, 2010, 7 (1), 11-14.

Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.

Lee et al., Silver nanoparticle-oligonucleotide conjugates based on DNA with triple cyclic disulfide moieties, Nano Lett., 7: 2112 (2007).

Lee et al., Imageable antigen-presenting gold nanoparticle vaccines for effective cancer immunotherapy in vivo. Angew Chem Int Ed Engl. Aug. 27, 2012;51(35):8800-5. doi:10.1002/anie.201203193.

Lennox et al., Characterization of modified antisense oligonucleotides in Xenopus laevis embryos. Oligonucleotides. 2006 Spring;16(1):26-42.

Li et al., Nanofabrication by DNA self-assembly. Materials Today. Elsevier Science. May 1, 2009;12(5)24-32.

Li et al., Oligonucleotide-conjugated nanoparticles for targeted drug delivery via scavenger receptors class A: An in vitro assessment for proof-of-concept. Int J Pharm. Oct. 30, 2017;532(1):647-655. doi: 10.1016/j.ijpharm.2017.08.074. Epub Aug. 18, 2017.

Liu, J. et al., Silica Nanoparticle Supported Lipid Bilayers for Gene Delivery, Chem. Commun., 2009, 5100-5102.

(56) References Cited

OTHER PUBLICATIONS

Luthi et al., Nanotechnology for synthetic high-density lipoproteins. Trens Mol Med. Dec. 2010;16(12):553-60. doi: 10.1016/j.molmed.2010.10.006. Epub Nov. 17, 2010.

Lytton-Jean et al., A thermodynamic investigation into the binding properties of DNA functionalized gold nanoparticle probes and molecular fluorophore probes. J Am Chem Soc. Sep. 21, 2005;127(37):12754-5.

Major, M. et al., "Characterisation and Phase Behaviour of Phospholipid Bilayers Adsorbed on Spherical Polysaccharidic Nanoparticles," Biochimica et Biophysica Acta, 1997, 1327, 32-40.

Mangsbo et al., Enhanced tumor eradication by combining CTLA-4 or PD-1 blockade with CpG therapy. J Immunother. Apr. 2010;33(3):225-5. doi: 10.1097/CJI.0b013e3181c01fcb.

Massich et al., Regulating immune response using polyvalent nucleic acid-gold nanoparticle conjugates. Mol Pharm. Nov. 2009-Dec.;6(6):1934-40.

Matsunaga et al., "Biomagnetic Nanoparticle Formation and Application," Supramolecular Science, 1998, 5 (3-4), 391-394.

McBain et al., "Polyethyleneimine Functionalized Iron Oxide Nanoparticles as Agents for DNA Deliver and Transfection," J. Mater. Chem., 2007, 17, 2561-2565.

McKay et al., Characterization of a potent and specific class of antisense oligonucleotide inhibitor of human protein kinase C-alpha expression. J Biol Chem. Jan. 15, 1999;274(3):1715-22.

McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.

Medintz et al., A reactive peptidic linker for self-assembling hybrid quantum dot-DNA bioconjugates. Nano Lett. Jun. 2007;7(6):1741-8. Epub May 26, 2007.

Monia et al., Nuclease resistance and antisense activity of modified oligonucleotides targeted to Ha-ras. J Biol Chem. Jun. 14, 1996;271(24):14533-40.

Mukherjee et al., "Monitoring Cholesterol Organization in Membranes at Low Concentrations Utilizing the Wavelength-Selective Fluorescence Approach," Chemistry and Physics of Lipids, 2005, 134 (1), 79-84.

Nam et al., Nanoparticle-based bio-bar codes for the ultrasensitive detection of proteins. Science. Sep. 26, 2003;301(5641):1884-6.

Niemeyer et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.

Pan et al., Dendrimer-Modified Magnetic Nanoparticles Enhance Efficiency of Gene Delivery System. Cancer Res. 2007;67:8156-8163.

Patel et al., Peptide antisense nanoparticles. Proc Natl Acad Sci U S A. Nov. 11, 2008;105(45):17222-6. doi: 10.1073/pnas.0801609105.

Patil et al., "Evidence for Novel Interdigitated Bilayer Formation of Fatty Acids During Three-Dimensional Self-Assembly on Silver Colloidal Particles," J. Am. Chem. Soc., 1997, 119 (39), 9281-9282.

Patwa et al., Hybrid lipid oligonucleotide conjugates: synthesis, self-assemblies and biomedical applications. Chem Soc Rev. 2011;40:5844-54.

Pfeiffer et al., Bivalent Cholesterol-Based Coupling of Oligonucleotides to Lipid Membrane Assemblies. J. Am. Chem. Soc. 2004;126:10224-10225.

Plant et al., Self-assembled phospholipid/alkanethiol biomimetic bilayers on gold. Langmuir. 1993;9:2764-7.

Pokholenko et al., Lipid oligonucleotide conjugates as responsive nanomaterials for drug delivery. J of Materials Chemistry B. 2013;5329-34.

Qin et al., Significantly improved analytical sensitivity of lateral flow immunoassays by using thermal contrast. Angew Chem Int Ed Engl. Apr. 27, 2012;51(18):4358-61. doi: 10.1002/anie.201200997. Epub Mar. 23, 2012.

Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.

Rosi et al., Oligonucleotide-modified gold nanoparticles for intracellular gene regulation. Science. May 19, 2006;312(5776):1027-30.

Rush et al., Intracellular mRNA regulation with self-assembled locked nucleic acid polymer nanoparticles. J Am Chem Soc. May 28, 2014; 136(21):7615-8. doi: 10.1021/ja503598z. Epub May 14, 2014.

Seferos et al., Nano-flares: probes for transfection and mRNA detection in living cells. J Am Chem Soc. Dec. 19, 2007;129(50):15477-9. Epub Nov. 23, 2007.

Seferos et al., Polyvalent DNA nanoparticle conjugates stabilize nucleic acids. Nano Lett. Jan. 2009;9(1):308-11.

Senarath-Yapa, M.D. et al., "Preparation and Characterization of Poly(lipid)-Coated, Fluorophore-Doped Silica Nanoparticles for Biolabeling and Cellular Imaging," Langmuir, 2007, 23 (25), 12624-12633.

Shahzad et al., Targeted delivery of small interfering RNA using reconstituted high-density lipoprotein nanoparticles. Neoplasia. Apr. 2011;13(4):309-19.

Sita et al., Dual bioluminescence and near-infrared fluorescence monitoring to evaluate spherical nucleic acid nanoconjugate activity in vivo. Proc Natl Acad Sci U S A. Apr. 18, 2017;114(16):4129-4134. doi: 10.1073/pnas.1702736114. Epub Apr. 3, 2017.

Sokolova et al., The use of calcium phosphate nanoparticles encapsulating Toll-like receptor ligands and the antigen hemagglutinin to induce dendritic cell maturation and T cell activation. Biomaterials. Jul. 2010;31(21):5627-33. doi: 10.1016/j.biomaterials.2010.03.067. Epub Apr. 24, 2010.

Sood, 'Good cholesterol' nanoparticles seek and destroy cancer cells. The University of Texas MD Anderson Cancer Center. 2011. Downloaded Apr. 4, 2011. http://healthorbit.ca/newsdetail.asp?opt=1&nltid=164032911.

Switaj et al., CpG immunostimulatory oligodeoxynucleotide 1826 enhances antitumor effect of interleukin 12 gene-modified tumor vaccine in a melanoma model in mice. Clin Cancer Res. Jun. 15, 2004; 10(12 Pt 1):4165-75.

Takahashi, H. et al., "Modification of Gold Nanorods Using Phosphatidylcholine to Reduce Cytotoxicity," Langmuir, 2006, 22 (1), 2-5.

Tang et al., Probing hydroxyl radicals and their imaging in living cells by use of FAM-DNA-Au nanoparticles. Chemistry. Jan. 7, 2008;14(2):522-8.

Thaxton, C.S. et al., Templated Spherical High Density Lipoprotein Nanoparticles, J. Am. Chem. Soc., 2009, 131 (4), 1384-1385.

Thompson et al., Smart lipids for programmable nanomaterials. Nano Lett. Jul. 14, 2010;10(7):2690-3. doi: 10.1021/nl101640k.

Tiwari et al., Functionalized gold nanoparticles and their biomedical applications. Nanomaterials. 2011;1:31-63. doi: 10.3390/nano1010031.

Tripathy et al., High Density Lipoprotein Nanoparticles Deliver RNAi to Endothelial Cells to Inhibit Angiogenesis. Part Part Syst Charact. Nov. 1, 2014;31(11):1141-1150.

United States Securities and Exchange Commission Form 8-K Current Report, Date of Report: Sep. 26, 2017. Exicure, Inc. Dated: Oct. 2, 2017 by David Giljohann Accessed from the internet (Oct. 11, 2018) at https://www.sec.gov/Archives/edgar/data/1698530/000119312517301064/d461080d8k.htm.

Wilton et al. Antisense oligonucleotide-induced exon skipping across the human dystrophin gene transcript. Mol Ther. Jul. 2007;15(7):1288-96. Epub Feb. 6, 2007.

Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.

Xia, T. et al., "Polyethyleneimine Coating Enhances the Cellular Uptake of Mesoporous Silica Nanoparticles and Allows Safe Delivery of siRNA and DNA Constructs," ACSNANO, 2009, 3(10), 3273-3286.

Young et al., Hollow spherical nucleic acids for intracellular gene regulation based upon biocompatible silica shells, Nano Lett., 12:3867 (2012).

(56) References Cited

OTHER PUBLICATIONS

Zhang et al., A general approach to DNA-programmable atom equivalents. Nat Mater. Aug. 2013;12(8):741-6. doi: 10.1038/nmat3647. Epub May 19, 2013.
Zhang et al., A Sensitive Impedance Immunosensor Based on Functionalized Gold Nanoparticle-Protein Composite Films for Probing Apolipoprotein A-I, Talanta, 2007, 71 (2), 874-881.
Zhang et al., Informational liposomes: Complexes derived from cholesteryl-conjugated oligonucleotides and liposomes. Tetrahedron Letters. 1996. 37(35):6243-6.
Zhang et al., Nanopod formation through gold nanoparticle templated and catalyzed crosslinking of polymers bearing pendant propargyl ethers. J Am Chem Soc. Nov. 3, 2010;132(43):15151-3.
Zhang et al., Self-assembled monolayers of terminal alkynes on gold. J Am Chem Soc. Apr. 25, 2007;129(16):4876-7. Epub Mar. 31, 2007.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.
U.S. Appl. No. 16/063,546, filed Jun. 18, 2018, Rink et al.
U.S. Appl. No. 16/083,465, filed Sep. 7, 2018, Thaxton et al.
U.S. Appl. No. 17/221,867, filed Apr. 5, 2021, Thaxton et al.
U.S. Appl. No. 16/917,395, filed Jun. 30, 2020, Thaxton et al.
U.S. Appl. No. 16/625,340, filed Dec. 20, 2019, Thaxton et al.
U.S. Appl. No. 17/425,401, filed Jul. 23, 2021, Henrich et al.
U.S. Appl. No. 17/605,510, filed Oct. 21, 2021, Thaxton et al.
CN 200980118614.7, Aug. 23, 2011, *Chinese Office Action.
CN 200980118614.7, Jul. 9, 2012, *Chinese Office Action.
PCT/US2009/002540, Jul. 22, 2010, *International Search Report and Written Opinion.
PCT/US2009/002540, Nov. 4, 2010, *International Preliminary Report on Patentablility.
PCT/US2011/021753, Oct. 7, 2011, *International Search Report and Written Opinion.
PCT/US2011/021753, Aug. 2, 2012, *International Preliminary Report on Patentability.
PCT/US2013/027431, Jun. 13, 2013, #International Search Report and Written Opinion.
PCT/US2013/027431, Sep. 4, 2014, #International Preliminary Report on Patentability.
PCT/US2014/050963, Dec. 3, 2014, #International Search Report and Written Opinion.
PCT/US2014/050963, Feb. 25, 2016, #International Preliminary Report on Patentability.
PCT/US2015/062431, Feb. 25, 2016, #International Search Report and Written Opinion.
PCT/US2015/062431, Jun. 8, 2017, #International Preliminary Report on Patentability.
PCT/US2016/067243, Apr. 11, 2017, #International Search Report and Written Opinion.
PCT/US2017/021293, Jun. 19, 2017, #International Search Report and Written Opinion.

* cited by examiner

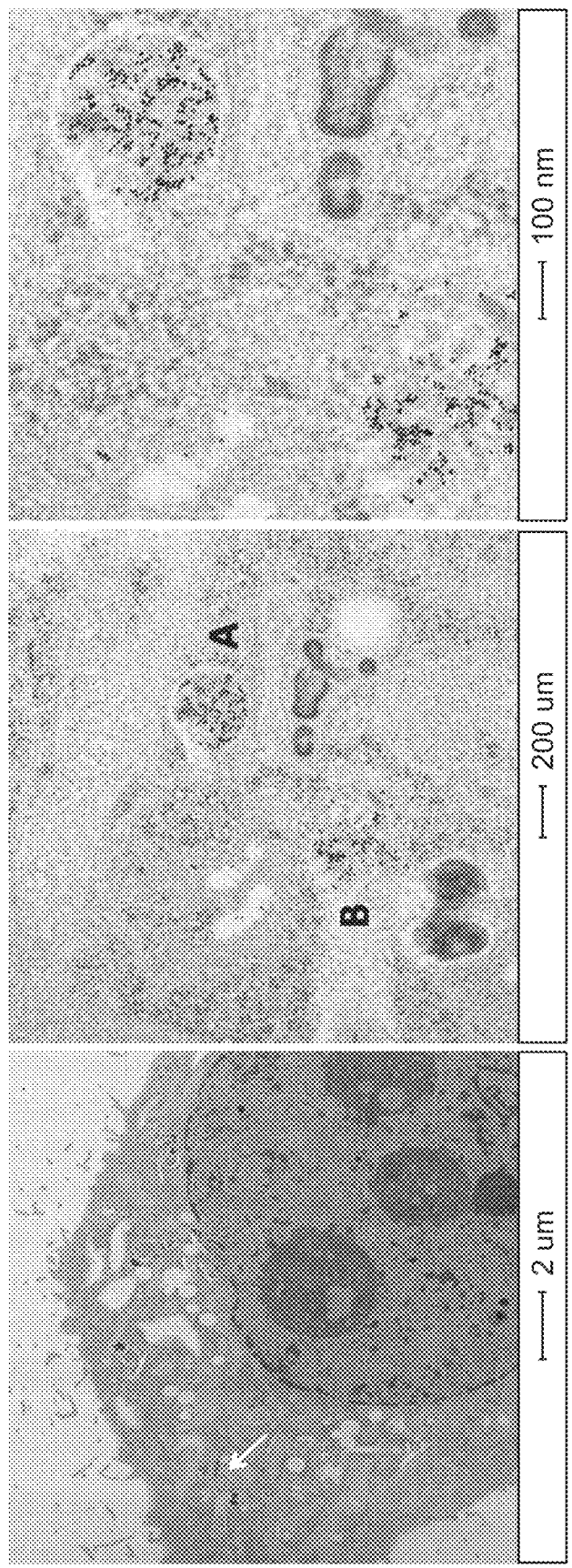

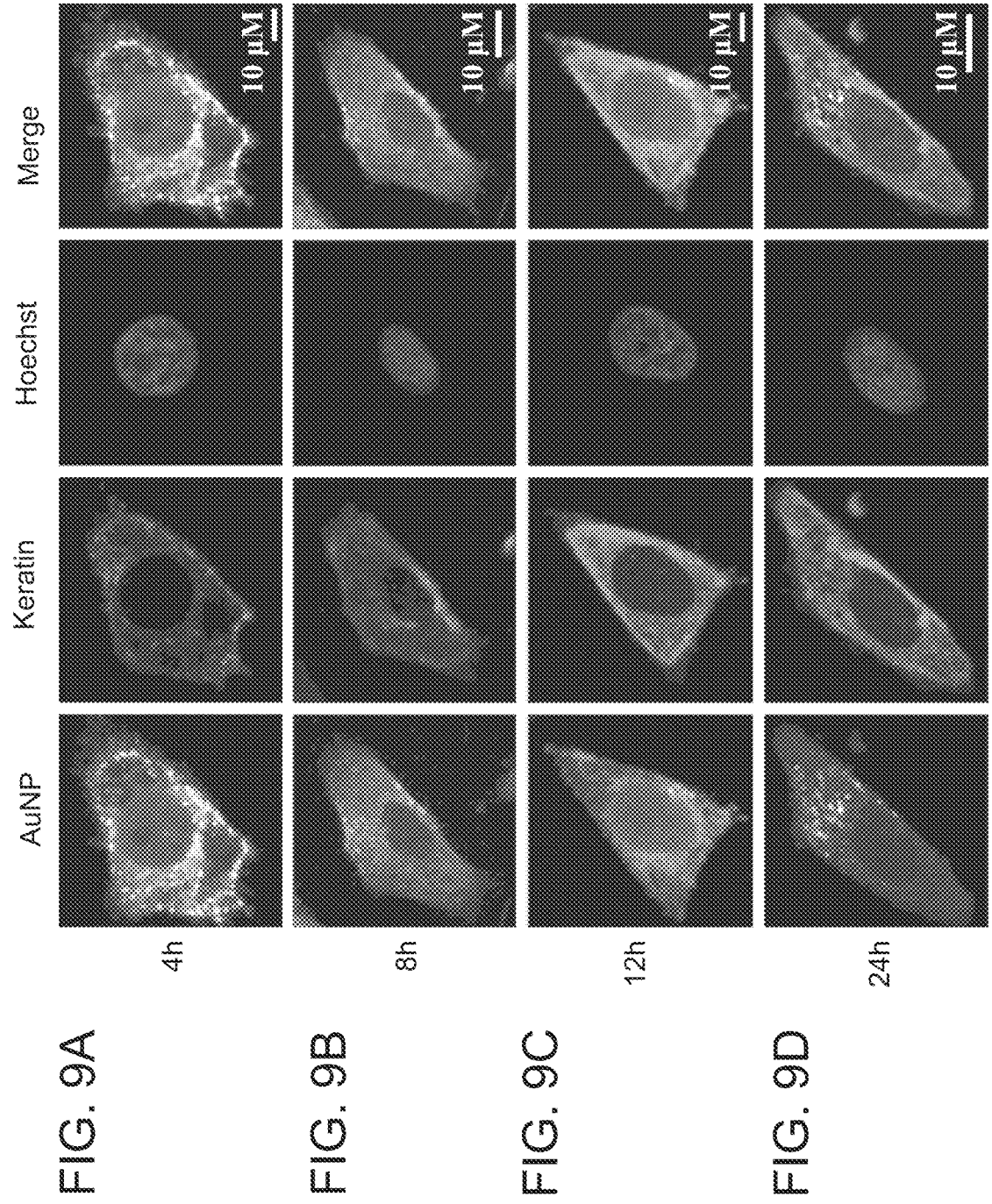

SYNTHETIC NANOSTRUCTURES INCLUDING NUCLEIC ACIDS AND/OR OTHER ENTITIES

RELATED APPLICATIONS

This application is a continuation claiming priority under 35 U.S.C. § 120 of U.S. application Ser. No. 14/963,881 entitled "SYNTHETIC NANOSTRUCTURES INCLUDING NUCLEIC ACIDS AND/OR OTHER ENTITIES" filed on Dec. 9, 2015, now allowed, which is continuation claiming priority under 35 U.S.C. § 120 of U.S. application Ser. No. 14/215,569 entitled "SYNTHETIC NANOSTRUCTURES INCLUDING NUCLEIC ACIDS AND/OR OTHER ENTITIES" filed on Mar. 17, 2014, granted as U.S. Pat. No. 9,216,155, which is a divisional claiming the benefit under 35 U.S.C. § 120 of U.S. application Ser. No. 13/522,827 entitled "SYNTHETIC NANOSTRUCTURES INCLUDING NUCLEIC ACIDS AND/OR OTHER ENTITIES" filed on Oct. 15, 2012, which is a national stage filing under 35 U.S.C. § 371 of international application PCT/US2011/021753, filed Jan. 19, 2011, which was published under PCT Article 21(2) in English, and claims the benefit of priority under 35 U.S.C. § 119(e) of U.S. Provisional Patent Application No. 61/296,373 entitled "MIXED MONOLAYER GOLD NANOPARTICLES FOR CANCER THERAPEUTICS", filed Jan. 19, 2010, and claims the benefit of priority under 35 U.S.C. § 119(e) of U.S. Provisional Patent Application No. 61/365,987, entitled "NANOPARTICLES FOR TREATMENT OF ATHEROSCLEROSIS AND/OR OTHER INDICATIONS", filed Jul. 20, 2010, and claims the benefit of priority under 35 U.S.C. § 119(e) of U.S. Provisional Patent Application No. 61/424,904, entitled "NANOSTRUCTURES INCLUDING NUCLEIC ACIDS AND/OR OTHER ENTITIES", filed Dec. 20, 2010, the contents of each of which are hereby incorporated by reference herein in their entireties.

GOVERNMENT SUPPORT

This invention was made with government support under U54 CA119341 awarded by the National Institutes of Health. The government has certain rights in the invention.

FIELD OF INVENTION

The present invention generally relates to synthetic nanostructures including nucleic acids and/or other entities. The nanostructures may be used for therapeutic and/or diagnostic applications.

BACKGROUND

Nonviral nanoparticle (NP) formulations are being developed to address hurdles inherent to the targeted cellular delivery of short therapeutic nucleic acid (NA) oligonucleotides (e.g. antisense-DNA (AS-DNA), siRNA, and microRNA). Chemical approaches are being employed to endow various synthetic NP platforms with ever-increasing biomimetic capacity to enhance the NPs' ability to overcome interfacial hurdles that arise when cellular biological systems are exposed to synthetic nanostructures. Although there has been progress in the area of nucleic acid delivery and gene regulation, improvements would find application in a number of different fields.

SUMMARY OF THE INVENTION

The present invention generally relates to nanostructures including nucleic acids and/or other entities. The nanostructures may be used for therapeutic and/or diagnostic applications. The nanostructures may find utility for the targeted in vivo delivery of nucleic acid therapeutics for any number of disease processes, including, but not limited to, atherosclerosis, inflammation, and cancer. The subject matter of the present invention involves, in some cases, interrelated products, alternative solutions to a particular problem, and/or a plurality of different uses of one or more systems and/or articles.

Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In another aspect, the present invention is directed to a method of making one or more of the embodiments described herein, for example, structures including nanoparticle-templated biomimetics. In another aspect, the present invention is directed to a method of using one or more of the embodiments described herein. The structures, in some embodiments, may include a nanoparticle-templated biomimetic of high density lipoprotein ("HDL NP"). For example, the structure may have the same or similar shape, size, and/or density as an HDL, and/or the structure may include surface features and/or surface concentrations that resemble endogenous HDLs, for example the presence of Apo A-1 (apolipoprotein) and/or Apo A-II, and/or their components. The structure, in some embodiments, may include phospholipids that resemble those found in endogenous HDLs. In some embodiments, the structure may include a nanostructure core formed of gold; it should be understood, however, that other nanostructure cores and materials can be used as templates to form biomimetic structures in other embodiments.

One aspect of the invention is generally directed to the fabrication, directed tailoring, and in vitro characterization of biomimetic nanostructures which naturally interface with biological systems to deliver nucleic acids. High density lipoproteins (HDL) are naturally circulating human nanostructures with a multitude of beneficial functions. HDLs naturally target specific cell types including endothelial cells, macrophages, and hepatocytes. Using a bottom-up synthetic approach, structures with similar size, shape, and/or surface chemistry to natural mature spherical HDLs may be prepared, as discussed herein, to form structures such as HDL NPs. In some embodiments, the HDL NPs function comparably to their natural counterparts in biological systems to efflux and transport cholesterol. Accordingly, in one set of embodiments, structures such as HDL NPs may be used to assess how biomimicry may be used to successfully integrate functional hybrid nucleic acid-HDL NPs (NA-HDL NPs) into biological systems for nucleic acid delivery.

One aspect of the invention is generally directed to spherical NP-templated HDL biomimetic structures. The binding constant of these structures to cholesterol may be, for example, less than the concentration of total cholesterol in vivo. In some embodiments, the binding constant of these structures to cholesterol may be less than about $K_d=10$ mM. These structures may be engineered to mimic endogenous spherical HDLs. For example, in some embodiments, the structures have a binding constant to cholesterol (or another lipid such as a triglyeride) that is substantially similar to that of endogenous HDL. The surface components of the HDL NP structures, in one set of embodiments, includes those of natural HDL. For example, 2-3 copies of Apo A-1 may be embedded within a layer of NP-adsorbed phospholipids, in one embodiment. The HDL NP structures may have any suitable size, e.g., as described herein. In some embodiments, the HDL NPs can enhance reverse cholesterol transport from cells, such as both murine (J774) and human (THP-1) macrophages grown in culture. Furthermore, a portion of the HDL NPs may be taken up by the cells where they have significant cytoplasmic localization. The structures also include one or more different nucleic acids in some embodiments.

In some embodiments, the structures are modified to include more than one functionality. For example, the structures may be surface-functionalized with thiol end-modified oligonucleotides (i.e. DNA, RNA, siRNA, mRNA, etc.). Structures may also be surface functionalized with thiol-modified oligos able to regulate gene expression. These structures may have increased affinity for complementary nucleic acids compared to unmodified oligonucleotides, reduced susceptibility to nuclease degradation, have greater than 80%, 85%, 90%, 95%, 97%, or 99% cellular uptake, and/or exhibit little or no toxicity. The surface density of bound oligonucleotides to the structures may also be controlled, e.g., to show gene knockdown. Oligonucleotides such as DNA, RNA, or siRNA may be attached to a nanostructure core using techniques such as electrostatic adsorption or chemisorption techniques, for example, Au—SH conjugation chemistry.

One set of embodiments is generally directed to certain nanomaterial structures capable of addressing macrophages and hepatocytes for unique and highly potent dual activity. Thus, the structures may function in both cell types. Design of such structures may involve, for example, balancing the surface coverage of siRNA so as to not, potentially, decrease the capacity for the structure to mediate reverse cholesterol efflux and vice versa.

In one set of embodiments, a series of structures are provided. In one embodiment, a structure comprises a nanostructure core, a shell comprising a lipid surrounding and attached to the nanostructure core, and an oligonucleotide adapted to regulate gene expression associated with at least a portion of the shell. The structure may be adapted to sequester cholesterol.

In another embodiment, a structure comprises a nanostructure core, a hydrophobic shell surrounding the nanostructure core, and an oligonucleotide adapted to regulate gene expression associated with at least a portion of the shell. The structure may be adapted to sequester cholesterol.

In another embodiment, a structure comprises a nanostructure core, and a cholesterol-modified oligonucleotide associated with the nanostructure core.

In another embodiment, a nanostructure comprising an oligonucleotide adapted to regulate gene expression, a lipid, and an apolipoprotein.

In another embodiment, a nanostructure comprises an oligonucleotide adapted to regulate gene expression and apolipoprotein A1.

In some instances, a method includes delivering a structure described herein to a subject or a biological sample, and regulating gene expression in the subject or biological sample.

In some embodiments, a pharmaceutical composition is provided. The composition may include a structure described herein and one or more pharmaceutically acceptable carriers, additives, and/or diluents.

In some embodiments, a kit for diagnosing, preventing, treating or managing a disease or bodily condition is provided. The kit may include a composition comprising a plurality of structures described herein, and instructions for use of the composition for diagnosing, preventing, treating or managing a disease or bodily condition.

In certain embodiments, the structures described herein are single entities that can be used as both a therapeutic and a diagnostic agent.

In another set of embodiments, a series of methods are provided. In one embodiment, a method for diagnosing, preventing, treating or managing a disease or bodily condition. The methods involves administering to a subject a therapeutically-effective amount of a composition comprising a structure described herein, e.g., a structure comprising a nanostructure core comprising an inorganic material and a shell surrounding and attached to the nanostructure core. The structure may be adapted to sequester cholesterol (or other lipids or molecules in certain embodiments). The method may include allowing the structure to sequester cholesterol, e.g., at least 2, at least 3, at least 5, 20, or 50 molecules of cholesterol. The cholesterol may be, for example, esterified cholesterol or free cholesterol. In other embodiments, a method involves allowing the structure to sequester molecules of a particular type or composition, e.g., at least 5, 20, or 50 molecules of a particular type or composition. The structure may be adapted to regulate gene expression in sample or a patient.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 7A-7C are electron micrographs showing murine J774 cells transected with structures described herein according to one set of embodiments;

FIGS. 9A-9D are fluorescent confocal microscopy images showing cellular distribution of structures described herein in PC3 cells according to one set of embodiments;

DETAILED DESCRIPTION

Figure 1:
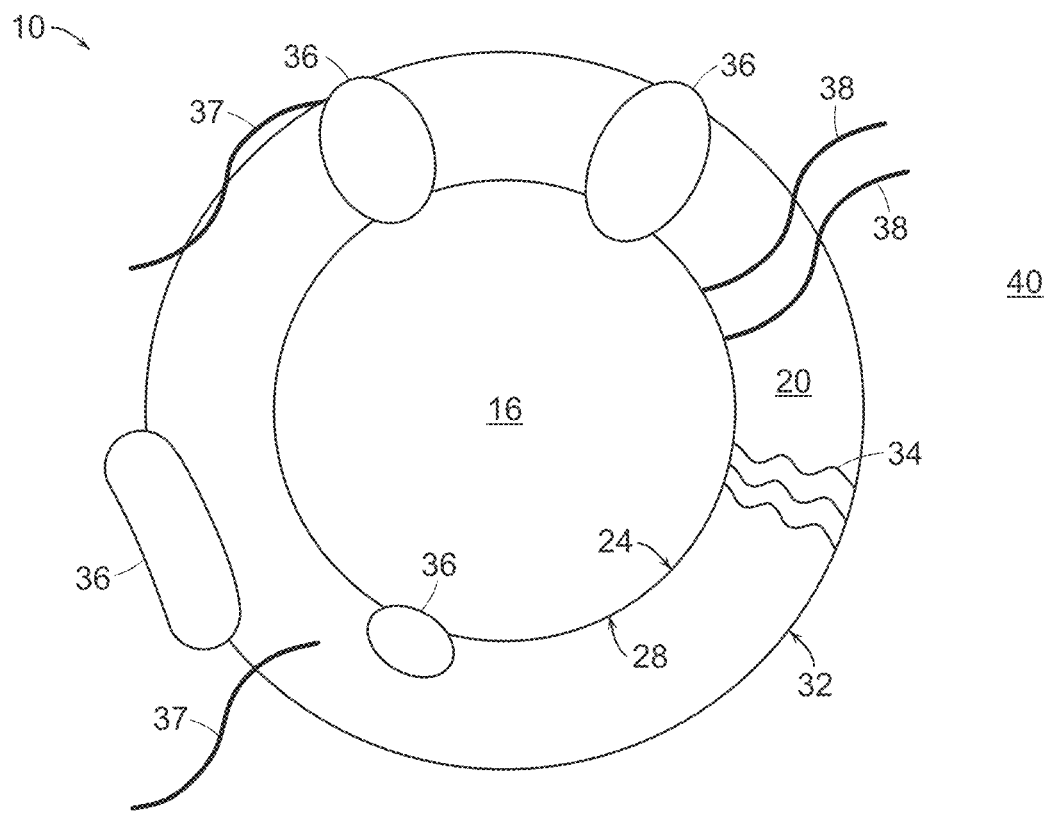
FIG. 1 shows an example of a structure that can be used to deliver nucleic acids and/or other entities according to one set of embodiments.

Articles, compositions, kits, and methods relating to nanostructures, including synthetic nanostructures, are provided. Certain embodiments described herein include structures having a core-shell type arrangement; for instance, a nanostructure core may be surrounded by a shell including a material, such as a lipid bilayer, and may include other components such as oligonucleotides. In some embodiments, the structures, when introduced into a subject, can be used to deliver nucleic acids and/or can regulate gene expression. Accordingly, the structures described herein may be used to diagnose, prevent, treat or manage certain diseases or bodily conditions. In some cases, the structures are both a therapeutic agent and a diagnostic agent.

Seamless integration of nano-biomaterials into biological systems is important for non-viral delivery of nucleic acids. Fabrication of such materials is important in order to fully realize the potential of nucleic acid-based therapies. One aspect of the invention combines a biomimetic nanostructure platform with rational nucleic acid chemistry to synthesize gene-regulating biomaterials. In some embodiments, hybrid nucleic acid-biomimetic structures can be fabricated to successfully navigate the bio-nano interface for targeted and chemically triggered release of regulatory nucleic acids. Anchoring the platform, in one set of embodiments, is a synthetic nanoparticle-templated structure, such as a nanoparticle-templated biomimetic of high density lipoprotein ("HDL NP").

Lipoproteins circulate in the human body and transport hydrophobic molecules (e.g., cholesterol). HDLs have myriad of beneficial physiologic functions including, most notably, the prevention of atherosclerotic cardiovascular disease. Functionally, HDLs naturally target specific cell types (e.g., endothelial cells, macrophages, hepatocytes), are internalized by them, may transfer cholesterol, and are then re-introduced into the circulation. In some embodiments, by using a nanoparticle scaffold as a nanostructure core, the surface protein and lipid components of naturally occurring mature spherical HDL can be assembled. From the standpoint of size, shape, and surface chemistry, the resultant HDL structure may be a mimic of natural HDL. At the core may be a nanoparticle, such as an inorganic nanoparticle (e.g., an AuNP) with potential for biomolecule attachment, such as nucleic acids (e.g., oligonucleotides). The inorganic nanoparticle can be optionally removed to produce a hollow or partially-hollow core in some embodiments.

Although much of the description herein refers to gold nanoparticles (e.g., as use as templates or nanostructure cores), it should be understood that this is by way of example only, and that other structures and materials can be used as templates or nanostructure cores.

In one set of embodiments, synthetic methods for attaching nucleic acids to the surface of nanoparticles (e.g., HDL NPs) are described. Solid phase nucleic acid synthesis may be employed to produce a suite of DNA or RNA oligonucleotides end-modified with functional groups, such as cholesterol and alkyl-thiols, for attachment to nanostructure cores. Systematic tailoring of a nanostructure core with oligonucleotides can be used to obtain control over surface chemical composition. It is believed that the surface chemistry at least partially controls certain bio-nano interfacial interactions.

In another set of embodiments, solid-phase DNA chemistry is used to tailor synthetic oligonucleotides for DNA-nanoparticle (e.g., HDL NP) attachment. For instance, nucleic acid release from the resulting structure may be useful in certain applications. In yet another set of embodiments, the present invention is directed to the gene regulating capacity of the nucleic acid-modified nanostructures in cell culture. In relatively high throughput, the function of such structures can be assessed in a model system to show structure-function relationships. Importantly, the functional impact that deviation from biomimicry imparts may be inferred by surface chemistry (e.g., nucleic acid release mechanism), and can be directly tested to derive a mechanism for optimal bio-integration of a hybrid DNA-HDL NPs.

Specifically, in some embodiments, the present invention is directed to the de novo synthesis of biomimetic HDL nanostructures (HDL NPs), and an evaluation of their ability to deliver targeted gene regulatory oligonucleotides (e.g., cholesterylated oligonucleotides) to the cell cytoplasm. Cancer cells are dependent upon cholesterol delivery by HDL in order to maintain cell membrane biosynthesis and integrity. Thus, a cellular model of androgen insensitive prostate cancer (PC3) was employed for these studies. Data demonstrate that HDL AuNPs with surface-adsorbed cholesterylated antisense DNA (chol-DNA-HDL AuNPs) effectively deliver targeted chol-DNA to the cell cytoplasm, avoid endosomal sequestration, and regulate a model RNA target. The bottom-up synthesis of chol-DNA-HDL AuNPs provides a biomimetic platform for effective cellular NA delivery.

In another set of embodiments, the present invention is generally directed to therapeutic agents for the treatment of atherosclerosis and other indications. The therapeutic agent, in one set of embodiments, targets cells such as macrophages (cholesterol uptake and inflammation) and hepatocytes (production of cholesterol-rich low density lipoprotein (LDL)). Certain embodiments are directed to hybrid nanoparticle-based high density lipoprotein mimetic structures (e.g., HDL NPs). The agent may be used as a cholesterol scavenger (targeting macrophages) and/or as a gene-regulating therapeutic (targeting hepatocytes). In some embodiments, the surface of the HDL NPs may be tailored with nucleic acids, for example, siRNA (e.g., to regulate targeted gene expression in hepatocytes). In addition to mimicking the activity of natural HDL with regard to enhancing reverse cholesterol transport, such structures may reduce the production of low density lipoprotein (LDL) in hepatocytes through HDL NP mediated delivery of siRNA targeting the production of apolipoprotein B-100 (Apo B-100), the main structural protein of LDL.

Current approaches to therapeutic gene regulation with oligonucleotide (e.g., DNA or siRNA) functionalized AuNPs demonstrate that the nanoparticles are taken up by cells through energy-dependent endocytosis. The consequence of this process is that many of the nanoparticles may be trapped in endosomes and do not maximally concentrate in the cytoplasm. For therapeutic approaches that require conjugate nanostructures to interact with targeted and pathologically up-regulated intracellular mRNA targets, for example, this can serve to limit therapeutic efficacy. As such, one problem addressed by the structures described herein is the sub-cellular localization of the structures. The structures may be used to deliver nucleic acids to the cytoplasm within cells to achieve high gene regulating capacity.

Previous research using phospholipid vesicles, or liposomes, have shown that phospholipids are effective drug delivery agents. In some cases, liposomes are able to permeate through cell membranes. However, studies have also shown that these phospholipid particles (about 100 nm in diameter) pass through the cell membrane generating temporary holes in the cell membrane, which can be cytotoxic. In some embodiments by using structures described herein, this cytotoxicity may be reduced or avoided. These structures may, in some cases, permeate the cell membrane and avoid endosomal sequestration. In some embodiments in which the structures include both nucleic acids and lipids, interactions with cells can be tailored by optimizing the nucleic acid:lipid ratio of the structures and by rationally tailoring the surface chemistry of the structures.

Although much of the description herein refers to structures acting as biomimetics of high density lipoprotein, the articles and methods described herein may be useful for forming mimetics of other entities, including naturally-occurring entities, that may provide some therapeutic, diagnostic, and/or other beneficial effect. Structures that mimic naturally-occurring entities may be used to target specific cell types to treat or diagnose certain indications. Some such biomimetic structures may include nucleic acids, and may be used for nucleic acid delivery, tailored nucleic acid release, and/or can be used to regulate gene expression in the target.

The illustrative embodiment of FIG. 1 includes a structure 10 having a core 16 and a shell 20 surrounding the core. In embodiments in which the core is a nanostructure, the core includes a surface 24 to which one or more components can be optionally attached. For instance, in some cases, core 16 is a nanostructure surrounded by shell 20, which includes an inner surface 28 and an outer surface 32. The shell may include one or more components 34, such as a plurality of lipids, which may optionally associate with one another and/or with surface 24 of the core. Structure 10 may optionally include one or more components 36, such as a protein or other entity, and optionally one or more nucleic acids 37 and 38 (e.g., oligonucleotides), which may be used for nucleic acid delivery and/or to regulate gene expression in a sample or patient in some embodiments. As shown illustratively in FIG. 1, nucleic acid 37 may be adsorbed (e.g., physisorbed) to a portion of the shell and nucleic acid 38 may be covalently or near-covalently bonded to surface 24 of the shell.

Components 34 (e.g., lipids) may be associated with the core by being covalently attached to the core, physisorbed, chemisorbed, or attached to the core through ionic interactions, hydrophobic and/or hydrophilic interactions, electrostatic interactions, van der Waals interactions, or combinations thereof. In one particular embodiment, the core includes a gold nanostructure and the shell is attached to the core through a gold-thiol bond. Optionally, components 34 can be crosslinked to one another. Crosslinking of components of a shell can, for example, allow the control of transport of species into the shell, or between an area exterior to the shell and an area interior of the shell. For example, relatively high amounts of crosslinking may allow certain small, but not large, molecules to pass into or through the shell, whereas relatively low or no crosslinking can allow larger molecules to pass into or through the shell. Additionally, the components forming the shell may be in the form of a monolayer or a multilayer, which can also facilitate or impede the transport or sequestering of molecules. In one exemplary embodiment, shell 20 includes a lipid bilayer that is arranged to sequester cholesterol.

It should be understood that a shell which surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. As described herein, the shell may include one layer of material (e.g., a monolayer), or multilayers of materials in some embodiments.

Structure 10 may also include one or more components 36 such as proteins, nucleic acids, and bioactive agents which may optionally impart specificity to the structure. One or more components 36 may be associated with the core, the shell, or both; e.g., they may be associated with surface 24 of the core, inner surface 28 of the shell, outer surface 32 of the shell, and/or embedded in the shell. For example, one or more components 36 may be associated with the core, the shell, or both through covalent bonds, physisorption, chemisorption, or attached through ionic interactions, hydrophobic and/or hydrophilic interactions, electrostatic interactions, van der Waals interactions, or combinations thereof. In one particular embodiment, shell 20 is in the form of a lipoprotein assembly or structure which includes both proteins and lipids that are covalently or non-covalently bound to one another. For example, the shell may be in the form of an apolipoprotein assembly that serves as an enzyme co-factor, receptor ligand, and/or lipid transfer carrier that regulates the uptake of lipids. As described herein, the components of structure 10 may be chosen such that the surface of the structure mimics the general surface composition of HDL, LDL, or other structures, and may be used to sequester cholesterol or other structures in some embodiments.

In one set of embodiments, the structures includes one or more nucleic acid 37 and/or 38 (e.g., an oligonucleotide) that may be adapted and arranged to regulate gene expression in a sample or subject, as described in more detail below.

It should be understood that components and configurations other than those described herein may be suitable for certain structures and compositions, and that not all of the components shown in FIG. 1 are necessarily present in some embodiments.

Figure 2A:
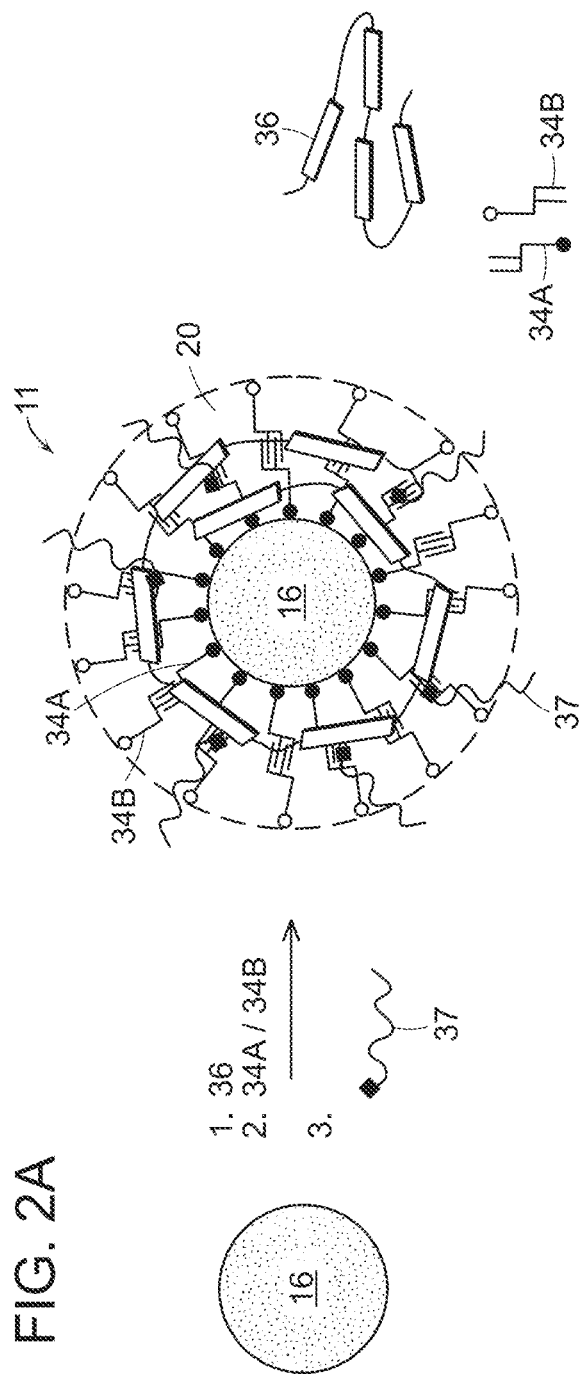
FIGS. 2A and 2B show methods for fabricating various structures that can be used to deliver nucleic acids and/or other entities according to embodiments described herein.
Figure 2B:
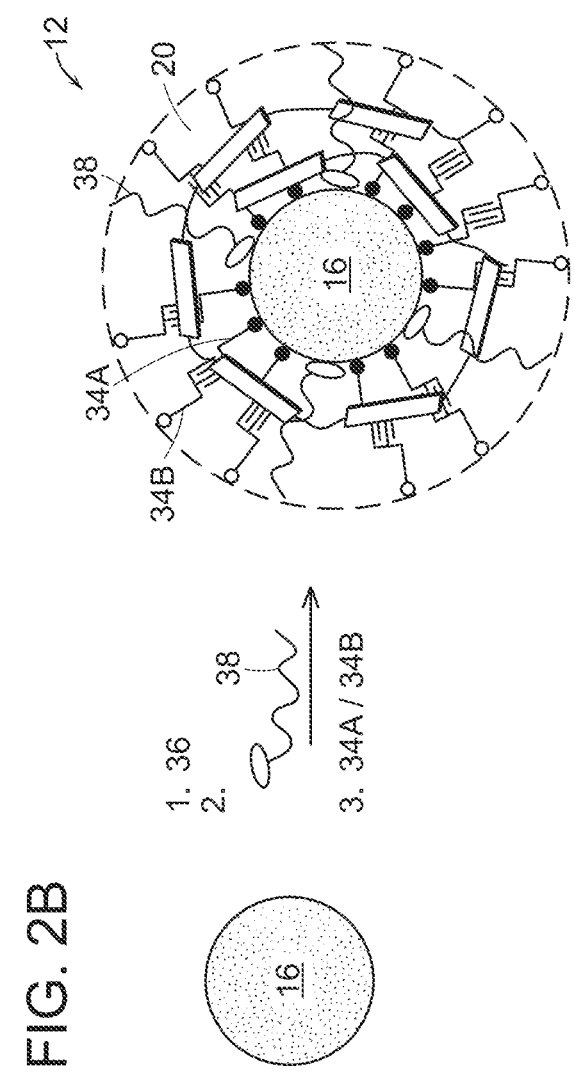

FIGS. 2A and 2B show general approaches for fabricating certain structures described herein. The structures may be used, in some embodiments, to both sequester cholesterol and to deliver nucleic acids and/or to regulate gene expression in a sample or patient. Specifically, FIG. 2A shows a structure 11 that includes a shell 20 and adsorption (e.g., physisorption) of nucleic acids 37 (e.g., oligonucleotides) onto a portion of the shell. The nucleic acid may be adsorbed to an inner portion, outer portion, interior portion of the shell and/or combinations thereof. In some embodiments, nucleic acid 37 is an oligonucleotide adapted to regulate gene expression in a sample or patient.

As shown illustratively in FIG. 2A, structure 11 may include a core 16 substantially surrounded by shell 20. The shell may include a first layer formed of components 34A and a second layer formed of components 34B. In some embodiments, components 34A and/or 34B are lipids, such as phospholipids or other entities described herein. In other embodiments, components 34A and/or 34B are components other than lipids, as described in more detail below. Structure 11 also includes one or more components 36 (e.g., a protein such as an apolipoprotein) associated with the shell. In some embodiments, components 36 are first introduced to core 16, which may be a nanostructure core, followed by components 34A and 34B which form the shell of structure 11. Component 36 may first associate with the surface of the core (e.g., by absorption or by other interactions), and in some cases, may associate with a portion, but not all of, the surface of the core. The addition of components 34A and/or 34B may displace portions of component 36 from the surface of the core, and/or may associate with portions of the core surface where portions of component 36 are not present. Structure 11 may be formed by the addition of one or more nucleic acids 37, which may associate with an outer component 34B of the shell, with an inner component 34A of the shell, between the inner and outer components, or combinations thereof.

FIG. 2B shows a method for forming a structure 12 that includes one or more nucleic acids 38 (e.g., oligonucleotides) that are covalently or near-covalently attached to a surface of a core. The nucleic acid may be attached to the surface of the core directly, or via an intervening layer (e.g., a passivating layer). In some embodiments, nucleic acid 38 is an oligonucleotide adapted to regulate gene expression in a sample or patient. A method of fabricating structure 12 may include, for example, introducing one or more components 36 (e.g., a protein such as an apolipoprotein) to a core 16. Component 36 may, in some embodiments, associate with a portion, but not all of the surface of the core. The resulting entity may then be subjected to a nucleic acid 38 that is end-modified with a functional group that allows it to associate with the surface of the core. The resulting entity may then be subjected to components 34A and/or 34B, which, in some embodiments, may displace at least a portion of component 36 from the surface of the core, and/or may associate with portions of the core surface where portions of component 36 are not present.

Figure 3:
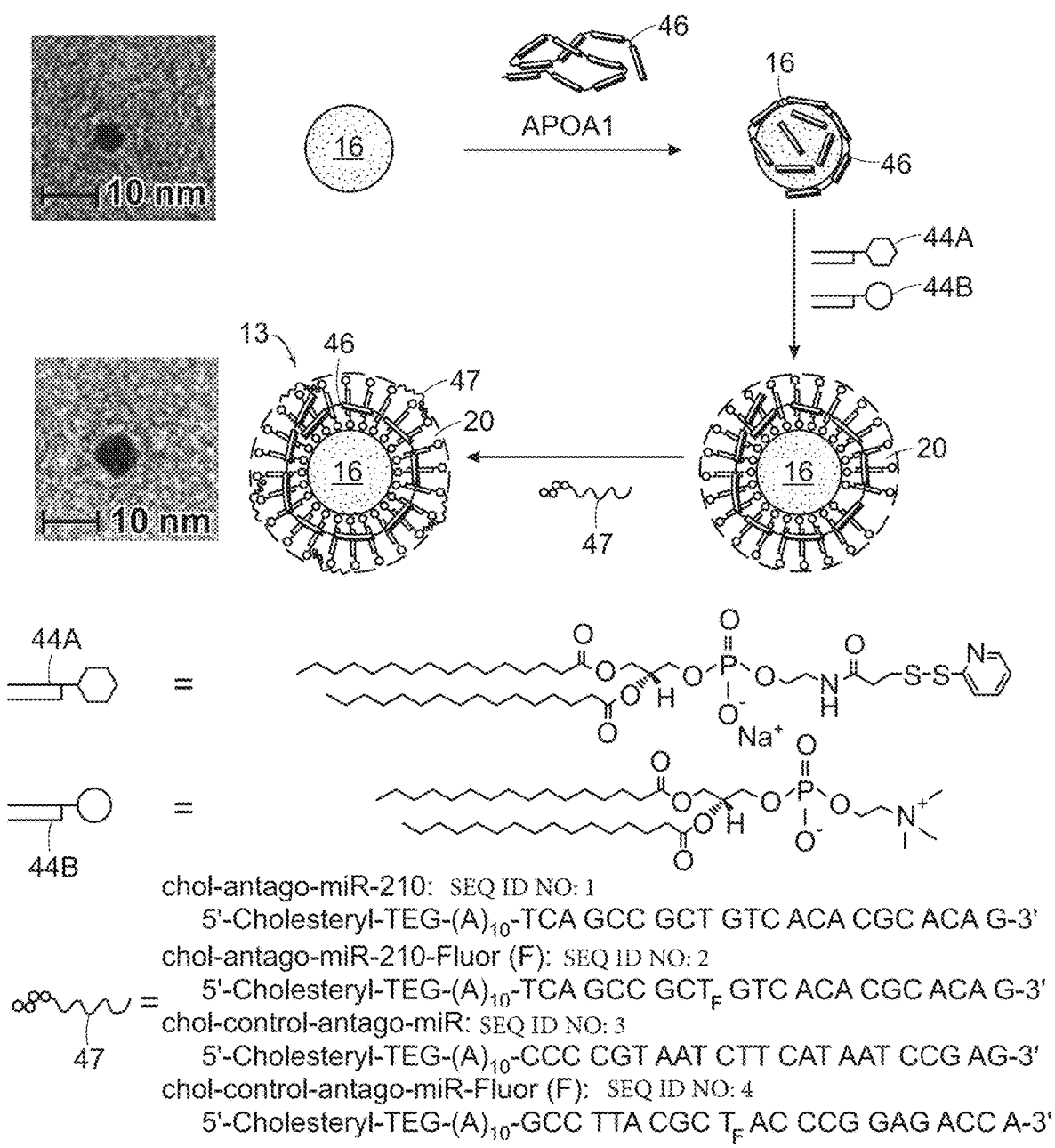
FIG. 3 shows a method for fabricating structures including one or more apolipoproteins and one or more oligonucleotides according to one set of embodiments; 47 lists SEQ ID NOS: 1 through 4 from top to bottom.

FIG. 3 shows a method for forming structures 13 which includes a core 16 surrounded by a shell 20 that includes a lipid bilayer and a protein 46, such as apolipoprotein A1, embedded in the lipid bilayer. Structure 13 may be a biomimetic of endogenous high density lipoprotein (e.g., in terms of shape, size and surface chemistry) in some embodiments. Specific examples of components that can be used to form the lipid bilayer include phospholipids 44A and 44B. One or more oligonucleotides 47 (SEQ ID NOS: 1 through 4 from top to bottom), which may be used to regulate gene expression in a sample or patient, can be absorbed onto a portion of the shell. Although specific components 46 (e.g., APO-A1), 44A and 44B (e.g., phospholipids), and 47 (e.g., oligonucleotides; SEQ ID NOS: 1 through 4 from top to bottom) are shown, other components can be used in other embodiments. Examples of such components are provided in more detail herein.

It should be understood that compositions and methods described herein for treating a sample or patient, especially those for delivering nucleic acids and/or for regulating gene expression, may involve the use of any suitable structure or combination of structures, whether the nucleic acids are adsorbed onto a portion of the structure or covalently/near-covalently attached to a portion of the structure. In certain embodiments, nucleic acids adsorbed to a surface of the structure core, e.g., regardless of the binding constant, are more likely to passively diffuse or exchange from the surface of the structure compared to embodiments in which the nucleic acid is end-modified with suitable groups for covalent or near-covalent coupling to a surface of the structure. As such, in some embodiments, methods involving covalent or near-covalent attachment of nucleic acids may allow for the particle surface chemistry to be more easily controlled. Furthermore, in some cases, the addition of structures having adsorbed nucleic acids into serum-containing matrices (cell culture or blood) may result in transfer of the adsorbed nucleic acid from the structure to other serum lipoproteins or albumin. Covalent or near covalent coupling of the nucleic acid to a surface of the structure may, in some embodiments, provide for a more stable structures with regard to nucleic acid retention. In other embodiments where it is desirable to release nucleic acids from the structure to its surrounding environment, structures including adsorbed nucleic acids may be used.

Figure 4:
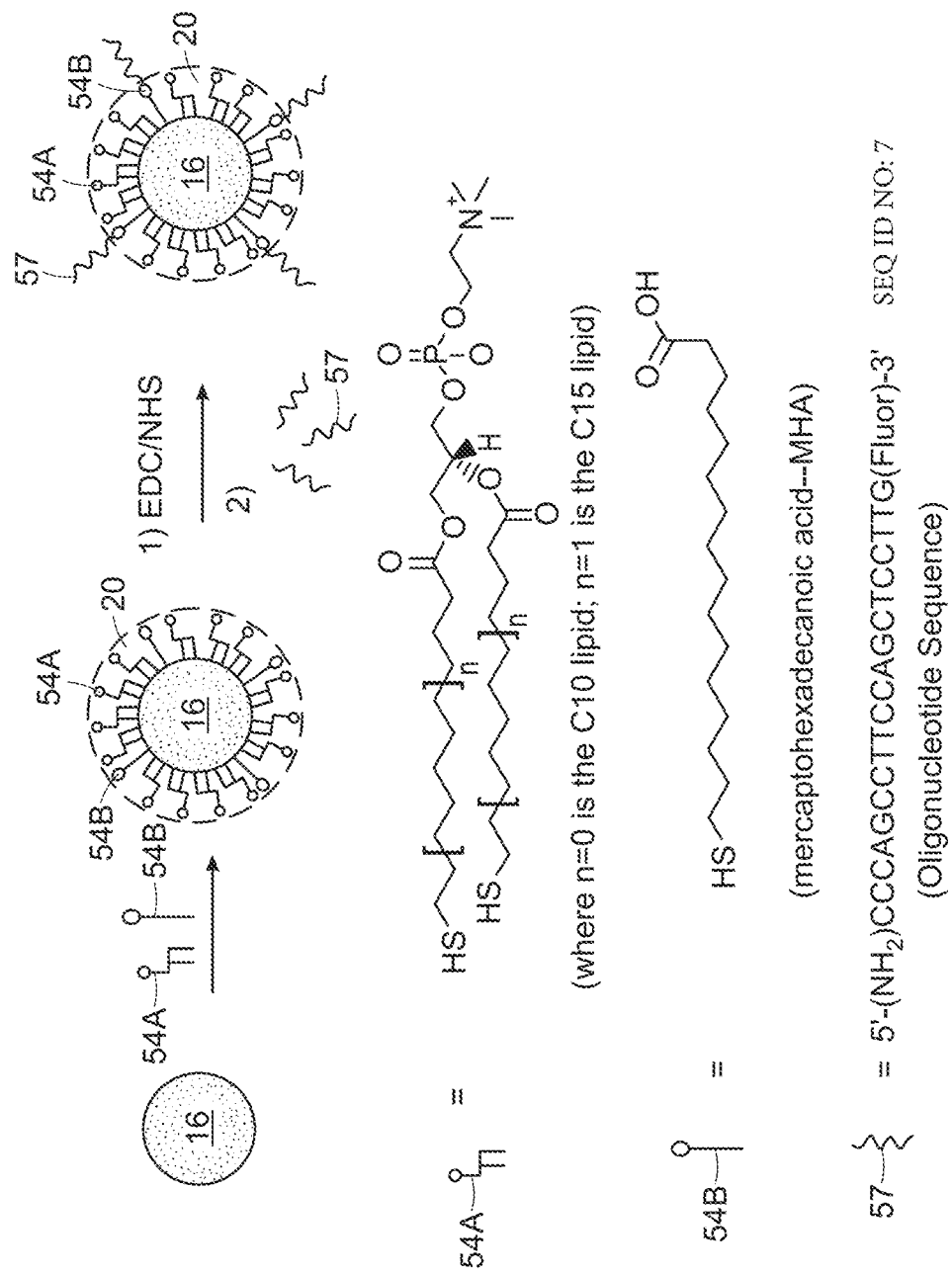
FIG. 4 shows a method for fabricating structures including different components that form a shell of the structure according to one set of embodiments; 57 is SEQ ID NO: 7)

FIG. 4 shows a method for fabricating structures having a mixed layer of components. Shell 20 includes components 54A and 54B which form a single layer (e.g., a monolayer) on the surface of core 16. Examples of specific chemical compounds that can be used as components 54A and 54B are shown in the figure. As shown illustratively in FIG. 4, component 54A may be a phospholipid that imparts hydrophobicity to the outer surface of the core. Such components may lie adjacent components 54B, which may include a functional group that can allow attachment of one or more bioactive agents such as a nucleic acid 57 (e.g., an oligonucleotide such as the one shown specifically in the figure, SEQ ID NO: 7). Although specific chemical compounds are shown in the figure, it should be understood that this is by way of example only, and that other chemical compounds can be used as components 54A, 54B, and 57 in other embodiments.

A core, such as core 16 shown in FIGS. 1-4 (e.g., a nanostructure core or a core that is at least partially hollow), may have any suitable shape and/or size. For instance, the core may be substantially spherical, non-spherical, oval, rod-shaped, pyramidal, cube-like, disk-shaped, wire-like, or irregularly shaped. The core may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, less than or equal to about 10 nm, or less than or equal to about 5 nm. In some cases, the core has an aspect ratio of greater than about 1:1, greater than 3:1, or greater than 5:1. In other cases, the core has an aspect ratio of less than about 10:1, less than 5:1, or less than 3:1. As used herein, "aspect ratio" refers to the ratio of a length to a width, where length and width measured perpendicular to one another, and the length refers to the longest linearly measured dimension.

A nanostructure core may be formed from any suitable material. For instance, in one embodiment, a nanostructure core comprises an inorganic material. The inorganic material may include, for example, a metal (e.g., Ag, Au, Pt, Fe, Cr, Co, Ni, Cu, Zn, Ti, Pd and other metals), a semiconductor (e.g., Rh, Ge, silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The nanostructure core may, in some cases, be in the form of a quantum dot, a carbon nanotube, a carbon nanowire, or a carbon nanorod. In some cases, the nanostructure core comprises, or is formed of, a material that is not of biological origin. In some embodiments, a nanostructure includes one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. In certain embodiments, the nanostructure core does not include a polymeric material (e.g., it is non-polymeric).

The surface of the nanostructure core may include the material used to form the interior portions of the core, or the surface of the nanostructure core may be passivated by one or more chemicals to facilitate attachment of components (e.g., components that form a shell).

In some cases, core 16 is hollow and therefore does not include a nanostructure core. Thus, in some such and other embodiments, structure 10 includes a shell that can optionally allow components (e.g., bioactive agents, cholesterol) to pass to and from core 16 and an environment 40 outside of the shell. In contrast to certain existing hollow structures (e.g., liposomes) which typically have a largest cross-sectional dimension of greater than about 100 nm due to the steric hindrance of the components forming the shell, structures 10 having a hollow core (e.g., a partially or wholly hollow core) may be very small, e.g., having a largest cross-sectional dimension of less than about 100 nm, or even less than about 50 nm. For example, liposomes that include a lipid bilayer comprising phospholipids are difficult to fabricate having a size of less than 100 nm since the phospholipids become limited sterically, thus making it difficult or impossible to form bilayered hollow structures with small radii of curvature. Using a nanostructure core as a template for phospholipids or other molecules, and then removing the nanostructure core, may result in hollow or at least partially hollow structures with small radii of curvature. Examples of methods that can used to form hollow cores are described in more detail in International Patent Publication No. WO/2009/131704, filed Apr. 24, 2009 and entitled, "Nanostructures Suitable for Sequestering Cholesterol and Other Molecules, which is incorporated herein by reference in its entirety for all purposes.

Structures described herein, which may include a shell surrounding a core, may also have any suitable shape and/or size. For instance, a structure may have a shape that is substantially spherical, oval, rod-shaped, pyramidal, cubed-like, disk-shaped, or irregularly shaped. The largest cross-sectional dimension (or, sometimes, a smallest cross-section dimension) of a structure may be, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. The structure may also have an aspect ratio substantially similar to the aspect ratio of the core.

A shell of a structure can have any suitable thickness. For example, the thickness of a shell may be at least 10 Angstroms, at least 0.1 nm, at least 1 nm, at least 2 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell). The shell may have a combination of the above-noted ranges.

Those of ordinary skill in the art are familiar with techniques to determine sizes of structures and particles. Examples of suitable techniques include dynamic light scattering (DLS) (e.g., using a Malvern Zetasizer instrument), transmission electron microscopy, scanning electron microscopy, electroresistance counting and laser diffraction. Other suitable techniques are known to those or ordinary skill in the art. Although many methods for determining sizes of nanostructures are known, the sizes described herein (e.g., largest or smallest cross-sectional dimensions, thicknesses) refer to ones measured by dynamic light scattering.

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers.

The components of a shell may be charged in some cases, e.g., to impart a charge on the surface of the structure. In other cases, the components of a shell or the surface of the structure is uncharged. The surface charge of a structure may be measured by its zeta potential. In some cases, a structure has a zeta potential of, for example, between −2 mV and +2 mV, between −5 mV and +5 mV, between −7 mV and +7 mV, between −10 mV and +10 mV, between −20 mV and +20 mV, between −30 mV and +30 mV, between −40 mV and +40 mV, between −50 mV and +50 mV, between −60 mV and +60 mV, between 0 mV and ±5 mV, between ±10 mV and ±30 mV, between ±30 mV and ±40 mV, between ±40 mV and ±60 mV, or between ±60 mV and ±80 mV. In some cases, the zeta potential of a structure described herein is less than or equal to −2 mV, less than or equal to −5 mV, less than or equal to −7 mV, less than or equal to −10 mV, less than or equal to −20 mV, less than or equal to −30 mV, less than or equal to −40 mV, less than or equal to −50 mV, or less than or equal to −60 mV. In other embodiments, the zeta potential of a structure described herein is +2 mV or greater, +5 mV or greater, +7 mV or greater, +10 mV or greater, +20 mV or greater, +30 mV or greater, +40 mV or greater, +50 mV or greater, or +60 mV or greater. Other values of zeta potential are also possible.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where multilayers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), sterol lipids and prenol lipids (derived from condensation of isoprene subunits), fatty acids (e.g., tri-, di-, and monoglycerides), sterol-containing metabolites (e.g., cholesterol), and derivatives thereof.

In one particular set of embodiments, a structure described herein includes one or more phospholipids. The one or more phospholipids may include, for example, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure. In certain embodiments, a structure described herein includes one or more phospholipids that resemble those found in endogenous HDLs.

Non-phosphorus containing lipids may also be used such as stearylamine, docecylamine, acetyl palmitate, and fatty acid amides. In other embodiments, other lipids such as fats, oils, waxes, sterols, and fat-soluble vitamins (e.g., vitamins A, D, E and K) can be used to form portions of a structure described herein.

A portion of a structure described herein such as a shell or a surface of a nanostructure may optionally include one or more alkyl groups, e.g., an alkane-, alkene-, or alkyne-containing species, that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between $C_2$ and $C_{40}$, and in some embodiments may be greater than $C_5$, $C_{10}$, $C_{15}$, $C_{20}$, $C_{25}$, $C_{30}$, or $C_{35}$. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The alkyl group may include any suitable end group, e.g., a thiol group, a silane group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group (e.g., a carboxylic acid that allows attachment of a bioactive agent such as a nucleic acid). In some instances, the second end group can participate in a ligand/receptor interaction (e.g., biotin/streptavidin).

In some embodiments, the shell includes a polymer. For example, an amphiphilic polymer may be used. The polymer may be a diblock copolymer, a triblock copolymer, etc., e.g., where one block is a hydrophobic polymer and another block is a hydrophilic polymer. For example, the polymer may be a copolymer of an α-hydroxy acid (e.g., lactic acid) and polyethylene glycol. In some cases, a shell includes a hydrophobic polymer, such as polymers that may include certain acrylics, amides and imides, carbonates, dienes, esters, ethers, fluorocarbons, olefins, sytrenes, vinyl acetals, vinyl and vinylidene chlorides, vinyl esters, vinyl ethers and ketones, and vinylpyridine and vinylpyrrolidones polymers. In other cases, a shell includes a hydrophilic polymer, such as polymers including certain acrylics, amines, ethers, styrenes, vinyl acids, and vinyl alcohols. The polymer may be charged or uncharged. As noted herein, the particular components of the shell can be chosen so as to impart certain functionality to the structures.

Where a shell includes an amphiphilic material, the material can be arranged in any suitable manner with respect to the core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

In some cases, the components that form a shell of a structure described herein are chosen, at least in part, on the molecular weight of the component. In some cases, the shell comprises, or is substantially formed of, a component having a molecular weight of, for example, less than or equal to 50,000 g/mol, less than or equal to 25,000 g/mol, less than or equal to 15,000 g/mol, less than or equal to 10,000 g/mol, less than or equal to 7,000 g/mol, less than or equal to 5,000 g/mol, less than or equal to 2,000 g/mol, less than or equal to 1,000 g/mol, or less than or equal to 500 g/mol. In other embodiments, the molecular weight of a component is 1,000 g/mol or greater, 2,000 g/mol or greater, 5,000 g/mol or greater, 7,000 g/mol or greater, 10,000 g/mol or greater, 15,000 g/mol or greater, 25,000 g/mol or greater, or 50,000 g/mol or greater. The component may be in the form of a polymer or a non-polymer (e.g., a lipid), such as those described herein.

In certain embodiments, a structure comprises a shell including a mixed layer (e.g., mixed monolayer) of components. For example, in one embodiment, the shell may include at least two types of lipids (e.g., a first lipid and a second lipid) such as those described herein, which form a mixed layer (e.g., a monolayer). In some embodiments including certain structures having a shell comprising a bilayer configuration, at least one of the layers may include a mixture of first and second components. In one set of embodiments, the shell may include a lipid such as those described herein (e.g., a first component), and a compound including an alkyl group such as those described herein (e.g., a second component) that can be attached to a nanostructure core, and the two components may form a mixed layer (e.g., monolayer). The alkyl group may have various carbon numbers, e.g., between $C_2$ and $C_{40}$, and may optionally have attached to it one or more suitable end groups, e.g., a thiol group, a silane group, an amino group (e.g., an unsubstituted or substituted amine), an amide group, an imine group, a carboxyl group, or a sulfate group, which may, for example, allow attachment of the group to a nanostructure core directly or via a linker. In some cases, one of the components in a mixed layer includes one end for attachment to a nanostructure core, and a second end for attachment to a bioactive agent such as a nucleic acid. Other types of components can also be included in a mixed layer of a shell. In certain embodiments, a mixed layer may include 3 or more, or 4 or more different components that form the layer. In some cases, the mixed layer is a self-assembled monolayer.

In embodiments in which there are 2 or more components that form a layer, each component may be present in the layer in an amount of, for example, at least 5%, at least 10%, at least 20%, at least 30%, at least 40%, at least 50%, at least 60%, at least 70%, at least 80%, or at least 90% of the layer by weight. For instance, in a 2-component system, the percentage of a first component relative to the total amount of first and second components in a mixed layer (by weight) may be, for example, at least 5%, at least 10%, at least 20%, at least 30%, at least 40%, at least 50%, at least 60%, at least 70%, at least 80%, or at least 90%. In other embodiments, in a 2-component system, the percentage of a first component relative to the total number of first and second components in a mixed layer may be, for example, at least 5%, at least 10%, at least 20%, at least 30%, at least 40%, at least 50%, at least 60%, at least 70%, at least 80%, or at least 90%.

In one set of embodiments, the structures described herein are constructed and arranged to sequester, transport, or exchange certain molecules to and/or from a subject or a biological sample. The structure, which may include one or more nucleic acids, may also function to deliver nucleic acids, release nucleic acids, and/or regulate gene expression in the sample or patient. Thus, certain structures herein may have multiple functions.

In one set of embodiments, the structures described herein, whether including a nanostructure core or a hollow core, is constructed and arranged to sequester, transport, or exchange certain molecules to and/or from a subject or a biological sample. For instance, when introduced into a subject, a structure may interact with one or more components in the subject such as cells, tissues, organs, particles, fluids (e.g., blood), and portions thereof. The interaction may take place, at least in part, through the shell of the structure, and may involve, for example, the exchange of materials (e.g., proteins, peptides, polypeptides, nucleic acids, nutrients) from the one or more components of the subject to the structure, and/or from structure to the one or more components of the subject. In some such embodiments, the shell of the structure can be designed to include components with properties that allow favorable interaction (e.g., binding, adsorption, transport) with the one or more materials from the subject. For example, the shell may include components having a certain hydrophobicity, hydrophilicity, surface charge, functional group, specificity for binding, and/or density to facilitate particular interactions, as described herein. In certain embodiments, one or more materials from a subject are sequestered by the structure, and the structure may facilitate excretion, breakdown, and/or transport of the material. The excretion, breakdown, and/or transport of the material can lead to certain beneficial and/or therapeutic effects. As such, the structures described herein can be used for the diagnosis, prevention, treatment or management of certain diseases or bodily conditions.

In one particular set of embodiments, a structure described herein is constructed and arranged to sequester cholesterol (and/or other lipids). Without wishing to be bound by theory, it is hypothesized that certain structures described herein can sequester cholesterol through hydrophobic interactions with a hydrophobic layer (e.g., a lipid layer such as a lipid bilayer) of the structure. For example, in some cases, cholesterol can bind to a surface of the structure (e.g., to the outer surface of the shell) through hydrophobic interactions. In other cases, the cholesterol can be transported from an outer surface of the shell to an inner surface of the shell and/or to the core of the structure. The cholesterol can also be imbedded in the shell, e.g., between two layers of the shell. Optionally, structures described herein may include one or more apolipoproteins (e.g., apolipoprotein-A1), proteins, or peptides, which may facilitate the sequestering of cholesterol and/or other lipids. The structures described herein may also sequester cholesterol by removing cholesterol and phospholipids from a cell, or from other circulating lipoprotein species. Cholesterol sequestered by structures described herein may, in some embodiments, be esterified enzymatically (e.g., by lecithin:acyl CoA transferase (LCAT)) to form a cholesteryl ester that may migrate towards the center of the structure. As described herein, structures that are adapted to sequester cholesterol may also function to deliver nucleic acids and/or regulate gene expression in a patient or sample.

Additionally, without wishing to be bound by theory, it is believed that certain structures described herein can sequester cholesterol from high concentrations of cholesterol (e.g., plaques) and transfer it to the liver directly or indirectly. For example, cholesterol may be sequestered from areas of high concentrations of cholesterol (e.g., plaques) by direct efflux of cholesterol from the plaque, or any components of the plaque, into or onto the structures described herein. In some such embodiments, the cholesterol that is sequestered by the structures is transported directly to the liver by the structures. In other embodiments, other circulating lipoprotein species (e.g., LDL) may participate in cholesterol exchange. For example, in some cases, free cholesterol or esterified cholesterol is transferred from other lipoproteins to the structures described herein. In other cases, once free cholesterol or esterified cholesterol is sequestered by the structures described herein, the cholesterol can be transferred from the structures to the other lipoprotein species, which may ultimately end up in the liver. Thus, in such embodiments, the structures described herein can augment reverse cholesterol transport indirectly. Furthermore, in the case where free cholesterol or esterified cholesterol is sequestered from the structures described herein to other lipoprotein species, the structures may further sequester cholesterol from, for example, areas of high cholesterol content, plaques, circulating lipoproteins, or other physiologic sites of high cholesterol concentration. It should be understood, however, that the structures described herein may remove cholesterol and/or other molecules by other routes, such as through urine, and the invention is not limited in this respect. In some embodiments, the structures can sequester cholesterol by these or other routes, and may also function to deliver nucleic acids and/or regulate gene expression prior, during, or after the sequestering process.

The amount of a molecule (e.g., cholesterol or other lipids) sequestered by a structure and/or a composition described herein may depend on, for example, the size of the structure, the biology and surface chemistry of the particle, as well as the method of administration. For instance, if the structures are circulated indefinitely from the periphery to the liver and out again, relative few cholesterol molecules need to be sequestered by each structure in order for the composition to be effective, since the structures are recycled. On the other hand, if a composition is used, for example, as a cholesterol or bile-salt binding resin orally, each structure may sequester a larger number of cholesterol to increased cholesterol uptake. Also, if the structures are of a size such that they are rapidly excreted (e.g., through the liver or urine) after sequestering cholesterol, a high uptake of cholesterol per structure, and/or continuous infusion may be implemented. As such, a single structure described herein, which may be incorporated into a pharmaceutical composition or other formulation, may be able to sequester any suitable number of a particular type of molecule (e.g., lipids such as cholesterol; steroids such as estrogen, progesterone, and testosterone; bile salts, etc.) during use, e.g., at least 2, at least 5, at least 10, at least 20, at least 30, at least 50, at least 100, at least 200, at least 500, at least 1,000, at least 2,000, at least 5,000, or at least 10,000 molecules, which may depend on the size (e.g., surface area and/or volume) of the structure, the particular application, and the method of administration. In some cases, such numbers of molecules can be bound to the structure at one particular instance.

In some cases, a single structure has a binding constant for cholesterol, $K_d$, of, for example, less than or equal to about 50 mM, less than or equal to about 15 mM, less than or equal to about 10 mM, less than or equal to about 5 mM, less than or equal to about 1 mM, less than or equal to about 100 µM, less than or equal to about 10 µM, less than or equal to about 1 µM, less than or equal to about 0.1 µM, less than or equal to about 50 nM, less than or equal to about 15 nM, less than or equal to about 10 nM, less than or equal to about 7 nM, less than or equal to about 5 nM, less than or equal to about 4 nM, less than or equal to about 2 nM, less than or equal to about 1 nM, less than or equal to about 0.1 nM, less than or equal to about 10 pM, less than or equal to about 1 pM, less than or equal to about 0.1 pM, less than or equal to about 10 fM, or less than or equal to about 1 fM. In some embodiments, the structures have a binding constant for cholesterol less than the concentration of total cholesterol in vivo. In some cases, the total cholesterol is the amount of circulating cholesterol. In certain embodiments, the structures have a binding constant for cholesterol substantially similar to that of endogenous HDL. Methods for determining the amount of cholesterol sequestered and binding constants are provided in more detail below.

In certain embodiments, the molecules that are sequestered by the structures described herein cause the structure to grow in size (e.g., cross-sectional area, surface area and/or volume), e.g., depending on the number of molecules sequestered. The molecules may associate with a surface of a structure, be imbedded in a shell of a structure, be transported to a core of the structure, or combinations thereof, as described herein. As such, the size of a structure (e.g., cross-sectional area, surface area and/or volume) can increase by at least 5%, at least 10%, at least 20%, at least 30%, at least 50%, at least 70%, or at least 100%, from a time prior to sequestration compared to a time after/during sequestration in some embodiments.

It should be understood, however, that while many of the embodiments herein are described in the context of sequestering cholesterol or other lipids, the invention is not limited as such and the structures, compositions, kits, and methods described herein may be used to sequester other molecules and/or to prevent, treat, or manage other diseases or bodily conditions, optionally in combination with nucleic acid delivery and/or gene regulation.

As described herein, the structures described herein may optionally include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

An example of a suitable protein that may associate with a structure described herein is an apolipoprotein, such as apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Specifically, apo A1, apo A2, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. A structure may include any suitable number of, e.g., at least 1, 2, 3, 4, 5, 6, or 10, apolipoproteins or analogues thereof. In certain embodiments, a structure includes 1-6 apolipoproteins, similar to a naturally occurring HDL particle. Of course, other proteins (e.g., non-apolipoproteins) can also be included in structures described herein.

In certain embodiments, structures describe herein may exhibit a binding affinity to macrophages and hepatocytes substantially equal to the binding affinity of endogenous HDL. In some cases, the structures described herein comprises a density of an apolipoprotein (e.g., Apo A-1) that is within 30%, within 20%, or within 10% of the density of the apolipoprotein on endogenous HDL.

Optionally, one or more enzymes may also be associated with a structure described herein. For example, lecithin-cholesterol acyltransferase is an enzyme which converts free cholesterol into cholesteryl ester (a more hydrophobic form of cholesterol). In naturally-occurring lipoproteins (e.g., HDL and LDL), cholesteryl ester is sequestered into the core of the lipoprotein, and causes the lipoprotein to change from a disk shape to a spherical shape. Thus, structures described herein may include lecithin-cholesterol acyltransferase to mimic HDL and LDL structures. Other enzymes such as cholesteryl ester transfer protein (CETP) which transfers esterified cholesterol from HDL to LDL species may also be included.

In some cases, one or more bioactive agents are associated with a structure or a composition described herein. The one or more bioactive agents may optionally be released from the structure or composition (e.g., long-term or short-term release). Bioactive agents include molecules that affect a biological system and include, for example proteins, nucleic acids, therapeutic agents, vitamins and their derivatives, viral fractions, lipopolysaccharides, bacterial fractions and hormones. Other agents of interest may include chemotherapeutic agents, which are used in the treatment and management of cancer patients. Such molecules are generally characterized as antiproliferative agents, cytotoxic agents and immunosuppressive agents and include molecules such as taxol, doxorubicin, daunorubicin, vinca-alkaloids, actinomycin and etoposide.

Other examples of bioactive agents include cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories (e.g., glucocorticoids such as prednisone), nucleic acid species (e.g., anti-sense and siRNA species against inflammatory mediators), antineoplastics, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hypoglycemic agents, hypolipidemic agents, agents useful for erythropoiesis stimulation, antiulcer/antireflux agents, antinauseants/ antiemetics and oil-soluble vitamins, cholesterol agents (e.g., statins such as Lipitor, Zocor, which may be known to lower cholesterol levels), or combinations thereof.

In some embodiments, one or more nucleic acids is associated with a structure described herein. A nucleic acid includes any double strand or single strand deoxyribonucleic acid (DNA) or ribonucleic acid (RNA) of variable length. Nucleic acids include sense and anti-sense strands. Nucleic acid analogs such as phosphorothioates, phosphoramidates, phosphonates analogs are also considered nucleic acids and may be used. Nucleic acids also include chromosomes and chromosomal fragments.

In some cases, the nucleic acid is an oligonucleotide. A nucleic acid or oligonucleotide may be associated with a structure described herein in any suitable manner (e.g., with the core, a shell, or combination thereof) as discussed herein. The nucleic acid or oligonucleotide may be adapted and arrange to regulate gene expression in a sample or a patient. Any suitable technique may be used to attach a nucleic acid or an oligonucleotide to a portion of a structure described herein, for instance, electrostatic adsorption techniques, chemisorption techniques, gold-thiol conjugation chemistry, or the like. In some instances, the nucleic acid or oligonucleotide is covalently or near-covalently bonded to the nanostructure core or to the shell. In other instances, the nucleic acid or oligonucleotide is covalently attached to cholesterol (e.g., 5'-cholesteryl DNA) and associated in any suitable manner with a structure described herein. The nucleic acid or oligonucleotide may include, for example, DNA, RNA, or the like, and may be single stranded or double stranded. In some cases, the nucleic acid or oligonucleotide may be antisense DNA. Specific examples of RNA include, without limitation, siRNA, mRNA, miRNA, tRNA, etc. In some cases, for example, the RNA may be siRNA or other types of RNA selected to regulate gene expression in a cell to which the nanoparticle is targeted. In certain embodiments, the nucleic acid or oligonucleotide is synthetic. In some cases, the nucleic acid or oligonucleotide is cholesterylated.

As noted above, a nucleic acid compound or oligonucleotide described herein may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid or oligonucleotide may comprise a nucleotide sequence that is complementary to a region consisting of no more than 1000, no more than 500, no more than 250, no more than 100 or no more than 50, 35, 30, 25, 22, 20, 18, 15, 12, 10, 8, 6, 5, 4, or 3 nucleotides (nucleotide bases or nucleobases) of the full-length nucleic acid sequence or ligand nucleic acid sequence. The region of complementarity may be at least 8 nucleotides, and optionally at least 10 or at least 15 nucleotides, optionally between 15 and 25 nucleotides, or optionally between 3 and 20 nucleotides (e.g., between 3 and 10 nucleotides, or between 3 and 10 nucleotides). A region of complementarity may fall within an intron, a coding sequence or a noncoding sequence of the target transcript, such as the coding sequence portion.

A nucleic acid described herein (which may be associated with a nanostructure) may have a length of about 3 to about 1000 nucleotides (nucleotide bases or nucleobases) or base pairs in length, about 3 to about 700 nucleotides or base pairs in length, about 4 to about 500 nucleotides or base pairs in length, about 3 to about 200 nucleotides or base pairs in length, about 3 to about 150 nucleotides or base pairs in length, about 3 to about 100 nucleotides or base pairs in length, about 3 to about 75 nucleotides or base pairs in length, about 10 to about 50 nucleotides or base pairs in length, about 10 to about 40 nucleotides or base pairs in length, about 10 to about 30 nucleotides or base pairs in length, about 10 to about 25 nucleotides or base pairs in length, about 3 to about 30 nucleotides or base pairs in length, about 3 to about 20 nucleotides or base pairs in length, or about 3 to about 10 nucleotides or base pairs in length. In some embodiments, a nucleic acid includes about 200 nucleotides or base pairs in length or less, about 150 nucleotides or base pairs in length or less, about 100 nucleotides or base pairs in length or less, about 75 nucleotides or base pairs in length or less, about 50 nucleotides or base pairs in length or less, about 30 nucleotides or base pairs in length or less, about 25 nucleotides or base pairs in length or less, about 20 nucleotides or base pairs in length or less, about 15 nucleotides or base pairs in length or less, or about 10 nucleotides or base pairs in length or less. Other lengths are also possible. As described herein, the nucleic acid may be single stranded in some embodiments, and double stranded in other embodiments.

In certain embodiments, structures described herein may include very short oligonucleotides that can be used to bind a target. For example, microRNAs may bind to 3'-UTRs through "seed sequence" pairings that may be as short as 3 or 4 bases long.

In certain embodiments, a targeted sequence may have a length such as one described above with respect to a nucleic acid that can be associated with a structure described herein. For example, a targeted sequence may have a length of about 3 to about 1000 nucleotides in length, about 3 to about 700 nucleotides in length, about 4 to about 500 nucleotides in length, about 3 to about 200 nucleotides in length, about 3 to about 150 nucleotides in length, about 3 to about 100 nucleotides in length, about 3 to about 75 nucleotides in length, about 10 to about 50 nucleotides in length, about 10 to about 40 nucleotides in length, about 10 to about 30 nucleotides in length, about 10 to about 25 nucleotides in length, about 3 to about 30 nucleotides in length, about 3 to about 20 nucleotides in length, or about 3 to about 10 nucleotides in length. Other lengths are also possible.

A nucleic acid or oligonucleotide may be a DNA (particularly for use as an antisense), RNA or RNA:DNA hybrid. Any one strand may include a mixture of DNA and RNA, as well as modified forms that cannot readily be classified as either DNA or RNA. For example, in some cases, the nucleic acid is single stranded, and is a hybrid of RNA and DNA nucleobases. Likewise, a double stranded compound may be DNA:DNA, DNA:RNA or RNA:RNA, and any one strand may also include a mixture of DNA and RNA, as well as modified forms that cannot readily be classified as either DNA or RNA. For example, in some cases, the nucleic acid is a duplex with one, or the other, or both strands made of RNA and DNA nucleobases. The nucleic acid or oligonucleotide associated with a structure described herein may be recombinant in some embodiments.

The nucleic acid or oligonucleotide associated with a structure described herein may include any of a variety of modifications, including one or modifications to the backbone (the sugar-phosphate portion in a natural nucleic acid, including internucleotide linkages) or the base portion (the purine or pyrimidine portion of a natural nucleic acid). For example, in some cases one or more of the nucleobases used to fabricate the nucleic acid are modified with certain chemical moieties such as, for example, phosphorthioate, morpholino, 2'-F, and 2'-OMe. In some embodiments, the nucleic acid is modified with a fluorophore, or other imaging agent (e.g., gadolinium, radionuclide). For example, the nucleic acid may include a fluorophore that is adapted to change in fluorescence intensity upon binding to a target protein or a small molecule. In another example, an antisense nucleic acid compound may, in some embodiments, have a length of about 3 to about 30 nucleotides and may contain one or more modifications to improve characteristics such as stability in the serum, in a cell or in a place where the compound is likely to be delivered. In the case of an RNAi construct, the strand complementary to the target transcript may be RNA or modifications thereof. The other strand may be RNA, DNA or any other variation. The duplex portion of double stranded or single stranded "hairpin" RNAi construct may have a length of, for example, 18 to 40 nucleotides in length and optionally about 20 to 30 nucleotides in length for example. Catalytic or enzymatic nucleic acids may, in some cases, be ribozymes or DNA enzymes and may also contain modified forms.

In certain embodiments, nucleic acid or oligonucleotide associated with a structure described herein is modified with a lipid, such as one described herein. For example, a nucleic acid or oligonucleotide may be cholesterylated, e.g., the nucleic acid may comprise a 5'-cholesteryl DNA or 3'-cholesteryl DNA.

The nucleic acids or oligonucleotides associated with the structures described herein can be fabricated using any suitable method, including those methods described herein and those known to one of ordinary skill in the art. The nucleic acids or oligonucleotides may optionally be modified in any suitable manner to facilitate attachment to a portion of a structure described herein. For example, as noted above, in one embodiment, a nucleic acid or oligonucleotide, prior to attachment, has an end modified to include a cholesterol function group. In another embodiment, a nucleic acid or oligonucleotide, prior to attachment, has an end modified to include an alkylthiol. Other modifications are also possible such as those described herein.

Nucleic acid compounds and oligonucleotides, when associated with a structure as described herein, may regulate or modulate expression (e.g., inhibit expression) of the target by at least about 50%, at least about 60%, at least about 70%, at least about 80%, or at least about 90% when contacted with a biological sample or patient under physiological conditions and at a concentration where a nonsense or sense control has little or no effect. In some embodiments, nucleic acid compounds and oligonucleotides, when associated with a structure as described herein, may regulate or modulate expression (e.g., inhibit expression) of the target by at least about 50% more, at least about 60% more, at least about 70% more, at least about 80% more, or at least about 90% more than the same nucleic acid compounds and oligonucleotides that are not associated with structures described herein (e.g., free nucleic acid compounds and oligonucleotides) when contacted with a biological sample or patient under physiological conditions.

In some embodiments, certain structures described herein that can regulate gene expression of a target in one or more of the above-noted ranges is a structure that mimics endogenous HDL. For instance, the structure may include a nucleic acid and/or oligonucleotide and a core substantially surrounded by a shell comprising a lipid (e.g., a phospholipid) and an apolipoprotein. Such a structure may regulate gene expression of a target by at least about 50% more, at least about 60% more, at least about 70% more, at least about 80% more, or at least about 90% more, when contacted with a biological sample or patient under physiological conditions, than either 1) a similar structure that mimics HDL but does not include the nucleic acid compounds and/or oligonucleotides; or, in other embodiments, 2) the same nucleic acid compounds and/or oligonucleotides associated with a structure that does not mimic endogenous HDL.

In some cases, structures described herein, which may include one or more nucleic acid compounds or oligonucleotides, may have relatively high cellular uptake. For example, for a composition including a plurality of structures that is delivered to cells, at least 80%, at least 85%, at least 90%, at least 95%, at least 97%, or at least 99% of the structures in a composition may be uptaken by the cells.

In certain embodiments, structures described herein, which may include one or more nucleic acid compounds or oligonucleotides, may have relatively low endosomal sequestration (e.g., a relatively high percentage of the structures may reside in the cytoplasm of the cell) upon delivery of the structures to cells. For example, at least 50%, at least 60%, at least 70%, at least 80%, at least 85%, at least 90%, at least 95%, at least 97%, or at least 99% of the structures that enter into a cell may reside in the cytoplasm of the cell. As described herein, avoidance of endosomal sequestration may allow the structures to have a greater therapeutic effect.

It should be understood that the components described herein, such as the lipids, phospholipids, alkyl groups, polymers, proteins, polypeptides, peptides, enzymes, bioactive agents, nucleic acids, and species for targeting described above, may be associated with a structure in any suitable manner and with any suitable portion of the structure, e.g., the core, the shell, or both. For example, one or more such components may be associated with a surface of a core, an interior of a core, an inner surface of a shell, an outer surface of a shell, and/or embedded in a shell. Furthermore, such components can be used, in some embodiments, to facilitate the exchange and/or transport of materials (e.g., proteins, peptides, polypeptides, nucleic acids, nutrients) from one or more components of a subject (e.g., cells, tissues, organs, particles, fluids (e.g., blood), and portions thereof) to a structure described herein, and/or from the structure to the one or more components of the subject. In some cases, the components have chemical and/or physical properties that allow favorable interaction (e.g., binding, adsorption, transport) with the one or more materials from the subject.

Additionally, the components described herein, such as the lipids, phospholipids, alkyl groups, polymers, proteins, polypeptides, peptides, enzymes, bioactive agents, nucleic acids, and species for targeting described herein, may be associated with a structure described herein prior to administration to a subject or biological sample and/or after administration to a subject or biological sample. For example, in some cases a structure described herein includes a core and a shell which is administered in vivo or in vitro, and the structure has a greater therapeutic effect after sequestering one or more components (e.g., an apolipoprotein) from a subject or biological sample. That is, the structure may use natural components from the subject or biological sample to increase efficacy of the structure after it has been administered.

In some embodiments, structures described herein can include a modular nucleic acid component for controlling the release of nucleic acid from the structure (e.g., nanostructure core surface) by various stimuli. The stimuli may include, for example, ex vivo (e.g., light), physiologic (e.g., reducing intracellular environment), or pathologic (e.g., reactive oxygen species or low pH) triggers. Tuning the properties of the structure may also be used to facilitate release of nucleic acids from the structure. For example, portions of the shell (e.g., lipids such as phospholipids), charge of the structure (e.g., surface of the structure), presence and/or absence of proteins, and/or ligands attached to surface adsorbed nucleic acids (e.g., cholesterol, other lipids, etc.) can be modified, in some embodiments, to facilitate release of a nucleic acid from the structure. Nucleic acid triggered release mechanisms may be used to provide a way to test the mechanism of action of the structure once inside cells, compare materials with different release chemistries, and/or address bio-nano interfacial challenges (e.g., endosomal sequestration) that may surface after initial testing.

In some embodiments, structures that can be used to release nucleic acids may be fabricated using, for example, Au—S coupling of oligonucleotides (e.g. DNA) to the surface of the nanostructure core. Example of components that can be used with structures described herein for nucleic acid release are described in Example 5 in connection with FIG. 15. In some embodiments, the structure may effectively sequester the gene regulating portion of the nucleic acid sequence on the surface of the core or within the shell of a structure, and the gene regulating portion may not be available to the intracellular cytoplasmic machinery required to regulate gene expression. For example, the shell of the structure surrounding the core may prevent or inhibit the nucleic acid from being exposed to the intracellular cytoplasmic machinery required to regulate gene expression, but the structure may be adapted to release the nucleic acid upon triggering. Advantageously, the timing of nucleic acid release can be controlled by such a method. Furthermore, in some embodiments, by sequestering the nucleic acid within the shell of the structure such that the nucleic acid is not exposed or is minimally exposed to the surface of the structure, breakdown of the nucleic acid by nucleases can be prevented or reduced. Accordingly, in some cases, nucleic acids and oligonucleotides, when associate with a structure as described herein, may have reduced susceptibility to nuclease degradation.

In one set of embodiments, a method of treatment includes delivering a plurality of structures described herein to a sample or patient, wherein the structure includes a shell (e.g., comprising a lipid or other entity) substantially surrounding a core and an oligonucleotide adapted to regulate gene expression. The method also includes releasing the oligonucleotide from the structure to the sample or patient, and regulating gene expression in the sample or patient.

In some embodiments, the structures, compositions, and methods described herein can be used for targeting, such that the structures described herein can be delivered to specific target sites. Targeting may include, in some embodiments, functionalizing the structure with one or more ligands or receptors specific for a particular target site or sites. For instance, a structure described herein may include a ligand for a receptor (or a receptor for a ligand) that is expressed on the surface of a site to be targeted. Examples of specific surface components include antibodies (including antibody fragments and derivatives), plaque markers, specific cell surface markers, small molecules (e.g., folate), and aptamers, i.e., a nucleic acid able to specifically bind a specific target molecule, such as a biological moiety (e.g., RNA aptamers and DNA aptamers). Examples of specific targets in atherosclerotic plaques and in vascular endothelial cells in the vicinity of the plaque include but are not limited to: fibrin, macrophages, VCAM-1, E-selectin, integrin [alpha]$_v$ [beta]$_3$, P-selectin and P-selectin glycoprotein ligand-1

(PSGL-1). Furthermore, a protein component of the structures described herein could be modified and used as the targeting molecule, e.g. Apo E, or Apo $A_1$. The structures may also include certain groups (e.g., asialo groups) for targeting specific small molecules.

In one aspect, structures such as those described herein may be targeted to macrophages or hepatocytes, or other immune cells. In one set of embodiments, for example, structures may be targeted to macrophages for the treatment of atherosclerosis. For example, the structures may be able to sequester cholesterol from macrophages to treat atherosclerosis and similar conditions implicating cholesterol and/or macrophages. The structures may also be adapted to deliver nucleic acids and/or regulate gene expression in the sample or patient.

In one set of embodiments, the structures, compositions and methods described herein are used to diagnose, prevent, treat or manage diseases or bodily conditions associated with abnormal lipid levels. For instance, high density lipoprotein is a dynamic serum nanostructure protective against the development of atherosclerosis and resultant illnesses such as heart disease and stroke. By administering certain compositions and methods described herein, such as those including structures that mimic naturally occurring HDL, circulating serum HDL levels (e.g., low HDL levels) may be increased. This can provide a promising therapeutic approach to, for example, preventing and potentially reversing atherosclerosis by augmenting reverse cholesterol transport. In other embodiments, compositions and methods described herein may be used to decrease LDL levels (e.g., decrease high LDL levels) or temporarily increase LDL levels, e.g., by using structure that mimics naturally occurring LDL. Furthermore, in certain embodiments, diagnosis, prevention, treatment or management of diseases or bodily conditions associated with abnormal lipid levels may involve using the structures, compositions and methods described herein to augment reverse cholesterol transport (e.g., directly or indirectly) by way of augmenting the flux of cholesterol through and out of the body. Such diagnosis, prevention, treatment, or methods of managing diseases or bodily conditions may include using the structures to regulate gene expression of a target and/or to deliver nucleic acids. Accordingly, certain structures described herein may both sequester cholesterol and function as a gene-regulating therapeutic.

With consideration given to mortality and world-wide prevalence, the significance of atherosclerosis is profound. Atherosclerosis is a chronic infiltrative and inflammatory disease of the systemic arterial tree caused by excess circulating cholesterol. Cholesterol is not soluble in the aqueous milieu of the human body, thus travels by way of dynamic nanoparticle carriers known as lipoproteins (LPs). The main LP carriers of cholesterol are low density lipoprotein (LDL) and high density lipoprotein (HDL). LDL originates in the liver and high circulating levels promote atherosclerosis and increase the risk of cardiovascular disease. Therapeutic LDL lowering has been shown to reduce cardiovascular disease mortality. Conversely, HDL is well-known to promote reverse cholesterol transport (RCT) from sites of peripheral deposition (macrophage foam cells) to the liver for excretion. Accordingly, high HDL levels inversely correlate with cardiovascular disease risk. There is intense interest in therapeutic strategies to harness the beneficial effects of HDL to address the substantial cardiovascular disease burden that exists despite current LDL lowering therapies. Structures described herein may be used, in some embodiments, to mimic endogenous HDL so as to treat atherosclerosis and to deliver nucleic acids and/or regulate gene expression at the same time. For example, in one set of embodiments, the structures described herein are capable of exhibiting the bio-mimetic characteristics of HDL with regard to cholesterol sequestration from macrophages, and are also surface-modified to deliver duplexed siRNA to hepatocytes for diminishing Apo B-100 protein expression, thereby inhibiting LDL production. Accordingly, the structures may function in two- or more cell types. Design of such structures having dual functionality may involve balancing the surface coverage of siRNA (or other oligonucleotide) so as to not, potentially, decrease the capacity for the particle to mediate reverse cholesterol efflux and vice versa.

In one particular embodiment, structures, compositions and methods described herein are used for treating atherosclerosis. Treating atherosclerosis may include performing a therapeutic intervention that results in reducing the cholesterol content of at least one atherosclerotic plaque, or prophylactically inhibiting or preventing the formation or expansion of an atherosclerotic plaque. Generally, the volume of the atherosclerotic plaque, and hence the degree of obstruction of the vascular lumen, will also be reduced. In some embodiments, the structures, compositions and methods are useful for treating atherosclerotic lesions associated with familial hyperlipidemias.

The compositions and methods described herein may reduce the cholesterol content of atherosclerotic plaques and/or the volume of atherosclerotic plaques. The cholesterol content may be reduced by, for example, at least 10%-30%, at least 30%-50%, and in some instances at least 50%-85% or more. The volume of the atherosclerotic plaques may also be reduced. The reduction in plaque volume may be, for example, at least 5%-30%, often as much as 50%, and in some instances 75% or more. Methods of determining the reduction of cholesterol content of atherosclerotic plaques and/or the volume of atherosclerotic plaques are known to those of ordinary skill in the art, and include intravascular ultrasound and magnetic resonance imaging.

Other diseases or bodily conditions associated with abnormal lipid levels which could benefit from the structures and/or compositions described herein include, for example, phlebosclerosis or any venous condition in which deposits of plaques containing cholesterol or other material are formed within the intima or inner media of veins, acute coronary syndromes, angina including, stable angina, unstable angina, inflammation, sepsis, vascular inflammation, dermal inflammation, congestive heart failure, coronary heart disease (CHD), ventricular arrythmias, peripheral vascular disease, myocardial infarction, onset of fatal myocardial infarction, non-fatal myocardial infarction, ischemia, cardiovascular ischemia, transient ischemic attacks, ischemia unrelated to cardiovascular disease, ischemia-reperfusion injury, decreased need for revascularization, coagulation disorders, thrombocytopenia, deep vein thrombosis, pancreatitis, non-alcoholic steatohepatitis, diabetic neuropathy, retinopathy, painful diabetic neuropathy, claudication, psoriasis, critical limb ischemia, impotence, dyslipidemia, hyperlipidemia, hyperlipoproteinemia, hypoalphalipoproteinemia, hypertriglyceridemia, any stenotic condition leading to ischemic pathology, obesity, diabetes including both Type I and Type II, ichtyosis, stroke, vulnerable plaques, lower-limb ulceration, severe coronary ischemia, lymphomas, cataracts, endothelial dysfunction, xanthomas, end organ dysfunction, vascular disease, vascular disease that results from smoking and diabetes, carotid and coronary artery disease, regress and shrink established plaques, unstable plaques, vessel intima that is weak, unstable vessel intima, endothelial injury, endothelial damage as a result of surgical procedures, morbidity associated with vascular disease, ulcerations in the arterial lumen, restenosis as a result of balloon angioplasty, protein storage diseases (e.g., Alzheimer's disease, prion disease), diseases of hemostasis (e.g., thrombosis, thrombophilia, disseminated intravascular coagulation, thrombocytopenia, heparin induced thrombocytopenia, thrombotic thrombocytopenic purpura), rheumatic diseases (e.g., multiple sclerosis, systemic lupus erythematosis, sjogren's syndrome, polymyositis/dermatomyositis, scleroderma), neuroligical diseases (e.g., Parkinson's disease, Alzheimer's disease), and subindications thereof. As described herein, such conditions may be treated or managed using the structures described herein, which may optionally be adapted to regulate gene expression of a target and/or to deliver nucleic acids. Certain methods of treatment or management of such diseases or conditions involve using the structures described herein to both sequester cholerestrol and function as a gene-regulating therapeutic.

Structures, compositions, and methods described herein may diagnose, prevent, treat, or manage diseases or bodily conditions associated with abnormal lipid levels, by, for example, decreasing triglycerides levels, increasing or decreasing the level of other lipids, increasing plaque stability or decreasing the probability of plaque rupture, increasing or decreasing vasodilation, treating or preventing inflammation, treating or preventing inflammatory diseases or an inflammatory response, strengthening or stabilizing smooth muscle and vessel intima, stimulating efflux of extracellular cholesterol for transport to the liver, modulating immune responses, mobilizing cholesterol from atherosclerotic plaques, modifying any membrane, cell, tissue, organ, and extracellular region and/or structure in which compositional and/or functional modifications would be advantageous, and/or regulating genes that express proteins that are associated with a disease or bodily condition. Combinations of two or more such methods can also be used to diagnose, prevent, treat, or manage diseases or bodily conditions.

In another set of embodiments, the structures, compositions and methods described herein are used for treating a subject having a vascular or a cardiovascular condition or is at risk of developing a cardiovascular condition are provided. Vascular conditions are conditions that involve the blood vessels (arteries and veins). Cardiovascular conditions are conditions that involve the heart and the blood vessels associated with the heart. Examples of vascular conditions include diabetic retinopathy, diabetic nephropathy, renal fibrosis, hypertension, atherosclerosis, arteriosclerosis, atherosclerotic plaque, atherosclerotic plaque rupture, cerebrovascular accident (stroke), transient ischemic attack (TIA), peripheral artery disease, arterial occlusive disease, vascular aneurysm, ischemia, ischemic ulcer, heart valve stenosis, heart valve regurgitation and intermittent claudication. Examples of cardiovascular conditions include coronary artery disease, ischemic cardiomyopathy, myocardial ischemia, and ischemic or post-myocardial ischemia revascularization.

Structures, compositions and methods described herein can also be used for treating a subject at risk for developing a cardiovascular condition. The degree of risk of a cardiovascular condition depends on the multitude and the severity or the magnitude of the risk factors that the subject has. Risk charts and prediction algorithms are available for assessing the risk of cardiovascular conditions in a human subject based on the presence and severity of risk factors. One commonly used algorithm for assessing the risk of a cardiovascular condition in a human subject based on the presence and severity of risk factors is the Framingham Heart Study risk prediction score. A human subject is at an elevated risk of having a cardiovascular condition if the subject's 10-year calculated Framingham Heart Study risk score is greater than 10%. Another method for assessing the risk of a cardiovascular event in a human subject is a global risk score that incorporates a measurement of a level of a marker of systemic inflammation, such as CRP, into the Framingham Heart Study risk prediction score. Other methods of assessing the risk of a cardiovascular event in a human subject include coronary calcium scanning, cardiac magnetic resonance imaging, and/or magnetic resonance angiography.

The structures, compositions and methods described herein may also be useful for prophylactic treatments. Prophylactic treatments may be useful following invasive vascular procedures. For instance, vascular regions having injured endothelium are at increased risk for developing atherosclerotic plaques. Therefore, invasive vascular procedures, such as coronary angioplasty, vascular bypass grafting, and other procedures that injure the vascular endothelial layer, may be practiced in conjunction with the methods of the present invention. As the invasive procedure injures the endothelium, the structures may act to remove cholesterol from the injured region and inhibit or prevent plaque formation of expansion during endothelial healing.

Hyperlipidemias may also be treated by the compositions and methods described herein. Administration of structures, alone or bound to a protein such as apo-A1 and apo-A2, to individuals having hypoalphalipoproteinemia from genetic or secondary causes, familial combined hyperlipidemia, and familial hypercholesterolemia is a useful treatment.

In another set of embodiments, the structures described herein may be used for treating cancer. Cancer cells may be dependent upon cholesterol delivery by HDL in order to maintain cell membrane biosynthesis and integrity. As such, structures described herein may be adapted to mimic endogenous HDL such that they can target cancer cells. The structures may also function to regulate gene expression once inside the cancer cells. For example, in one particular embodiment, the structures may include one or more oligonucleotides adapted to reduce intracellular miR-210 levels. Reducing intracellular miR-210 levels has been shown to inhibit angiogenesis in human umbilical vein endothelial cells, as well as induce apoptosis in cancer cell types. In another example, structures described herein may include an oligonucleotide that selectively binds to mRNA sequences within cancer cells to regulate gene expression. For example, a structure may include a nucleic acid sequence (e.g., anti-survivin oligonucleotide) that regulates the expression of survivin, an anti-apoptotic protein near universally upregulated in human cancer. The anti-survivin oligonucleotide has the potential to selectively bind intracellular survivin mRNA, knockdown survivin protein expression, and induce cancer cell death. Structures described herein may also include other oligonucleotides to treat cancer.

In some cases, the structures may be used as contrast agents in combination with one or more other functions such as sequestering cholesterol, delivering nucleic acids, and/or regulating gene expression. For example, the nanostructure core of the structure may comprise a material suitable for use as a contrast agent (e.g., gold, iron oxide, a quantum dot, radionuclide, etc.). In other embodiments, the shell may include a contrast agent. For instance, a nanoparticle or other suitable contrast agent may be embedded within the lipid bilayer of the shell, or associated with an inner or outer surface of the shell. The contrast agents may be used to enhance various imaging methods known to those in the art such as MRI, X-ray, PET, CT, etc.

In some embodiments, structures described herein may be used as intracellular diagnostic sensors. For instance, as described herein, structures including nucleic acids associated therewith may be delivered to the cytoplasm of cells where they regulate the expression of target RNA sequences and their protein targets. The ability to deliver nucleic acids intact to the cell cytoplasm provides an opportunity to not only regulate RNA targets, but also to detect them. For instance, in some embodiments, delivery of a "molecular beacon", where 3' and 5' fluor-quencher pairs are in close proximity due to hairpin self-hybridization may be used to detect an intracellular target mRNA through complementary binding to the beacon and relief of fluorescent quenching. In other embodiments, short nucleic acids may be designed to detect the presence of intracellular proteins (e.g., aptamers) or small molecules (e.g., ATP-sensor) through changes in fluorescence that occur due to target protein or small molecule binding, respectively. The structures described herein may be made to deliver nucleic acid sensors for a broad range of biomolecules that provide a convenient readout of their presence, for example, through increased fluorescence upon target molecule binding.

In some embodiments, a composition is introduced to a subject or a biological sample, and the structures of the composition and/or the subject or biological sample are exposed to assay conditions that can determine a disease or condition of the subject or biological sample. At least a portion of the structures may be retrieved from the subject or biological sample and an assay may be performed with the structures retrieved. The structures may be assayed for the amount and/or type of molecules bound to or otherwise sequestered by the structures. For example, in one set of embodiments, a competition assay is performed, e.g., where labeled cholesterol is added and displacement of cholesterol is monitored. The more measured uptake of labeled cholesterol, the less bound un-labeled free cholesterol is present. This can be done, for example, after a composition comprising the structures described herein are administered to a subject or a biological sample, and the structures are subsequently retrieved from the subject or biological sample. This method can be used, for example, where the structures are to be used as a diagnostic agent to see how much cholesterol (unlabeled) it has sequestered in a subject or biological sample.

Other methods can also be used to determine the amount of cholesterol sequestered by structures described herein. In some cases, labeled cholesterol (e.g., fluorescently-labeled cholesterol such as NBD-cholesterol, or radioactive cholesterol) can be used. Labeled cholesterol can be added to the structures either in vitro or in vitro. By adding structures without labeled cholesterol and measuring the fluorescence increase upon binding, one can calculate the binding constant of labeled cholesterol to the structure. In addition, to remove the cholesterol from the structure, one can dissolve the particle (e.g., KCN) and then measure the resultant fluorescence in solution. Comparing to standard curve can allow determination of the number of cholesterol molecules per particle. Other methods such as organic extraction and quantitative mass spectrometry can also be used to calculate amount of cholesterol sequestered by one or more structures described herein.

As described herein, the inventive structures may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for diagnosing, preventing, treating or managing a disease or bodily condition such as those described herein, including but not limited to ones associated with regulating gene expression. In some cases, the structures and compositions can be used for both diagnosis and therapeutic purposes. It should be understood that any suitable structures described herein can be used in such pharmaceutical compositions, including those described in connection with the figures. In some cases, the structures in a pharmaceutical composition have a nanostructure core comprising an inorganic material and a shell substantially surrounding and attached to the nanostructure core.

The pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The structures described herein may be orally administered, parenterally administered, subcutaneously administered, and/or intravenously administered. In certain embodiments, a structure or pharmaceutical preparation is administered orally. In other embodiments, the structure or pharmaceutical preparation is administered intravenously. Alternative routes of administration include sublingual, intramuscular, and transdermal administrations.

Pharmaceutical compositions described herein include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

The inventive compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient. An inventive structure may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein (e.g., for rectal or vaginal administration) may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the body and release the structures.

Dosage forms for the topical or transdermal administration of a structure described herein include powders, sprays, ointments, pastes, foams, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a structure described herein to the body. Dissolving or dispersing the structure in the proper medium can make such dosage forms. Absorption enhancers can also be used to increase the flux of the structure across the skin. Either providing a rate controlling membrane or dispersing the structure in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more inventive structures in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the inventive structures may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with structures and compositions described herein include time-release, delayed release, sustained release, or controlled release delivery systems, as described herein. Such systems may avoid repeated administrations of the structures in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The compositions may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiments. The structures and compositions described herein can also be combined (e.g., contained) with delivery devices such as syringes, pads, patches, tubes, films, MEMS-based devices, and implantable devices.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

Injectable depot forms can be made by forming microencapsule matrices of the structures described herein in biodegradable polymers such as polylactide-polyglycolide. Depending on the ratio of structure to polymer, and the nature of the particular polymer employed, the rate of release of the structure can be controlled. Examples of other biodegradable polymers include poly(orthoesters) and poly (anhydrides).

When the structures described herein are administered as pharmaceuticals, to humans and animals, they can be given per se or as a pharmaceutical composition containing, for example, about 0.1% to about 99.5%, about 0.5% to about 90%, or the like, of structures in combination with a pharmaceutically acceptable carrier.

The administration may be localized (e.g., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the structures described herein, which may be used in a suitable hydrated form, and/or the inventive pharmaceutical compositions, are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the structures described herein and a cocktail of other compounds that can be used to treat cancer.

The phrase "therapeutically effective amount" as used herein means that amount of a material or composition comprising an inventive structure which is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. One of ordinary skill in the art can determine what an effective amount of the composition is by, for example, methods such as assessing liver function tests (e.g. transaminases), kidney function tests (e.g. creatinine), heart function tests (e.g. troponin, CRP), immune function tests (e.g. cytokines like IL-1 and TNF-alpha), etc. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

In some embodiments, a structure or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a structure or pharmaceutical composition repeatedly over the life of the subject. For example, chronic treatments may involve regular administrations, for example one or more times a day, one or more times a week, or one or more times a month. In general, a suitable dose such as a daily dose of a structure described herein will be that amount of the structure that is the lowest dose effective to produce a therapeutic effect. Such an effective dose will generally depend upon the factors described above. Generally doses of the structures described herein for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms. For example, instructions and methods may include dosing regimens wherein specific doses of compositions, especially those including structures described herein having a particular size range, are administered at specific time intervals and specific doses to achieve reduction of cholesterol (or other lipids) and/or treatment of disease while reducing or avoiding adverse effects or unwanted effects.

While it is possible for a structure described herein to be administered alone, it may be administered as a pharmaceutical composition as described above. The present invention also provides any of the above-mentioned compositions useful for diagnosing, preventing, treating, or managing a disease or bodily condition packaged in kits, optionally including instructions for use of the composition. That is, the kit can include a description of use of the composition for participation in the disease or bodily condition. The kits can further include a description of use of the compositions as discussed herein. The kit also can include instructions for use of a combination of two or more compositions described herein. Instructions also may be provided for administering the composition by any suitable technique, such as orally, intravenously, or via another known route of drug delivery.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human). Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition. In some embodiments, a subject may be diagnosed with, or otherwise known to have, a disease or bodily condition associated with abnormal lipid levels, as described herein. In certain embodiments, a subject may be selected for treatment on the basis of a known disease or bodily condition in the subject. In some embodiments, a subject may be selected for treatment on the basis of a suspected disease or bodily condition in the subject. In some embodiments, the composition may be administered to prevent the development of a disease or bodily condition. However, in some embodiments, the presence of an existing disease or bodily condition may be suspected, but not yet identified, and a composition of the invention may be administered to diagnose or prevent further development of the disease or bodily condition.

A "biological sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The following examples are intended to illustrate certain embodiments of the present invention, but are not to be construed as limiting and do not exemplify the full scope of the invention.

EXAMPLES

Example 1

This example describes methods for chemically tailoring the surface of hybrid structures in the form of DNA-HDL AuNPs so as to control the ratio of surface components. The DNA-HDL AuNPs may function to both sequester cholesterol and deliver nucleic acids or regulate gene expression.

Five nm diameter citrate-stabilized Au NPs (Ted Pella) were used to template spherical synthetic HDL AuNPs using two synthetic approaches (FIGS. 2A and 2B).

HDL AuNPs were fabricated in solutions of $H_2O$/ethanol (EtOH). AuNPs, DNA, APOAI, and each of the phospholipids are soluble and stable in $H_2O$/EtOH (up to 50% EtOH). This method allows for individual surface components to be added step-wise to the HDL AuNPs, and the removal of unreacted components and EtOH.

In a typical HDL AuNP synthesis, citrate-stabilized gold nanoparticles (80 nM, 5±0.75 nm, Ted Pella, Inc.) in aqueous solution are mixed with 5-fold excess of purified human APOA1 (400 nM, Biodesign International) in a glass vial. This solution is allowed to mix overnight at room temperature while stirring. Next, a 1:1 ratio of 1,2-dipalmitoyl-sn-glycero-3-phosphoethanolamine-N-[3-(2-pyridyldithio)propionate]: 1-2-dipalmitoyl-sn-glycero-3-phosphocholine (Avanti Polar Lipids) each in 100-fold excess with respect to the concentration of AuNPs was prepared in chloroform. The phospholipid mixture is then added to the aqueous AuNP/APOA1 solution which results in a layered mixture. The mixture is vortexed and briefly sonicated which results in a pink and frothy mixture. The mixture is gradually heated to ~65° C. in order to evaporate the chloroform. After allowing the solution to cool, purification of the HDL-AuNPs is accomplished via centrifugation (15,800 g×45 min) and re-suspension in Nanopure™ water.

In the case of the first synthetic method (FIG. 2A), HDL AuNPs were fabricated as described above and increasing concentrations of 5'-cholesterylated DNA (chol-DNA) were added to the HDL AuNPs. For example, chol-DNA-HDL AuNPs were fabricated by adding a 100-fold molar excess of cholesteryl-DNA to the HDL AuNPs. All oligonucleotides were fabricated using standard phosphoramidite chemistry (Expedite 8909) and purified using reverse phase HPLC (Varian ProStar 210). The sequences used are shown in Table 1 (SEQ ID NOS: 1 through 4 from top to bottom). Following a 4-hour incubation, DNA-HDL AuNPs were distributed into 1 mL aliquots and centrifuged (15,800 g×45 min) to remove DNA not bound to the HDL AuNP surface, the supernatant decanted, and then the DNA-HDL AuNPs were re-suspended in ~30 µL of phosphate buffered saline (1×PBS, 0.15M NaCl, 0.01M phosphate buffer, pH=7.5). The aliquots were vortexed and briefly sonicated to ensure full suspension of the chol-DNA-HDL AuNP pellet. Concentrated solutions of chol-DNA-HDL AuNPs were combined to yield a final concentration of ~1 µM. Particle concentrations were measured using a UV-Vis spectrophotometer (Agilent 8453). The $\lambda_{max}$=520 nm for 5 nm AuNPs and the extinction co-efficient, $\varepsilon$=9.696×10$^6$ $M^{-1}$ $cm^{-1}$. Particles were stored at 4° C. until use.

3'-fluorophore labeled (e.g. Cyanine 3 or 5) DNA was used to quantify the amount of DNA bound to the HDL AuNP surface. Also, using the fluorescently labeled DNA, a binding isotherm was constructed to calculate the $K_d$ for cholesterol-DNA to the surface of the HDL AuNPs.

For the second synthetic method (FIG. 2B), synthesis was initiated in $H_2O$ where 5 nm AuNPs were first surface functionalized with APOAI. APOAI adsorbs to the surface of the AuNPs; however, when adding alkyl-thiol oligos, which bind tightly to the AuNP surface, ligand exchange may drive APOAI off the surface. To some degree, surface adsorption of APOAI and thiol-modified DNA can be controlled by stoichiometry. In the event that thiol-DNA loading is compromised by rapid APOAI release, primary amines on APOAI can be modified to thiol groups using Traut's reagent, which may ensure APOAI attachment while not impairing function. Traut's modification of APOAI has been used for HDL AuNPs with no appreciably differences noted in cholesterol efflux assays when compared to HDL AuNPs and natural APOAI (data not shown). The NaCl concentration was increased to near physiologic (0.15 M, slowly increasing so as not to irreversibly de-stabilize the colloid), whereupon thiol-DNA (antago-miR-210/control) was added in increasing stoichiometric amounts with reference to the AuNPs. Finally, PLs were added in ethanolic solution to functionalize remaining sites on the developing DNA-HDL AuNP surface. Final constructs were purified using centrifugation. In some cases, centrifugation may promote irreversible nanoparticle aggregation in which case either dialysis or a combination of filtration/dialysis (diafiltration) can be used for purification.

TABLE 1

| Sequence Name | Sequence |
| --- | --- |
| chol-antago-miR-210 | 5'-Cholesteryl-TEG-(A)$_{10}$-TCA GCC GCT GTC ACA CGC ACA G-3' SEQ ID NO: 1 |
| chol-antago-miR-210-Fluor (F) | 5'-Cholesteryl-TEG-(A)10-TCA GCC GCT$_F$ GTC ACA CGC ACA G-3' SEQ ID NO: 2 |
| chol-control-antago-miR | 5'-Cholesteryl-TEG-(A)$_{10}$-CCC CGT AAT CTT CAT AAT CCG AG-3' SEQ ID NO: 3 |
| chol-control-antago-miR-Fluor (F) | 5'-Cholesteryl-TEG-(A)$_{10}$ GCC TTA CGC T$_F$AC CCG GAG ACC A-3' SEQ ID NO: 4 |

Example 2

This examples shows that structures in the form of DNA-HDL AuNPs have low toxicity and can be used to regulate gene expression in cells. The DNA was electrostatically physisorbed onto a phospholipid bilayer shell of the structures.

Figure 5:
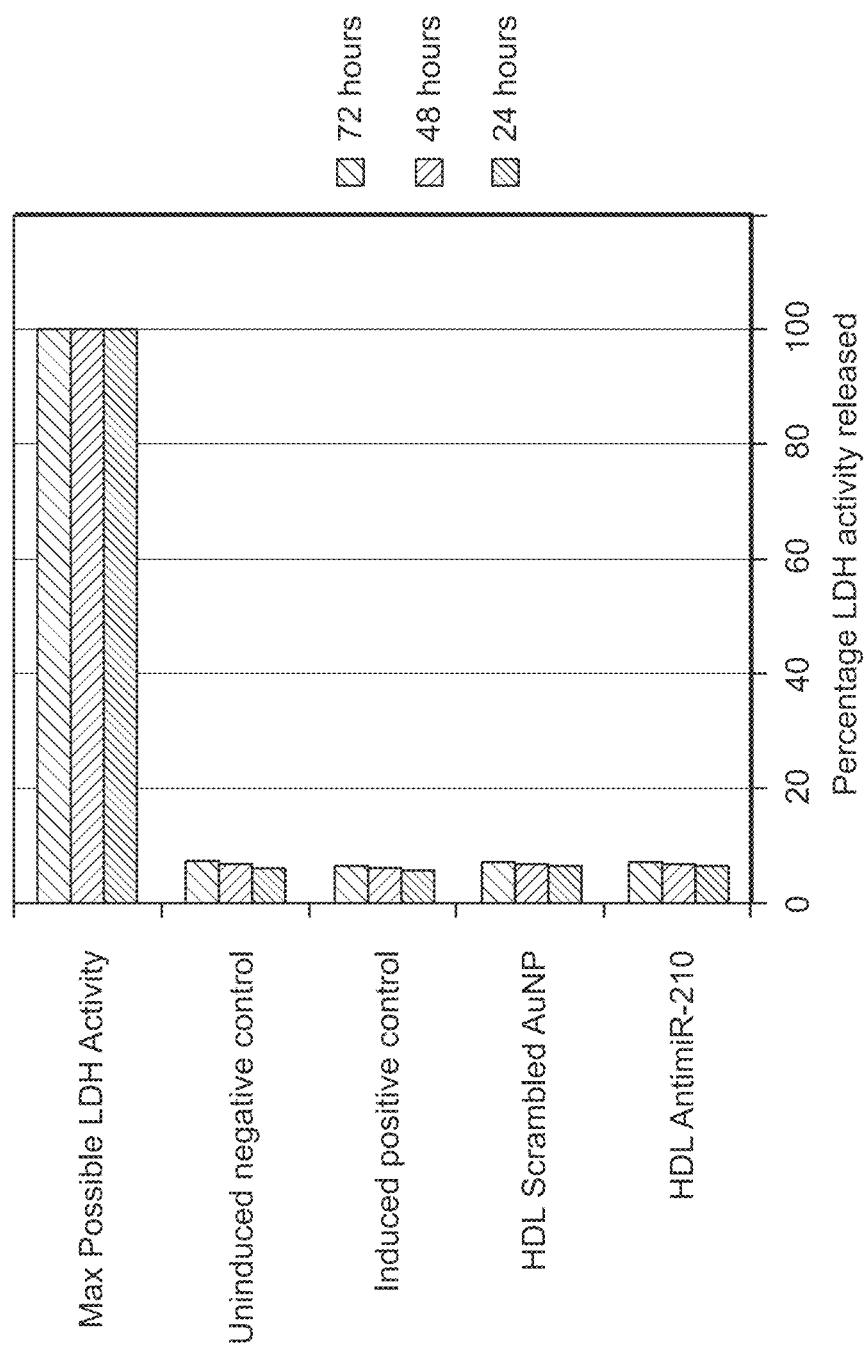
FIG. 5 shows results of toxicity experiments of structures delivered to human umbilical vein endothelial cells (HUVECs) according to one set of embodiments.
Figure 6:
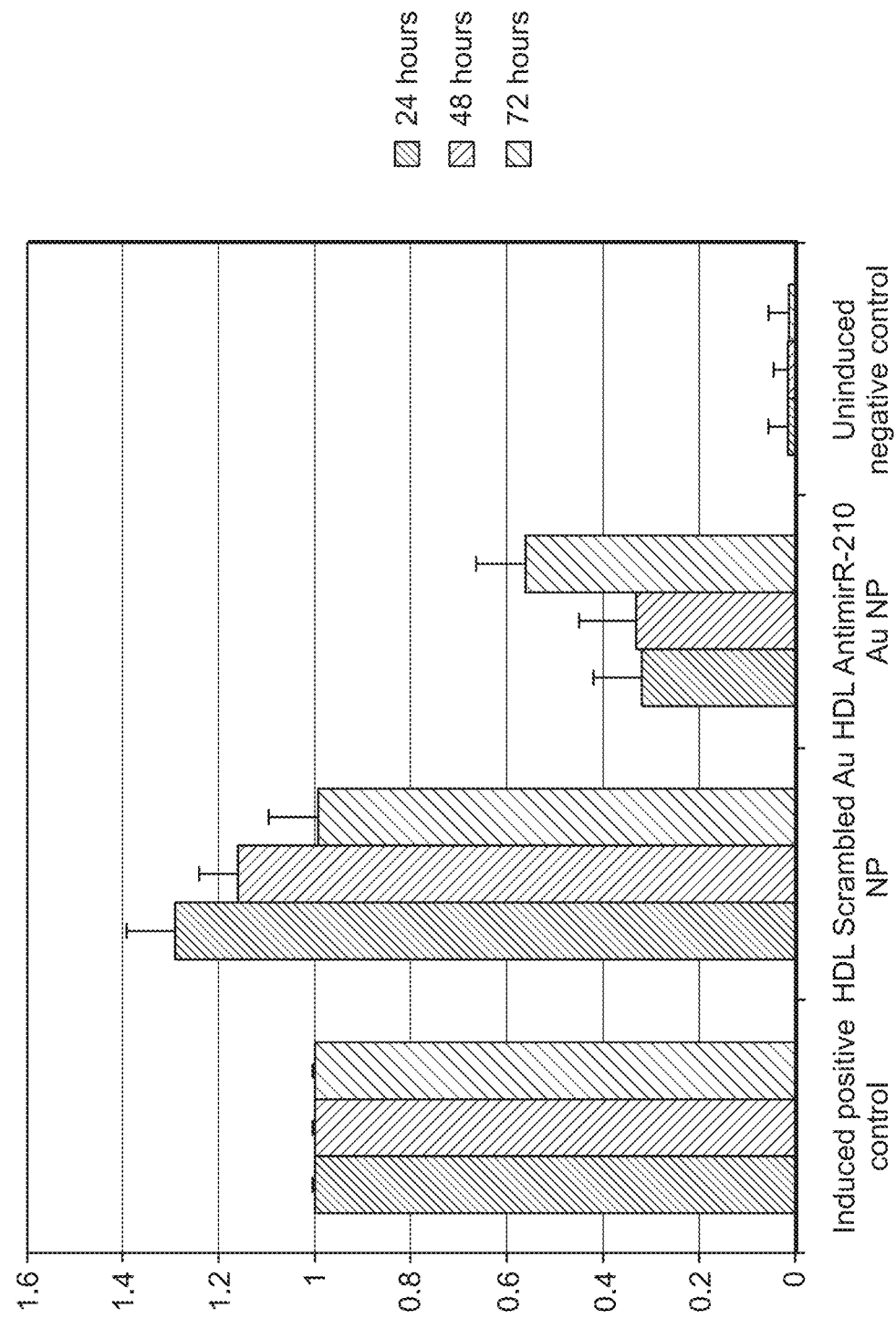
FIG. 6 shows micro RNA-210 regulation by structures in HUVECs induced to express miR-210 using $CoCl_2$ hypoxia induction according to one set of embodiments.

HDL AuNPs were fabricated using the method described in Example 1 in connection with FIG. 2A, and then mixed with DNA antago-miRs terminally modified with cholesterol. The resultant DNA-HDL AuNPs were centrifuged (×3) for purification away from unbound cholesterol-labeled DNA. The added DNAs are reverse complement "antago-miR" molecules of targeted microRNA-210. MicroRNA-210 is the pathognomic hypoxia regulated microRNA. Reducing intracellular miR-210 levels has been shown to inhibit angiogenesis in human umbilical vein endothelial cells (HUVECs), as well as induce apoptosis in cancer cell types. As HDL AuNPs naturally target endothelial cells, HUVECs were used for these experiments. Cellular hypoxia was chemically induced using cobalt chloride ($CoCl_2$), a well established mechanism for promoting HIF-1α driven expression from hypoxia response elements where miR-210 is a well-known product. DNA-HDL AuNP treatment did not cause cell toxicity as measured with a lactate dehydrogenase (LDH) assay (FIG. 5). Measured with RT-PCR following total RNA extraction from treated versus untreated cells, antago-miR-210-HDL AuNPs function to target miR-210, versus scrambled controls, and significantly reduce HUVEC miR-210 levels (FIG. 6).

Example 3

This example shows a comparison between the use of hybrid DNA-HDL-AuNP structures and DNA-AuNP structures for intracellular nucleic acid regulation.

DNA-HDL AuNPs were fabricated with either DNA antagomiR-210 oligonucleotides (SEQ ID NO: 5,5-tcagccgctgtgacacgcacag-a$_{(10)}$-SH-3) or control DNA oligonucleotides (SEQ ID NO: 6,5-ccccgtaatcttcataatccgag-a$_{(10)}$-SH-3). The control oligonucleotides do not have sequence complementarity to known expressed human RNA sequences. MiR-210 has been shown to be upregulated under hypoxic cellular conditions where it functions to regulate and calibrate the global cellular response to normoxia-hypoxia. HUVECs were studied which were chemically induced to a hypoxic state by using cobalt chloride ($CoCl_2$, 300 micromolar). Under these conditions, miR-210 levels were highly increased. Either 13 nm gold nanoparticles (AuNPs) surface functionalized with the DNA reverse complement of miR-210, known as antago-miR-210 (sequence above) according to standard procedures (Rosi et al, Science, 2006, 312, p. 1027), or HDL AuNPs co-loaded with antago-miR-210 sequences (sequence above) were fabricated. In the case of the antago-miR-210-HDL AuNPs, the DNA antago-miR-210 sequences were electrostatically physisorbed to the surface of the HDL AuNPs. In each case, the final conjugates were purified using repeated centrifugation and re-suspension in 1× phosphate buffered saline (3×, 15,000 RPM). Control DNA antago-miR was fabricated and loaded to the gold nanoparticle conjugates in a similar fashion (sequence above).

The first observation that is strikingly significant with regard to the successful cytoplasmic delivery of targeted therapeutic nucleic acids by using a hybrid DNA-HDL AuNP structure, is the direct observation that a significant number of 5 nm DNA-HDL AuNPs reside in the cytoplasmic compartment of cells. FIGS. 7A-7C are electron micrographs (EM) of a murine macrophage (J774) grown in monolayer cell culture after exposure to the DNA-HDL AuNP structures (24 hour transfection, 50 nM HDL AuNPs). The EM demonstrates 5 nm DNA-HDL AuNP structures that are free within the cytoplasmic compartment (FIGS. 7A-7B). Numerous collections of DNA-HDL AuNPs are seen in the cytoplasmic compartment of the cell (see arrow in FIG. 7A). Magnification of the arrow is shown in FIG. 7B, which demonstrates a collection of structures within (A) and outside of (B) cytoplasmic vesicles. A magnified image (FIG. 7C) of the areas indicated in A, B in FIG. 7B clearly demonstrate the structures (5 nm diameter). One can contrast a group of DNA-AuNP structures that are within an intracellular vesicle (A), versus DNA-HDL AuNP structures that are free in the cytoplasm (B). This observation led to the hypothesis that certain structures can be used successfully for regulating intracellular RNA species (e.g., endogenous microRNA (miR) or messenger RNA (mRNA)), such as HDL AuNP structures that also include a targeted nucleic acid (DNA or RNA) therapeutic (e.g. antago-miR, siRNA, miR, etc).

Figure 8A:
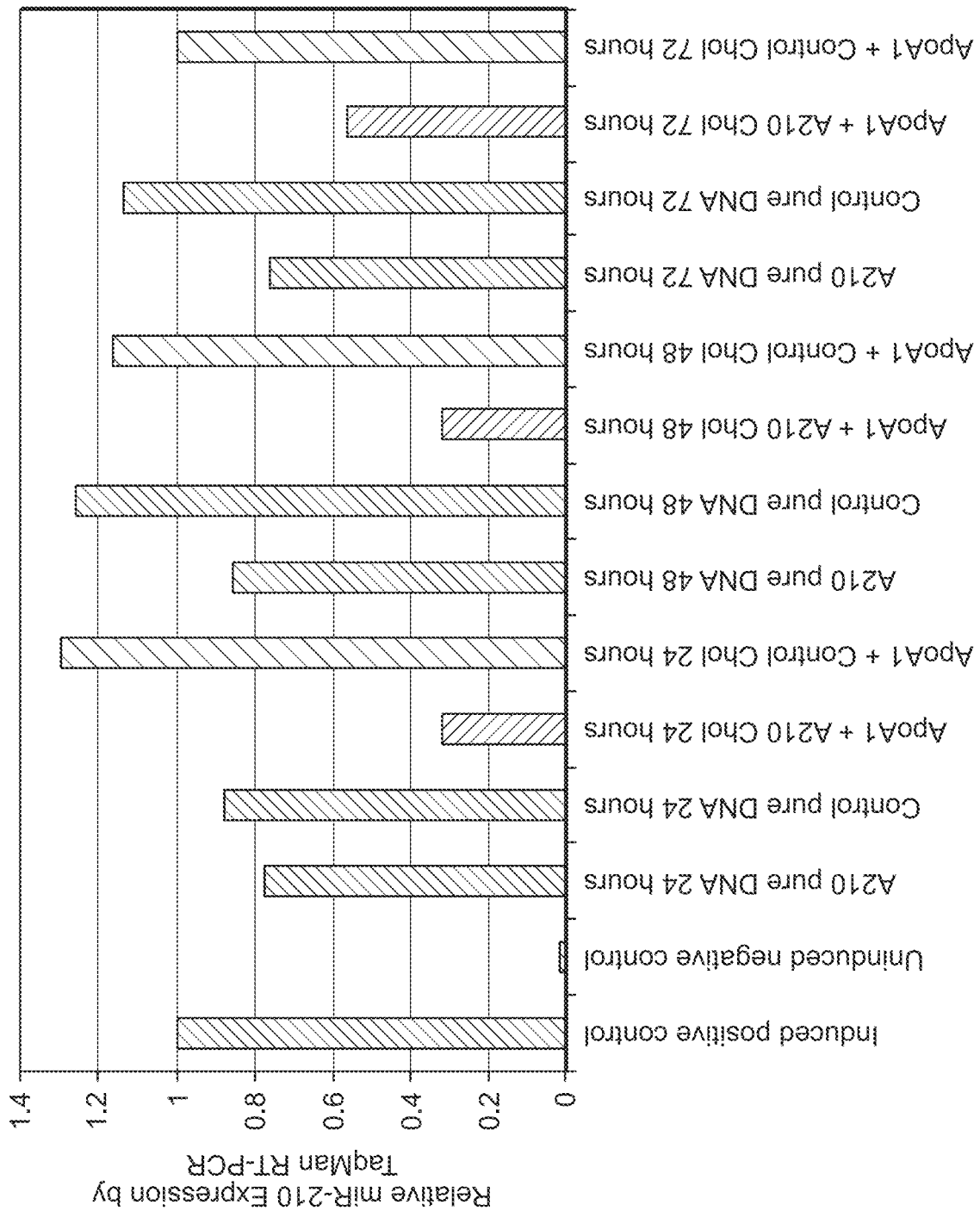
FIG. 8A shows relative expression of miR-210 levels in HUVECs according to one set of embodiments.

The ability of different structures to downregulate intracellular miR-210 levels upon transfection to the cells under $CoCl_2$ induction of miR-210 was compared. miR-210 levels were first normalized against endogenous GAPDH, and then versus miR-210 in the HUVEC cells induced with $CoCl_2$, but not treated with AuNPs. As shown in FIG. 8A, $CoCl_2$ effectively increases miR-210 expression in HUVEC cells versus those not exposed to $CoCl_2$. Cells exposed to antago-miR-210 HDL AuNPs (APOA1, 50 nM) demonstrate a significant knockdown of miR-210 levels at 24, 48, and 72 hours. At 72 hours, it appeared that the cells are beginning to recover. The antago-miR-control HDL AuNPs demonstrate no decrease in miR-210 expression. As a means of comparison, 13 nm AuNPs fabricated with surface-bound antagomiR-210 and control sequences. Transfection of these structures (1 nM) resulted in modest knockdown of miR-210, while the control demonstrated limited knockdown, as expected. Taken together, these data demonstrate that nucleic acids, in this case DNA antagomiRs to miR-210, carried in the context of the HDL AuNPs (surface physisorbed in this case) can effectively target and regulate intracellular nucleic acid species (e.g., miR-210). The control particles show minimal off-target, non-specific activity in the context of miR-210 expression.

Figure 8B:
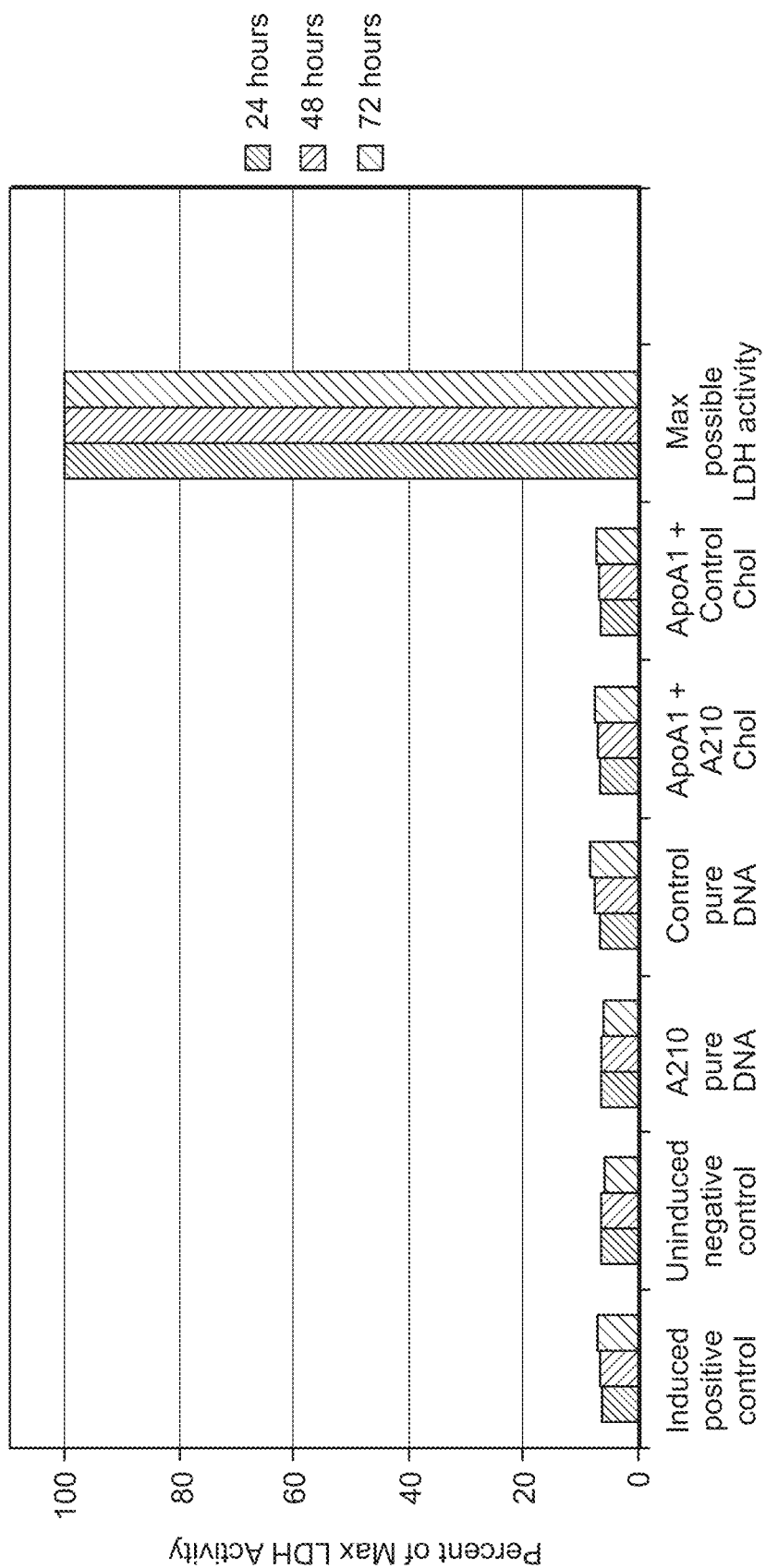
FIG. 8B shows LDH toxicity toward HUVECs according to one set of embodiments.

Data also demonstrates that transfection of antago-miR-210-HDL AuNPs are non-toxic. This was determined by assaying the cellular release of lactate dehydrogenase (LDH), a marker of plasma membrane disruption. In the case of loss of cellular plasma membrane integrity, the cytoplasmic enzyme lactate dehydrogenase (LDH) leaked into the cell culture medium. Using a colorimetric assay for LDH, differences between HUVEC cells treated with antago-miR-210 AuNPs (13 nm diameter), previously demonstrated to be non-toxic to cultured cells (Massich, et al, Mol Pharm, 6(6), p. 1934, 2009), and antago-miR-210/control HDL-AuNPs were assessed. FIG. 8B shows LDH toxicity toward HUVEC cells. The maximum possibile LDH activity (lysed cells) is demonstrated on the far right. As shown, $CoCl_2$ induced and non-induced cells show little LDH leak into the media consistent with minimal plasma-membrane disruption at baseline. Cells treated with either antago-miR-210/control AuNPs (13 nm, 1 nM) or the antago-miR-210/control HDL AuNPs (5 nm, 50 nM) demonstrate no increase in cell toxicity over baseline.

Figure 8C:
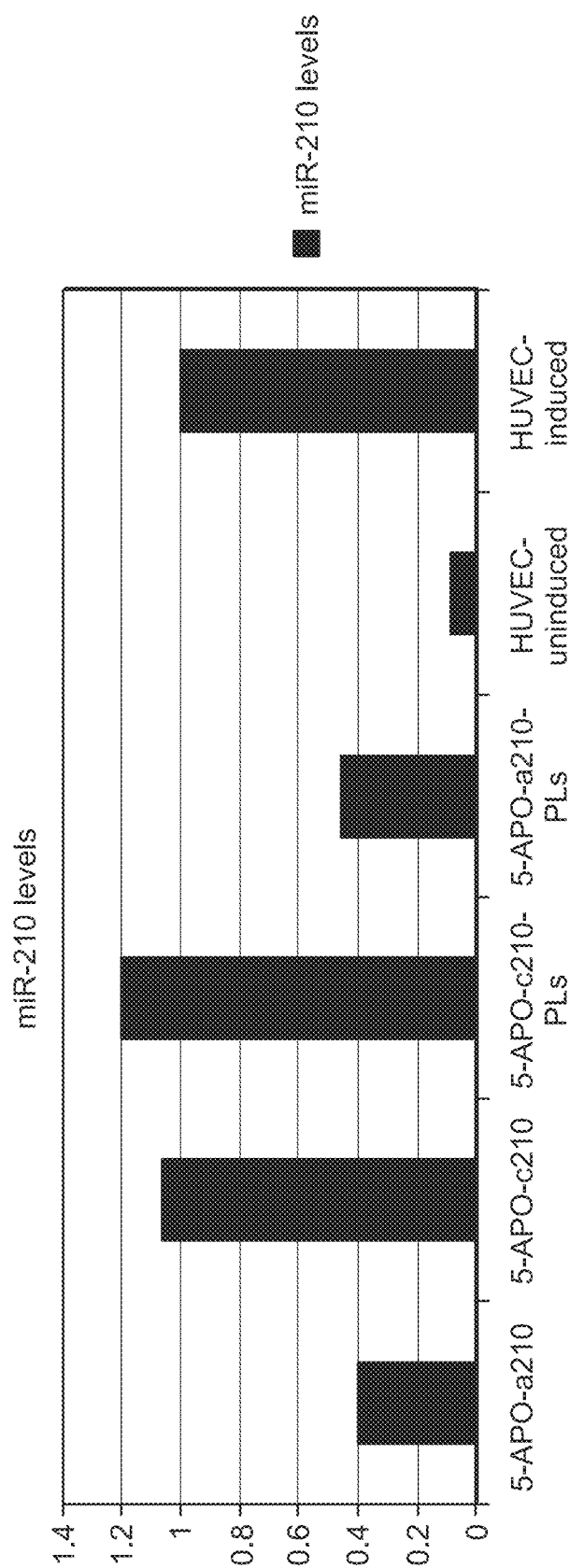
FIG. 8C shows miR-210 knock down in HUVECs using structures described herein according to one set of embodiments.
Figure 9E:
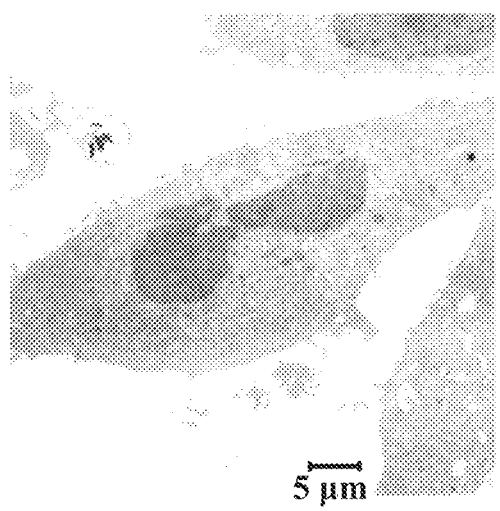
FIGS. 9E-9H are transmission electron microscopy (TEM) images showing cellular distribution of structures described herein in PC3 cells.
Figure 9F:
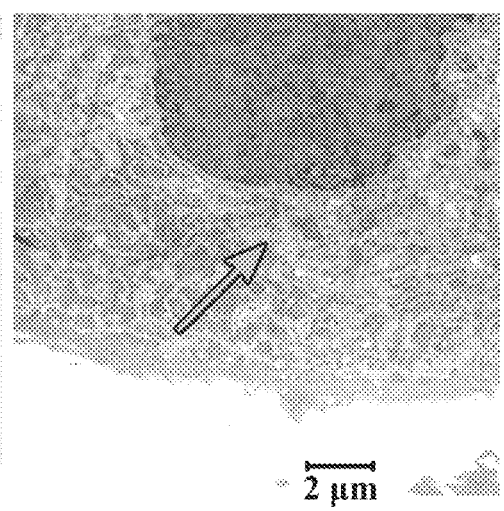
Figure 9G:
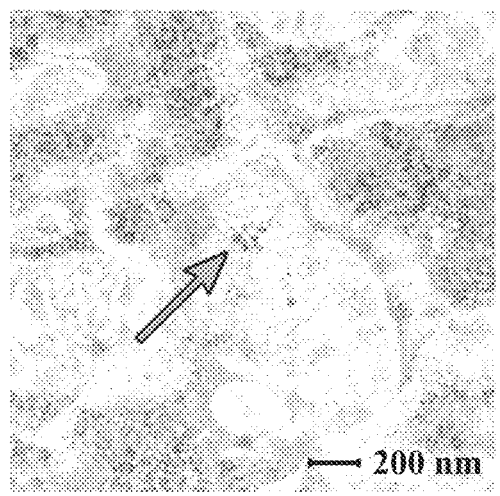
Figure 9H:
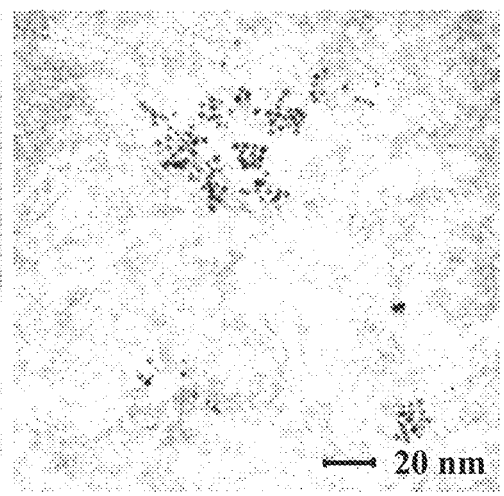

Furthermore, it was demonstrated (FIG. 8C), that a second set of structures effectively targeted and downregulated miR-210 in HUVEC cells. These structures were fabricated similarly to those above, however, they have covalently coupled (vs. adsorbed) DNA antago-miRs to miR-210 or control oligos. As shown in FIG. 8C, miR-210 regulation is efficiently achieved using structures with or without phospholipids (PLs), that target miR-210 (a210) in HUVEC cells. In all cases, a 5 nm AuNP serves as the templating nanostructure core material, and in all cases Apolipoprotein A-I (APOAI) is present on the surface of the constructs.

Specifically, FIG. 8C shows miR-210 knockdown in HUVECs using structures where the antagomiR to microRNA-210 is end-modified with a thiol for adsorption to the surface of the 5 nm AuNP at the core of the HDL AuNP. As shown, the positive control (HUVEC-induced) HUVEC cells induced with $CoCl_2$ demonstrate strong miR-210 expression as compared to the HUVEC-uninduced. Two sets of particles were fabricated and transfected into $CoCl_2$ induced HUVEC cells. The first two bars demonstrate 5 nm AuNPs with APOAI protein and bound antagomiR-DNA to miR-210 (5-APO-a210) versus the same construct but with non-targeted control DNA (5-APO-c210). In the case of the targeted agent, miR-210 is reduced approximately 60%. Bars 3 and 4 represent another set of constructs, similar to the first two, however each also contain the phospholipid bilayer used for the standards HDL AuNPs. As shown, 5-APO-a210-PLs, targeted to knockdown miR-210, do so to the tune of about 60%. The control particles (5-APO-c210-PLs) do not demonstrate miR-210 knockdown.

Overall, these data show cytoplasmic localization of HDL AuNPs, effective delivery of antago-miR-210 for regulating intracellular miR-210 expression by the antago-miR-210 HDL AuNPs, and lack of toxicity of the antago-miR-210 HDL AuNPs.

Example 4

This example shows the use of structures such as hybrid chol-DNA-HDL AuNPs as cellular delivery vehicles for nucleic acids.

High density lipoproteins avidly target cancer cells which over-express HDL receptors. The general need for cholesterol uptake by cancer cells has stimulated interest in using recombinant lipoproteins, especially recombinant HDL, engineered for targeted therapeutic delivery. Advanced prostate cancer cells that proliferate in vivo despite systemic androgen ablation appear androgen insensitive; however, data demonstrate they acquire the capacity to uptake cholesterol from HDL and endogenously produce testosterone to maintain growth. Thus, prostate cancer represents a unique case where the dual need for cholesterol for both membrane integrity and testosterone production provides an ideal model in which to test gene delivery strategies leveraging an HDL biomimetic.

HDL AuNPs tightly bind the fluorescent cholesterol analogue, 25-[N-[(7-nitro-2-1,3-benzoxadiazol-4-yl)methyl] amino]-27-norcholesterol (NBD-cholesterol) ($K_d$=3.8 nM). HDL AuNPs may have ~3 copies of apolipoprotein A-I (APOAI) on their surface and have an outer leaflet monolayer of zwitterionic dipalmitoyl-phosphatidylcholine (DPPC). Due to the tight binding of NBD-cholesterol by biomimetic HDL AuNPs, the known electrostatic complexation of nucleic acids with phosphocholine containing phospholipids, and data supporting spontaneous association and effective cellular delivery of cholesterylated nucleic acids by natural HDL species, we hypothesized that hybrid HDL AuNPs with adsorbed cholesteryl-DNA species (chol-DNA-HDL AuNPs) could be synthesized de novo for cellular nucleic acid delivery.

Biomimetic HDL nanostructures that closely mimics the size, shape, and surface chemistry of naturally occurring mature spherical HDL were fabricated with surface-immobilized cholesteryl-conjugated DNA sequences using the method described in Example 1 and according to the steps shown in FIG. 3. Briefly, an aqueous solution of colloidal gold nanoparticles (AuNPs, 5+/−0.15 nm) was mixed with apolipoprotein A-I (APOAI). A mixture of phospholipids was then added to the surface of the AuNPs to form biomimetic HDL AuNPs. The HDL AuNPs are purified by centrifugation and re-suspension in water. The cholesterylated reverse complement DNA "antagomiR" to microRNA-210 (miR-210) and control scrambled DNA were chosen for this experiment. The HDL AuNPs described above were incubated with cholesteryl-DNA oligos (100:1, chol-DNA:AuNPs) in Nanopure™ water. Following a 4-hour incubation, chol-DNA-HDL AuNPs were pelleted (15,800 g, 45 min), and re-suspended in phosphate buffered saline (1×PBS, 0.15M NaCl, 0.01M phosphate buffer, pH=7.5) to remove nucleic acids not bound to the HDL AuNP surface. FIG. 3 shows transmission electron micrographs of an individual 5 nm AuNP and chol-DNA-HDL AuNP.

Dynamic light scattering was used to assess the size increase of the structures at each step of the synthetic process. As expected, the hydrodynamic diameter of the structures increased upon APOAI addition (9±1 nm), HDL AuNP formation (10±1 nm), and cholesterylated nucleic acid addition (11±1 nm) (Table 2). UV-Vis spectroscopy confirms the stability of the DNA-HDL AuNP structures in buffered saline. A surface plasmon band centered at ~520 nm, consistent with disperse rather than aggregated AuNPs, (ref this) demonstrates conjugate stability following surface functionalization (Table 2). Furthermore, for the chol-DNA-HDL AuNPs, a strong absorption band at 260 nm which is consistent with DNA on the conjugate surface.

TABLE 2

|  | AuNP | APOAI-AuNP | HDL AuNP | Chol-DNA-HDL AuNP |
|---|---|---|---|---|
| Size (nm) | 6 ± 2 | 9 ± 1 | 10 ± 1 | 11 ± 1 |
| UV-Vis λmax (nm) | 523 | 522 | 524 | 524 |
| APOAI:AuNP Molar ratio | N/A | 3 ± 0 | 2 ± 0 | 2 ± 1 |
| Chol-DNA:AuNP Molar ratio | N/A | N/A | N/A | 13 ± 1 |

The number of oligonucleotides on the surface of chol-DNA-HDL AuNPs was quantified using fluorescently labeled oligonucleotides and found to be ~13 per structure. Finally, fluorophore-labeled apolipoprotein A-I (APOAI) was used to fabricate HDL AuNPs and chol-DNA-HDL AuNPs in order to quantify the number of APOAI molecules bound to the surface. Data demonstrate that there were ~2 copies of APOAI on the surface of the chol-DNA HDL AuNPs and that APOAI remained bound to the structure surface in the presence of chol-DNA.

Translation of mRNA is a cytoplasmic process heavily regulated by endogenous microRNAs (miRs). Effective regulation of cytoplasmic RNAs with short nucleic acids requires avoidance of endosomal sequestration. The cellular uptake of chol-DNA-HDL AuNPs, sub-cellular localization, and an assessment of cellular cytotoxicity was performed as described above. By using chol-DNA-HDL AuNPs with fluorophore labeled oligonucleotides, confocal fluorescent light microscopy revealed that the constructs associate with and rapidly enter PC3 cells (FIGS. 9A-9D).

FIGS. 9A-9D are fluorescent confocal microscopy images and FIGS. 9E-9H are transmission electron microscopy images showing cellular distribution of chol-DNA-HDL AuNPs in PC3 cells. For both confocal and TEM experiments, chemical hypoxia was induced in PC3 cells with 300 µM cobalt chloride (CoCl$_2$) for 12 hours prior to chol-DNA-HDL AuNP treatment (50 nM, final). Left. Chol-DNA-HDL AuNPs fabricated with fluor-labelled DNA ("AuNP") were incubated with cells and imaged at various time points. Keratin and nuclei ("Hoescht") were stained after cellular fixation. Images were taken after 4 (FIG. 9A), 8 (FIG. 9B), 12 (FIG. 9C), and 24 (FIG. 9D) hour incubations with chol-DNA-HDL AuNPs. For electron microscopy images were obtained after 16 hour chol-DNA-HDL AuNP transfection. Arrows indicate AuNPs in the cytoplasm of the PC3 cell. Magnifications: (FIG. 9E) 890×, (FIG. 9F) 2900×, (FIG. 9G) 6800×, (FIG. 9H) 98000×.

Figure 10:
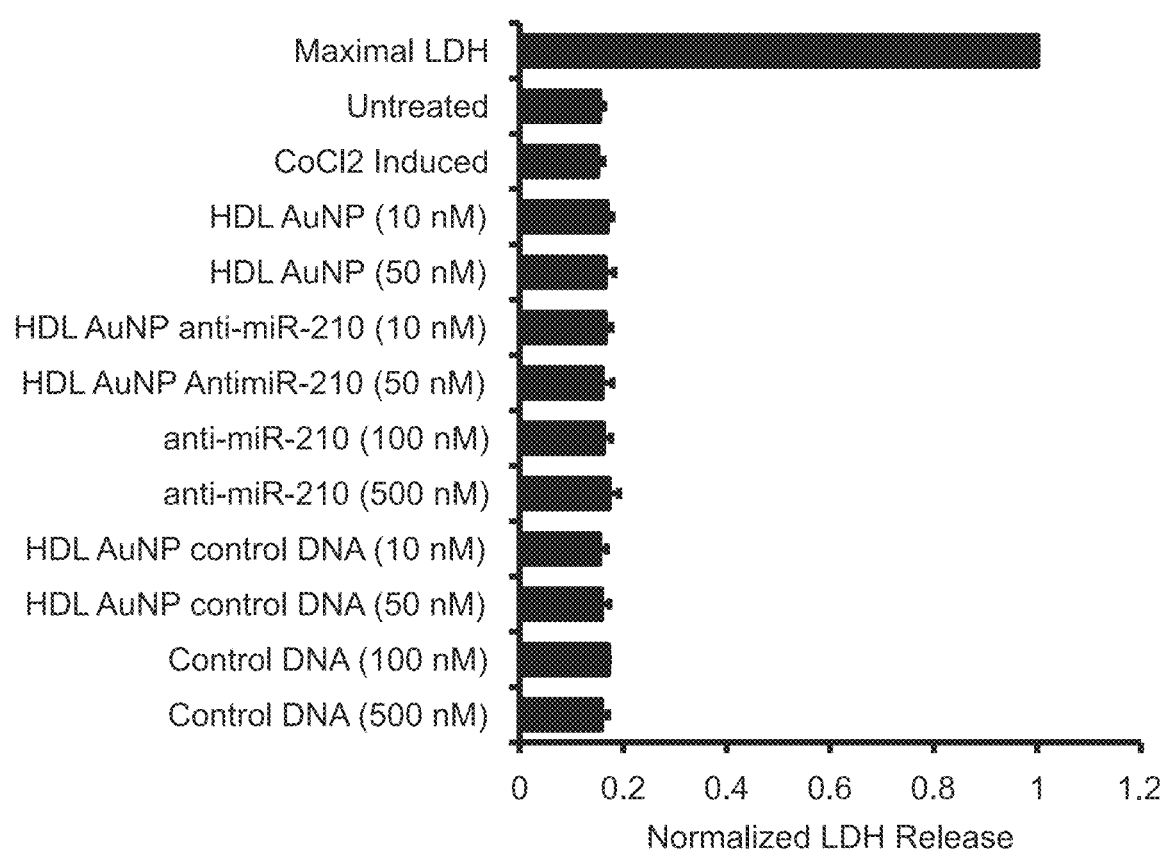
FIG. 10 shows toxicity data for various structures described herein according to one set of embodiments.

At ~4 hours, the fluorescent signal was localized to the cell membrane, and subsequently internalized into punctuate vesicles. The fluorescent signal then appears to distribute homogeneously within the cell cytoplasm prior to being repackaged in vesicles at ~24 hours. These data support that fluor-labeled chol-DNA is present within the cell cytoplasm following chol-DNA-HDL AuNP treatment, but does not provide information regarding the cellular uptake of the AuNP component of the conjugate or its sub-cellular location. Following cell treatment with chol-DNA-HDL AuNPs (16 hrs), transmission electron microscopy (TEM) demonstrates that AuNPs are present in the cell cytoplasm and free of endosomal sequestration (FIGS. 9E-9H). This is a significant finding which, without being bound by any theory, may be due to the ensemble properties of the HDL AuNP phospholipids complexed with cholesterylated DNA, and/or presence of the amphiphilic APOAI protein, small conjugate size, and surface charge. Finally, the toxicity of the chol-DNA-HDL AuNPs was investigated by using a lactate dehydrogenase (LDH) release assay. Following treatment, there was no observed toxicity above background levels, even at chol-DNA-HDL AuNP concentrations well above that needed for target RNA regulation (FIG. 10). FIG. 10 shows that HDL AuNP treatment, DNA-HDL AuNP treatment, and DNA only treatment were not cytotoxic.

Figure 11:
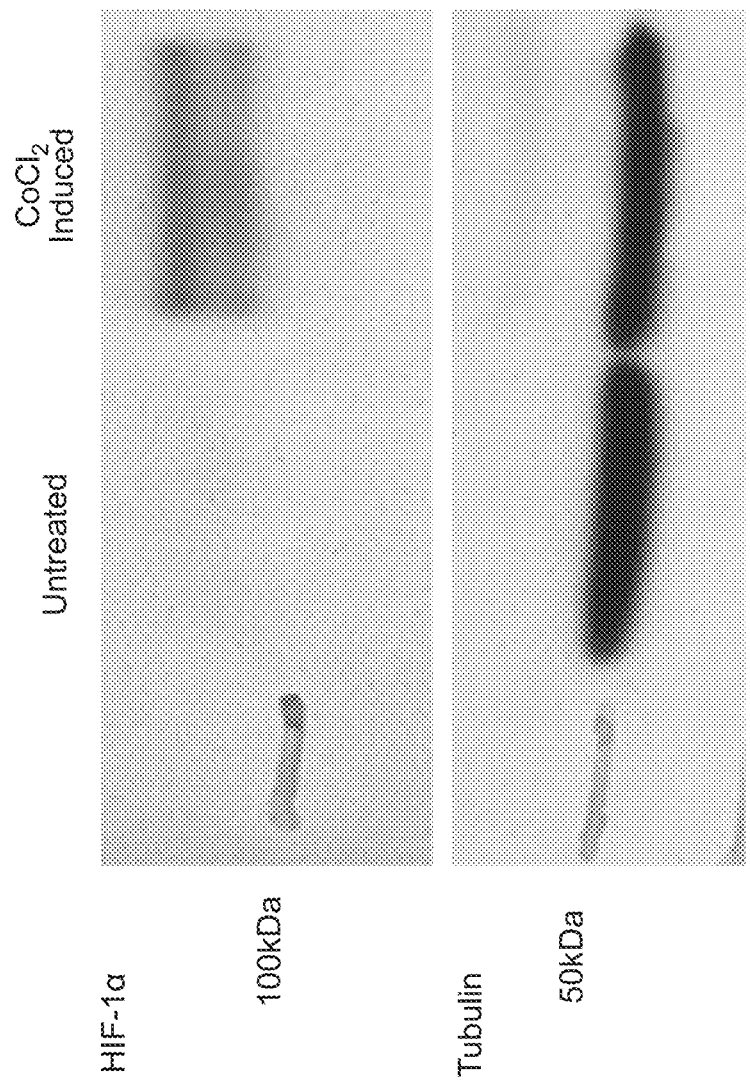
FIG. 11 shows the results of chemically inducing hypoxia in PC3 cells by exposing them to cobalt chloride according to one set of embodiments.

The ability of chol-DNA-HDL AuNPs to regulate target RNA was assessed in a cancer-relevant cell culture system: androgen insensitive human prostate cancer cells (PC3) subjected to chemical hypoxia. Cellular hypoxia is a defining feature of cancer. Hypoxia inducible factor-1 alpha (HIF-1α) is a transcription factor through which cancer cells directly respond to hypoxia. Hypoxia was chemically induced in PC3 cells by exposing them to cobalt chloride (CoCl$_2$, [300 µM]) which stabilizes HIF-1α (FIG. 11).

Stabilized HIF-1α translocates to the cell nucleus and induces transcription from hypoxia response elements (HRE) in target genes. Directly regulated by HIF-1α binding to an upstream HRE, microRNA-210 is the most well-known microRNA induced by hypoxia. The E2F transcription factor 3 (E2F3A) has been shown to be negatively regulated by miR-210, and was chosen as the protein for analysis in this model system.

Figure 12:
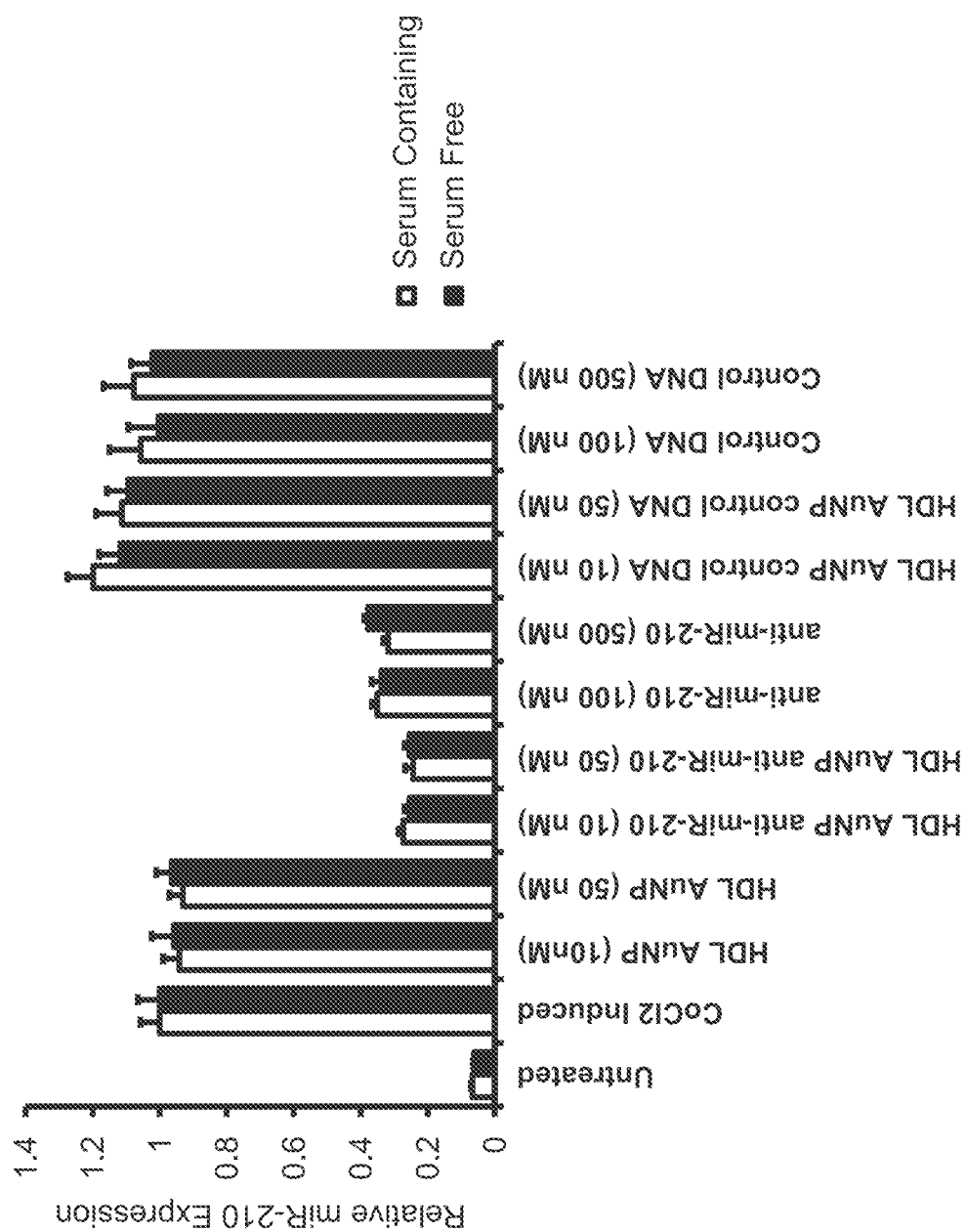
FIG. 12 shows relative miR-210 expression in PC3 cells after treatment with various structures described herein in serum-containing and serum-free media according to one set of embodiments.

In order to confirm targeted function of the chol-DNA-HDL AuNPs, real-time quantitative PCR (RT-qPCR) was performed to measure miR-210 levels in PC3 cells. U6 small nuclear RNA was used as an endogenous control. Initial cell treatments were conducted in serum-free media to avoid potentially confounding chol-DNA uptake by lipoproteins present in serum. As a means of comparison, similar experiments were conducted in serum containing media (FIG. 12).

Figure 13A:
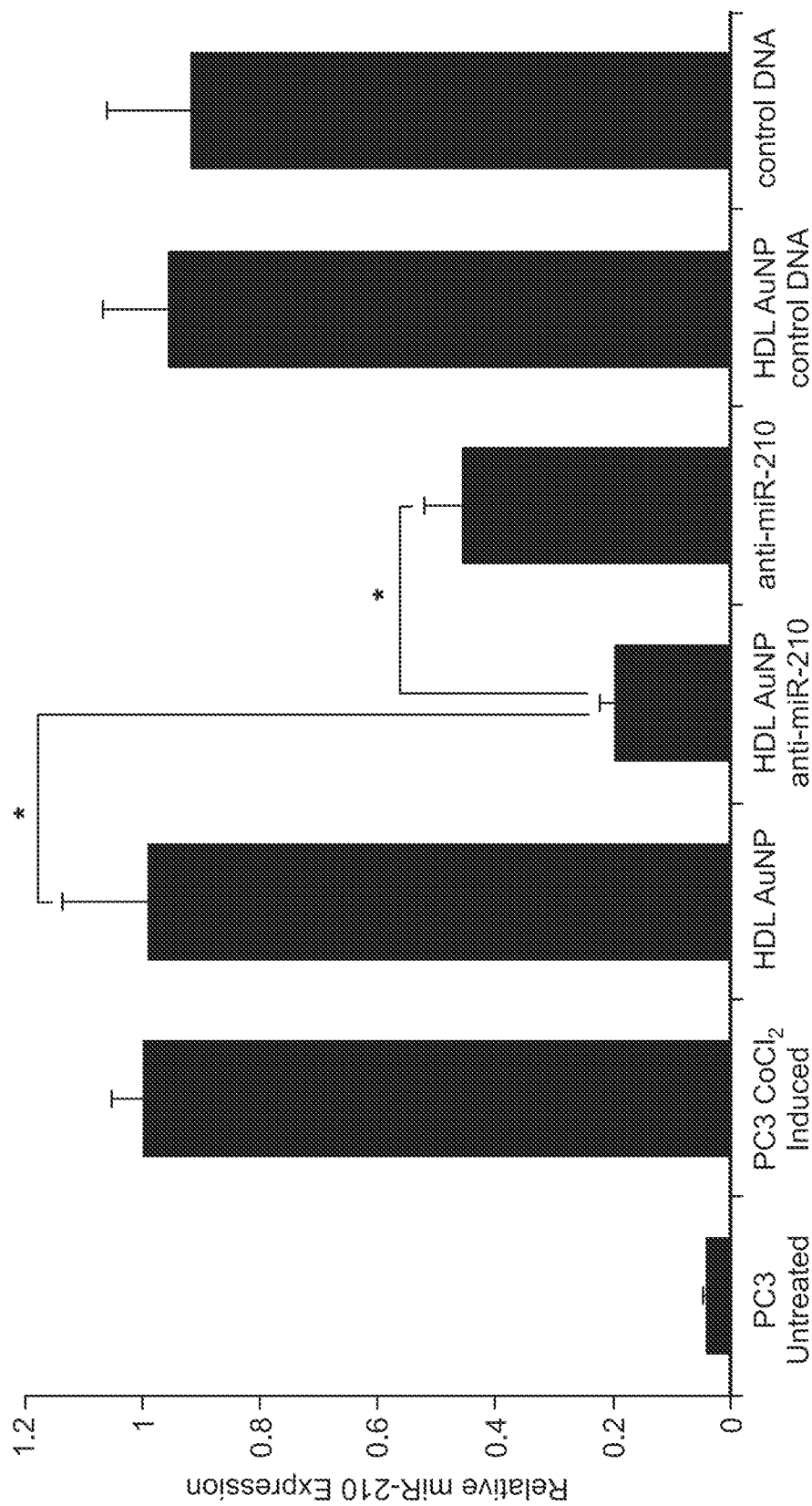
FIG. 13A shows relative miR-210 expression in PC3 cells after treatment with various structures described herein according to one set of embodiments.
Figure 14:
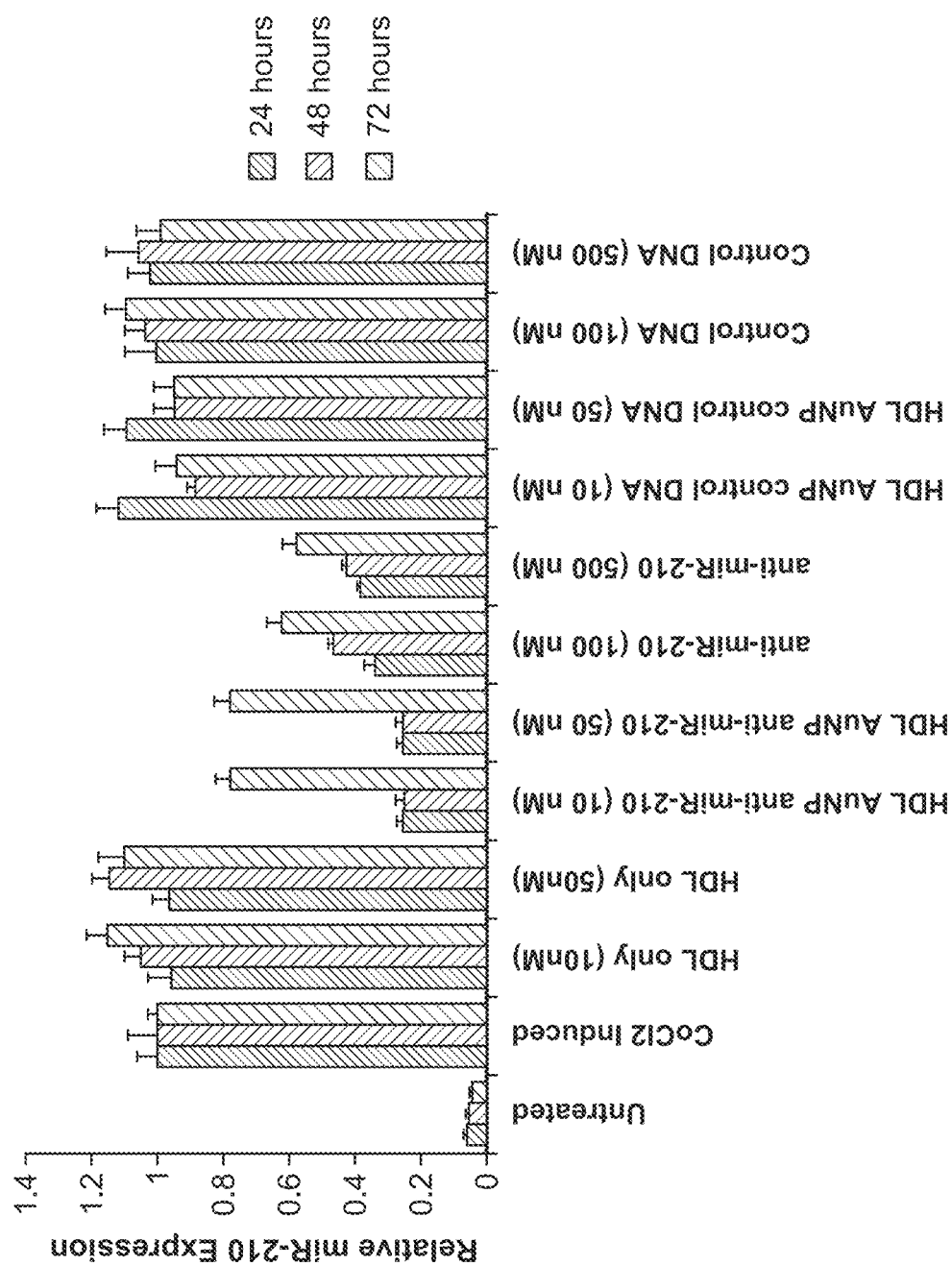
FIG. 14 shows a time course of miR-210 knockdown in PC3 cells treated with various structures described herein according to one set of embodiments.

As shown in FIG. 13A, treatment with miR-210 targeted chol-DNA-HDL AuNPs results in an 80% reduction in cellular miR-210 levels as compared to HDL-AuNP only control, and a 55% reduction as compared to free antagomiR-210. Free cholesteryl-DNA was added on an equimolar basis to the cholesteryl-DNA adsorbed to the surface of the chol-DNA-HDL AuNPs. HDL AuNPs (vehicle control), scrambled chol-DNA-HDL AuNPs, and the free scrambled chol-DNA did not appreciably change miR-210 levels (FIG. 13A). At 72 hours, it appears that the miR-210 levels begin to recover (FIG. 14).

Figure 13B:
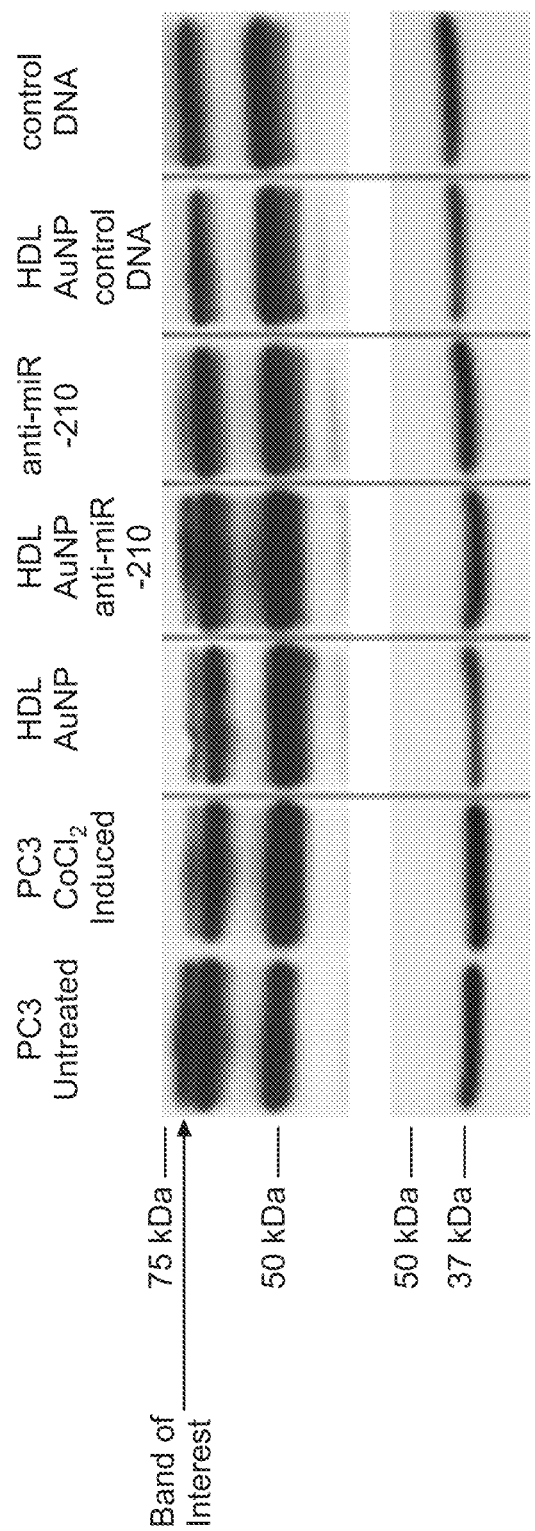
FIG. 13B shows a western blot assessment of E2F3a, a target of miR-210, showing that treatment of PC3 cells with certain structures described herein de-represses E2F3a according to one set of embodiments.

In order to verify delivery and function of antagomiR-210 at the protein level, Western blotting was performed for E2F3A following treatment with chol-DNA-HDL AuNPs. As shown in FIG. 13B, PC3 cells express E2F3A, and the level of which is repressed upon chemical hypoxia induction with CoCl$_2$, as expected. (Giannakakis, Cancer Cell Bio) Treatment of PC3 cells with 10 nM chol-DNA-HDL AuNPs surface conjugated with the anti-miR to miR-210 results in a de-repression of E2F3A expression which is superior to that of free chol-DNA anti-miR-210 added at ~10-fold molar excess. Vector only HDL AuNPs, scrambled chol-DNA HDL AuNP, and free control scrambled sequences do not result in de-repression.

FIGS. 13A and 13B show RT-PCR and Western blot assessments of chol-DNA-HDL AuNP-mediated knock-down of miR-210. (FIG. 13A) At the miR-210 level, chol-DNA-HDL AuNP antagomiR-210 treatment significantly reduces miR-210 expression in the setting of CoCl$_2$, both in comparison to HDL AuNP alone and in comparison to an equimolar dose of the free chol-antagomiR-210 (P<0.01, n=3). (FIG. 13B) Western blot of E2F3a, a target of miR-210, demonstrates that chol-DNA-HDL AuNP antagomiR-210 treatment de-represses E2F3A (top). GAPDH was used as protein control (bottom).

These data provide compelling evidence for hybrid chol-DNA-HDL AuNP structures as cellular delivery vehicles for nucleic acids. Chol-DNA-HDL AuNPs enter PC3 cells, avoid endosomal sequestration, do not demonstrate cellular toxicity, and, in this experiment, function to specifically target intracellular miR-210 and de-repress its known target, E2F3A.

The HDL AuNP platform provides significant control over the synthetic process, and the platform is general with regard to the identity of nucleic acid, lipid content, final conjugate size, and surface chemistry. Each of these factors is known to be important to nanoparticle function at the bio-nano interface. Furthermore, the biomimetic HDL AuNP platform may provide advantages with regard to systemic pharmacokinetics, cell targeting, and receptor-mediated conjugate uptake through known HDL receptors, such as scavenger receptor type B-1 (SR-B1). As such, hybrid biomimetic lipoprotein agents may find significant utility for the targeted in vivo delivery of nucleic acid therapeutics for any number of disease processes, including atherosclerosis, inflammation, and cancer.

Materials and Methods

DNA and APOAI Quantification:

To measure amount of DNA on the DNA-HDL AuNP surface oligonucleotides with fluorescent modifiers were used (Table 1; SEQ ID NOs: 1 through 4 from top to bottom). HDL-AuNPs were synthesized using the procedure described above and their concentration was determined by UV-Vis. Gold nanoparticles were oxidized with KCN (40 mM, final) in order to liberate fluorescently bound DNA and the fluorescence of the solution was measured. The number of DNA strands per particle was determined by comparing the obtained fluorescence measurements to that of a standard curve prepared with known concentrations of fluor-labeled DNA.

Quantification of the number of APOAI molecules was performed similarly using fluorescently labeled APOAI. APOAI was labeled with Alexa-488 using a commercially available protein labeling kit (Invitrogen) according to the manufacturer's instruction.

Dynamic Light Scattering/UV-Vis:

HDL-AuNPs were diluted to 10 nM concentration in water. Dynamic light scattering (DLS) measurements were performed using a Zetasizer Nano ZS (Malvern). The hydrodynamic diameter is reported according to the number function. Stability of HDL-AuNPs to aggregation in water and buffered saline solutions was measured using an Agilent 8453 UV-Vis spectrophotometer.

Cell Culture:

Prostate adenocarcinoma cells (PC3) were obtained from American Type Cell Culture (ATCC, CRL-1435) and grown in RPMI 1640 medium supplemented with 10% fetal bovine serum (FBS) and 1% penicillin streptomycin (Invitrogen, 11835-030). Cells were cultured in T75 flasks and sub-cultured into 6, 12, or 24 well plates. The cells were incubated at 37° C. in 5% $CO_2$. According to experimental protocol, cells were cultured in serum free containing medium as well as under chemically induced hypoxia. To chemically induce hypoxia, 300 µM cobalt chloride ($CoCl_2$) was added to medium at least 12 hours prior to treatment. As described herein, $CoCl_2$ treatment leads to a significant stabilization of HIF-1α and RT-qPCR data demonstrates a significant increase in miR-210 levels.

Light Microscopy:

Live cell imaging observations were made at 37° C. using a Zeiss LSM 510 confocal microscope equipped with a 63×1.4 NA objective and an airstream stage incubator (Nevtek).

Cells were grown on glass coverslips in RPMI 1640 medium supplemented with 10% FBS and 1% penicillin streptomycin. Chemical hypoxia induction in PC3 cells was initiated by adding 300 µM (final) cobalt chloride ($CoCl_2$) to the cell culture medium 12 hours prior to treatment. PC3 cells were treated with DNA-HDL AuNPs (50 nM, final) and imaged at varying time points. Prior to imaging, cell culture media was removed and the cells were washed with 1×PBS. Next, the cells were fixed in 3.7% formaldehyde (FA) in 1×PBS, and processed for immunofluorescence. The cells were stained with antibodies directed against pan-cytokeratin used at a 1:100 dilution (c-11, Sigma, c2931). Secondary antibodies were donkey anti-mouse alexa-568 used at a 1:100 dilution (Invitrogen). Hoechst was used to stain the nuclei of cells and was added along with the secondary antibody. Coverslips were placed faced down on glass slides in a mixture of 50% glycerol with 0.01 mg/mL p-phenylenediamine. Coverslips were sealed with clear nailpolish (Electron Microscopy Sciences). Slides were protected from light and stored at −20° C. prior to confocal imaging.

Electron Microscopy:

Cells: PC3 cells were cultured on Thermonex coverslips in RPMI 1640 medium supplemented with 10% fetal bovine serum and 1% penicillin streptomycin. Hypoxia was chemically induced by adding 300 µM (final) $CoCl_2$ to culture medium 12 hours prior to transfection. Cells were treated with 50 nM (final) DNA-HDL AuNPs. Following incubation with the DNA-HDL AuNPs, the cells were washed twice with 1×PBS and then immersed in 2% paraformaldehyde/ 2.5% gultaraldehyde in 0.1M sodium cacodylate buffer (SCB). The cells were then rinsed with 0.1M SCB and placed in secondary fixative containing 2% osmium tetraoxide in 0.1M SCB. Next, cells were rinsed with distilled water and stained with 3% uranyl acetate. The fixed samples were rinsed with distilled water and then dehydrated in ascending grades of ethanol. Propylene oxide was used as a transitional buffer, and tissues were embedded in Epon 812 and Araldite resin. Samples were placed in a 60° C. oven to cure. The blocks were sectioned using an ultramicrotome and then mounted on grids for TEM imaging. TEM images were obtained using a FEI Tecnai Spirit G2 operating at 120 kV.

Particles: TEM particle samples were prepared using 200 mesh carbon-film coated copper grids (Electron Microscopy Sciences). Two samples were prepared. A small aliquot of 5 nm diameter AuNPs and chol-DNA-HDL AuNPs were spotted to grids, excess was removed with filter paper, and the samples were allowed to dry. The samples were then stained with 3% uranyl acetate (15 mins) prior to imaging. TEM images were obtained using a FEI Tecnai Spirit G2 operating at 120 kV.

Cytotoxicity:

Cell cytotoxicity experiments were conducted using a commercially available enzymatic colorimetric lactate dehydrogenase (LDH) assay according to the manufacturer's protocol (Roche Applied Sciences). LDH is an intracellular enzyme that is released into the cell culture media following cell death. The old cell growth media collected at various time points for the treated as well as untreated cell pools were spun down at 300 g for 10 minutes, to remove cell debris. These supernatant of the media samples were subsequently assayed for LDH levels. To establish the maximum LDH levels, one untreated and non-hypoxia simulated cell pool was lysed by introduction of 1% Triton-X 100 into the cell growth media. Fresh PC3 cell growth media was used as a blank. Samples were twenty-fold diluted with assay medium (1% Serum in DMEM). LDH activity was measured by adding the working reagent according to the manufacturer's protocol, and the samples were incubated at room temperature for 30 mins. LDH levels were quantified spectrophotometrically.

RT-qPCR for miR-210:

PC3 cells were cultured according to the protocol above. Following treatment, the cells were lysed and total RNA was extracted using TRIzol® reagent (Invitrogen). Total RNA was quantified and its integrity assessed using the NanoDrop Technologies ND-100 spectrophotometer by measuring absorbances at 260 nm and 280 nm. Samples with $A_{260}/A_{280}$ ratio between 1.8 and 2.0 were used for analysis. Subsequently, the total RNA samples were diluted to a concentration of 2 ng/µl. Using TaqMan™ RT Kit and TaqMan™ U6-snRNA and hsa-miR-210 RT probes, 10 ng of total RNA from each sample was reverse transcribed (RT) in 15 µl total reaction volumes, as per the manufacturer's protocol. Next, RT samples were used to setup 20 µl final volume qPCR reactions, in 384 well plates using TaqMan™ PCR Master Mix and TaqMan™ U6-snRNA and hsa-miR-210 probes, as per the manufacturer's protocols. The qPCR reaction was carried out using an ABI Prism Model 7900HT. Data was analyzed using the comparative $C_t$ method using U6 small nuclear RNA as an endogenous control.

Western Blot:

PC3 cells were cultured as above until approximately 80% confluent. The cells were treated with targeted and scrambled control chol-DNA (100 and 500 nM), HDL AuNP vector (10 and 50 nM), and targeted and scrambled control chol-DNA-HDL AuNPs (10 and 50 nM). PC3 cells were exposed for 24 hours. Next, the cells were washed×2 with 1×PBS. Total cellular protein was extracted using mammalian protein extraction reagent (M-PER, Thermo) according to the manufacturer's protocol. The protein concentration from each sample was measured using Coomassie protein staining according to the Bradford assay using a bovine serum albumin (BSA) standard curve and colorimetric readout at 570 nm (BioRad). The total protein concentrations from each sample were made equivalent (20 µg), mixed with loading buffer, and then subjected to electrophoretic separation. A 4-20% Tris-HCL Criterion polyacrylamide gel was used for separation (200V, ~1 hour). The gel was transferred to a nitrocellulose membrane overnight at 4° C. Following transfer, the membrane was washed in water (5 min) and then allowed to dry for ~1 hour. The membrane was re-wetted in methanol and then transferred to Ponceau stain×5 mins. Following a brief rinse, the membrane was imaged (Epson scanner). Prior to immunoblotting, the membrane was washed in TBST (Tween=0.1%)×20 mins. Blocking of the membrane was then completed using 5% milk/TBST for 1 hour. The primary E2F3A antibody (polyclonal, rabbit, C-18 Santa Cruz[3], 1:200) was added and allowed to incubate overnight at 4° C. The membrane is then washed for 10 minutes in TBST×3. The secondary antibody (goat anti-rabbit IgG, HRP-conjugate, 1:10,000, Jackson ImmunoResearch) is then added in 5% milk/TBST and allowed to incubate×1 hour at room temperature (RT). Finally, the membrane was developed with ECL Plus (GE Healthcare) colorimetric reagent for 5 mins at RT. The membrane was then imaged. GAPDH was used as a control. GAPDH immunoblotting was performed similarly to E2F3A. The GAPDH antibody (mouse, 1:20,000) is HRP-conjugated (Sigma), and was allowed to incubate for 1 hour at RT.

Example 5

This prophetic example shows methods that can be used to release nucleic acids from structures described herein. In particular, nucleic acid-HDL AuNPs with a modular nucleic acid component may be used for controlling the release of nucleic acid from the AuNP surface by various stimuli such as, for example, ex vivo (e.g. light), physiologic (e.g. reducing intracellular environment), or pathologic (e.g. reactive oxygen species or low pH) triggers.

DNA-HDL AuNP structures may be fabricated using Au—S coupling of DNA oligonucleotides to the surface of a Au nanostructure core such that the structure effectively sequesters the gene regulating portion of the DNA sequence on the surface of the structure, and fail to make it available to the intracellular cytoplasmic machinery required to regulate gene expression. Engineering nucleic acid triggered release mechanisms into the DNA-HDL AuNP platform provides a way to test the mechanism of action of the DNA-HDL AuNP structures once inside cells, compare materials with different release chemistries, and introduce flexibility into the platform to address bio-nano interfacial challenges (e.g. endosomal sequestration) that may surface after initial testing.

Figure 15:
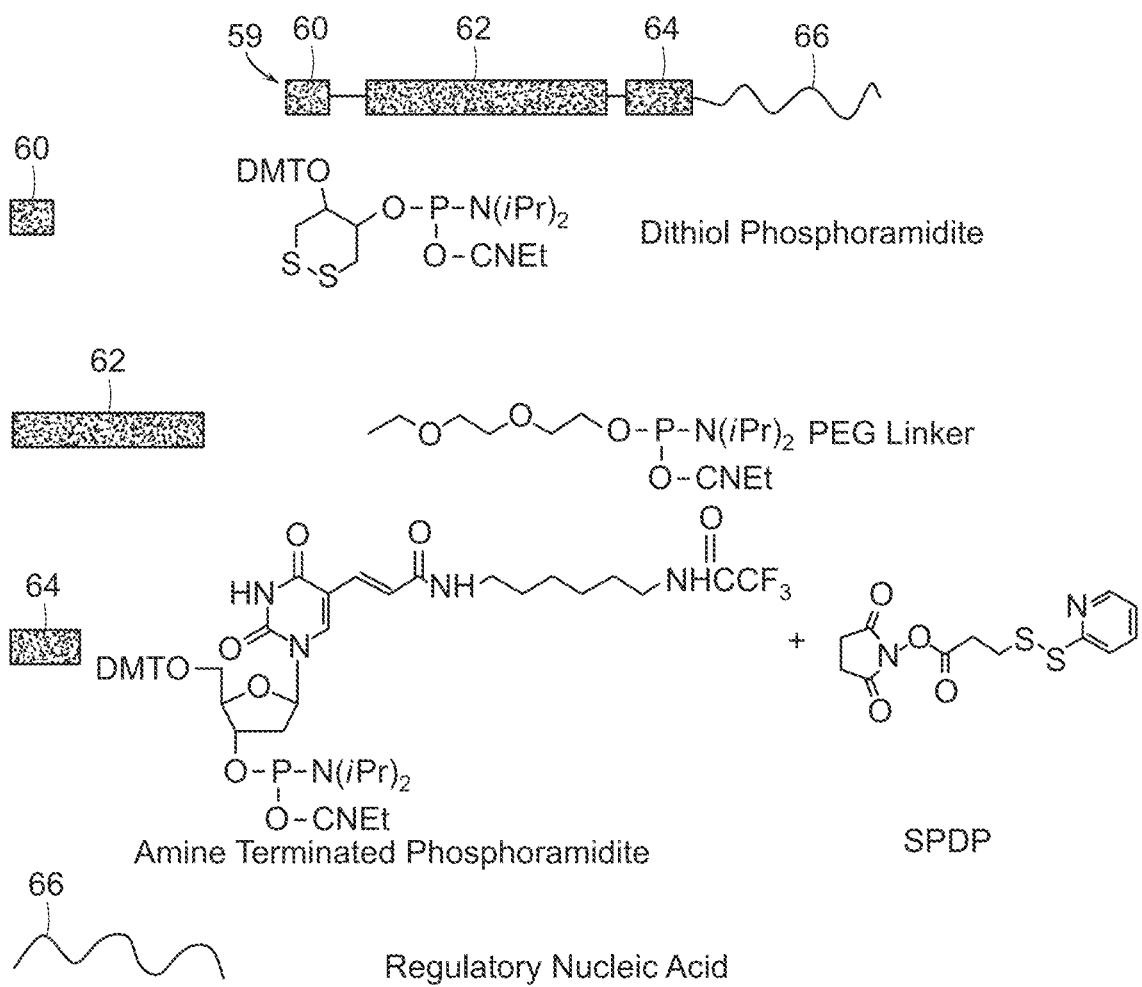
FIG. 15 shows examples of components that can be used to allow release of nucleic acids from structures described herein according to one set of embodiments.

In one set of embodiments, DNA-HDL AuNP structures fabricated under this objective will proceed according to FIG. 2B and FIG. 15. As shown in FIG. 15, functionalized oligonucleotides, represented by component 59, can be fabricated to include, for example, four distinct units 60, 62, 64 and 66. In one set of embodiments, block 60 is an end-modification that can allow component 59 to attach to a portion of a structure (e.g., a shell or a nanostructure core). Block 62 is a linker that may attach block 60 to a release linker, represented by block 64. The release linker may allow the coupling and release of a regulatory nucleic acid 66 from component 59. Examples of specific chemical compounds that can be used for each of units 60, 62, 64 and 66 are shown in FIG. 15. PEG=polyethyleneglycol and SPDP=N-succinimidyl-3-(2-pyridyldithio)propionate.

Solid-phase phosphoramidite chemistry is an example of a method that can be used to fabricate functionalized oligonucleotides. Directed manipulation of each block will be conducted in order to determine how each changes nucleic acid release and, ultimately, in vitro function. First, 3'-thiol end modifications (block 60) can be manipulated in order to drive the attachment and loading of DNA to the AuNP surface. Manipulation of the 3'-thiol moiety, for example, may be used to optimize the loading of all DNA-HDL AuNP surface components. Next, and showing the example of intracellular reduction and disulfide ligand exchange as the method of nucleic acid release, a release linker, block 64, will be systematically varied, including removed, in order to test, specifically, how the chemical identity of the linker impacts nucleic acid release. In the case of a disulfide, glutathione mediated ligand exchange and nucleic acid release will be studied in solution in order to systematically assess how the tether impacts release form the surface of DNA-HDL AuNPs. Next, different tethers (block 62), including none, will be added between the thiol (block 60) and linking (block 64) elements in order to assess how tether length changes nucleic acid release. There are a number of thiol, tether, and linking chemistries directly compatible with phosphoramidite chemistry and solid phase synthesis, and others that can be manually added using straight-forward conjugation chemistries (e.g. EDC/NHS). FIG. 15 demonstrates some common phosphoramidites and combinatorial cross-linking strategies.

Finally, the regulatory nucleic acid represents the unit 66. For these experiments, single-stranded DNA will be focused on due to the broad potential applications of DNA introduced into cells and due to its stability. The DNA antago-miR-210 and scrambled sequences will be studied, although other oligonucleotides such as those described herein can be used. In each case, straight-forward assessment of nucleic acid release will take place in solution using appropriate chemical gradients (e.g. pH or glutathione titration) or light. DNA stability may be enhanced by binding to the surface of the AuNP. While nucleic acid stability on AuNPs is related to density, the HDL AuNP platform may provide advantages by sequestering the nucleic acid within the phospholipid layer, and preventing access by nucleases. This may well depend upon other properties of the attached oligo including tether length. By using standard fluorescence assays and melting transition assays, both the stability and recognition properties of the immobilized DNA oligonucleotide will be measured.

Example 6

This example describes a structure with a shell having a mixed monolayer configuration to allow for covalent bonding of therapeutic oligonucleotides to the core of the structure.

A mixed monolayer structure may allow for covalent bonding of therapeutic oligonucleotides to the nanostructure core via a linking element, in this case the carboxylic acid group of mercaptohexadecanoic acid (MHA). By integrating MHA with phospholipids, t nucleic acid sequences can be conjugated to nanoparticles and, in some cases, may overcome endosomal sequestration. 1-Ethyl-3-[3-dimethylaminopropyl]carbodiimide hydrochloride and N-hydroxysulfosuccinimide (EDC/NHS) chemistry is a well-established method of activating carboxylic groups to increase their reactivity toward primary amines, thus generating a stable amide bond. Here, EDC/NHS was used to facilitate amide bond formation between the carboxylic acid group of MHA and an oligonucleotide end-modified with a primary amine.

The use of short nucleic acid sequences to selectively bind to mRNA sequences within cells is a well established method of gene regulation. In this example, a DNA sequence shown to regulate the expression of survivin, an anti-apoptotic protein near universally upregulated in human cancer, was chosen as the model nucleic acid therapeutic. Mixed monolayer AuNPs covalently coupled to anti-survivin oligonucleotides have the potential to selectively bind intracellular survivin mRNA, knockdown survivin protein expression, and induce cancer cell death.

Materials and Methods

Synthesis of a Mixed-Monolayer Nanoparticle of Phospholipids and MHA:

The schematic for the synthesis of the mixed-monolayer AuNP is shown in FIG. 4. Thiol modified phospholipids, 1,2-bis(11-mercaptoundecanoyl)-sn-glycero-3-phosphocholine (C10) and 1,2-bis(16-mercaptohexadecanoyl)-sn-glycero-3-phosphocholine (C15), and mercaptohexadecanoic acid (MHA) were adsorbed onto the surface of 10 nm AuNPs. In a typical synthesis, 10 nm AuNPs were suspended in a 1:1 mixture of ethanol and water and mixed with a 100-fold excess of appropriate lipids. Solutions of lipids and AuNPs were mixed overnight. Unreacted lipids were removed from solutions of conjugated lipid-AuNPs using dialysis [10 kD molecular weight cut off (MWCO), Snake-Skin dialysis tubing (Thermo Scientific)]. Various ratios of lipid (C10 or C15) to MHA were employed in order to optimize coupling of oligonucleotides to the nanostructure core surface.

Nanostructure Characterization:

Dynamic light scattering (DLS, Malvern) measurements were used to confirm chemical functionalization of the AuNPs by demonstrating an increase in hydrodynamic diameter. Transmission electron microscopy (TEM, FEI Spirit) was used to image the lipid layer on the surface of the AuNPs. The lipid layer was identified using uranyl acetate staining. Finally, the use of sodium bicarbonate was used to qualitatively verify the presence of the carboxylic end-groups of AuNP surface adsorbed MHA molecules.

Immobilization of DNA:

The antisense survivin oligonucleotide sequence was chosen for this experiment (SEQ ID NO: 8,5'-CCCAGCCTTCCAGCTCCTTG-3'). The sequence was synthesized using standard solid phase phosphoramidite chemistry, and capped with a 5' amine group for EDC/NHS coupling to the carboxylic acid moiety of MHA. A 3' fluorophore label (fluroescein) was used in order to easily quantify conjugate AuNP loading of oligonucleotides and to serve as visual labels for cell culture experiments. Modified antisense oligonucleotides were purified using high performance liquid chromatography. Coupling of antisense survivin DNA to the surface of mixed-monolayer AuNPs was determined using a fluorescent plate reader to measure the concentration of fluorescently labeled DNA on the AuNPs. Using a standard dilution series of the labeled oligonucleotide, the approximate number of DNA strands per particle was determined.

Nanoparticle Uptake in Cancer Cells:

Mixed-monolayer structures were added to human prostate cancer cells (LnCaP) grown in culture, and imaged using confocal fluorescence microscopy. LnCaP cells were grown in monolayer cell culture to 60-80% confluence in glass bottom live-cell imaging dishes. Mixed-monolayer DNA-functionalized AuNPs were transfected at a concentration of 100 pM (12 hours) and compared to a control group of cells incubated with phosphate buffered saline (PBS). After incubation, the cell monolayers were washed with PBS (three times), and Leibovitz's media was added for confocal microscopy imaging of live cells.

Results

Nanoparticle Characterization:

Dynamic light scattering was used to measure the size of the nanoparticles before and after surface modification (Table 3). Unmodified AuNPs have a hydrodynamic radius of 9±1 nm. Upon addition of phospholipids and MHA, the diameter of the nanoparticle increases significantly, and supports the presence of the mixed lipid monolayer on the surface of the particles. Overall, the hydrodynamic diameter of the C15 lipid is greater than the C10 lipid, which agrees with the alkyl tail length differences of C15 versus C10 lipids.

TABLE 3

| Nanoparticle Conjugate | Lipid:MHA Ratio | Hydrodynamic Diameter (nm) |
|---|---|---|
| 10 nm AuNPs | | 9 ± 1 |
| C10 Conjugate | 10:1 | 12 ± 1 |
| | 20:1 | 12 ± 1 |
| | 50:1 | 12 ± 1 |

TABLE 3-continued

| Nanoparticle Conjugate | Lipid:MHA Ratio | Hydrodynamic Diameter (nm) |
|---|---|---|
| C15 Conjugate | 10:1 | 13 ± 1 |
|  | 20:1 | 14 ± 1 |
|  | 50:1 | 13 ± 1 |

Figure 16A:
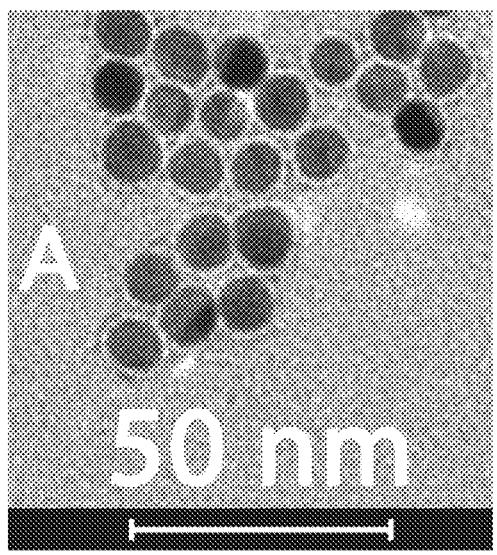
FIGS. 16A and 16B are transmission electron microscope images of mixed-monolayer functionalized nanoparticles according to one set of embodiments.
Figure 16B:
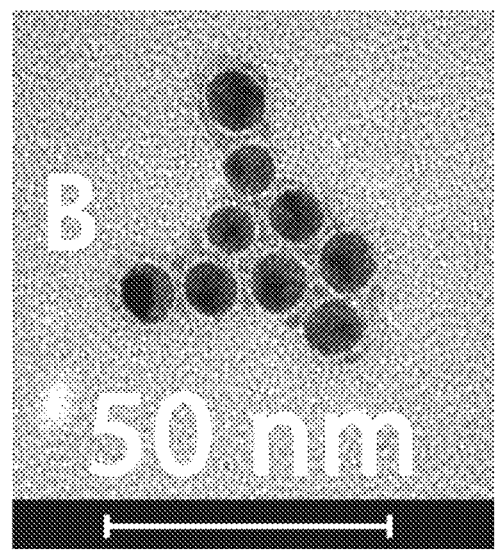

FIGS. 16A and 16B are TEM images of the C10 and C15 lipid mixed monolayer structures, each with a 10:1 ratio of phospholipid to MHA. Following negative staining with uranyl acetate, a halo-like ring is evident around each structure supporting the presence of the mixed-monolayer on the surface of the nanostructure core.

The presence of the carboxylic group was confirmed qualitatively via the addition of sodium bicarbonate and the evolution of gas (carbon dioxide) bubbles. The reaction for this experiment is: $R-COOH+NaHCO_3 \rightarrow R-COO^-Na^+ + H_2O$ (l)$+CO_2$ (g).

Immobilization of DNA:

Fluorescence measurements demonstrate the capability of mixed-monolayer phospholipid-functionalized AuNPs to bind DNA. A standard curve of free fluorescently labeled oligonucleotides was employed to determine the concentration and number of DNA sequences bound to the mixed-monolayer nanoparticles (Table 4). In general, the results show an increase in the number of oligonucleotides bound to the AuNP surface as the ratio of phospholipids to MHA increases. Optimal binding of oligonucleotides to the mixed monolayer AuNPs was observed for the C10 versus C15 phospholipid.

TABLE 4

| Nanoparticle Conjugate | Lipid:MHA Ratio | Fluorescence | DNA per Nanoparticle |
|---|---|---|---|
| C10 Conjugate | 10:1 | 2295 | 1 |
|  | 20:1 | 11822 | 13 |
|  | 50:1 | 15040 | 7 |
| C15 Conjugate | 10:1 | 8961 | 5 |
|  | 20:1 | 9243 | 9 |
|  | 50:1 | 6357 | 3 |

Figure 17:
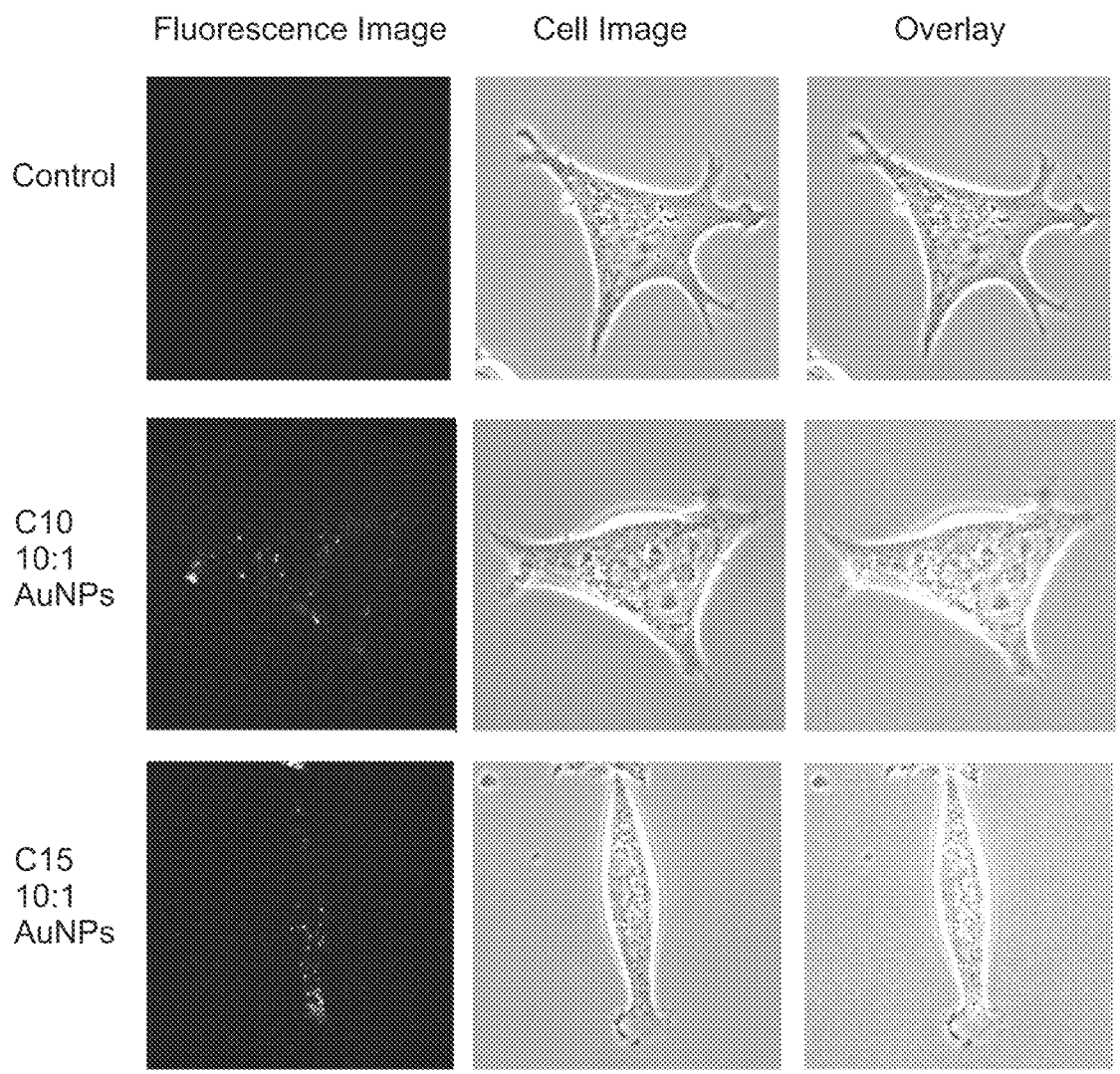
FIG. 17 shows LnCaP prostate cancer cells transected with mixed monolayer functionalized nanoparticles according to one set of embodiments.

Nanoparticle Uptake in Cancer Cells:

LnCaP prostate cancer cells were transfected with the mixed-monolayer DNA-functionalized AuNPs and imaged using confocal microscopy (FIG. 17). Cells were transfected with AuNPs functionalized with the mixed monolayer of C10 lipids and MHA or C15 lipids and MHA in a 10:1 ratio. In each case, the mixed-monolayer AuNPs were surface functionalized with fluorescein-labeled DNA. The images in FIG. 17 demonstrate the lack of fluorescence in the control group of cells—the anticipated result. Co-localization of nanoparticle fluorescent signal and LnCaP cells in phase implies that both conjugates effectively interact with LnCaP cells. The sub-cellular localization of the mixed-monolayer nanoparticles cannot be verified from these images.

Results demonstrate that AuNPs can be fabricated with a mixed monolayer of thiol-modified phospholipids and MHA. By using MHA as a surface component of the AuNPs, covalent coupling of amine-terminated DNA oligonucleotides can be achieved using well-established EDC/NHS coupling chemistry. The mixed-monolayer nanoparticles containing C10 lipids provided a suitable chemical background for the covalent attachment of amine-terminated oligonucleotides to co-adsorbed MHA molecules. Presumably, in some embodiments, the longer alkyl tail length of the C15 versus C10 lipid may cause increased steric hindrance to productive MHA coupling to incoming amine-terminated DNA sequences.

In order to determine the feasibility of using DNA-functionalized mixed-monolayer AuNPs as therapeutic agents, their ability to be taken up into prostate cancer cells grown in culture was assessed. Initial cell uptake experiments imply that the nanoparticle conjugates interact favorably with cancer cells. Future studies will focus on the interaction of the mixed monolayer AuNP DNA conjugates with cancer cells and more thoroughly assess their sub-cellular distribution and biological function.

The results of this experiment demonstrate a successful approach of surface functionalizing AuNPs with both lipids and DNA in order to potentially realize the benefits of both of these biological molecules in the context of cellular transfection and gene regulation.

These results also open up the possibility for future work involving other applications with proteins or other biologically important molecules coupled to the surface of the mixed-monolayer AuNPs using facile EDC/NHS coupling chemistry.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A structure comprising:
a synthetic nanostructure having a nanostructure core, wherein the core comprises an inorganic material;
a shell comprising a lipid surrounding and attached to the nanostructure core; and
an oligonucleotide adapted to regulate gene expression associated with at least one lipid of an outer surface of the shell, wherein the oligonucleotide is non-covalently associated with the lipid of the outer surface of the shell,
wherein the structure is adapted to sequester cholesterol.

2. A structure comprising:
a synthetic nanostructure having a nanostructure core, wherein the core comprises an inorganic material;
a hydrophobic shell surrounding the nanostructure core; and
an oligonucleotide adapted to regulate gene expression associated with at least one lipid of an outer surface of the shell, wherein the oligonucleotide is non-covalently associated with the lipid of the outer surface of the shell,
wherein the structure is adapted to sequester cholesterol.

3. A structure comprising:
a synthetic nanostructure comprising a nanostructure core, wherein the core comprises an inorganic material; and
a cholesterol-modified oligonucleotide non-covalently associated with the nanostructure core.

4. A nanostructure comprising an oligonucleotide adapted to regulate gene expression and a synthetic carrier comprising a core surrounded by apolipoprotein A1,
wherein the core comprises an inorganic material,
wherein the oligonucleotide adapted to regulate gene expression is non-covalently associated with the apolipoprotein A1.

5. A pharmaceutical composition, comprising:
the structure of claim 2 and
one or more pharmaceutically acceptable carriers, additives, and/or diluents.

6. A kit for diagnosing, preventing, treating or managing a disease or bodily condition comprising:
a composition comprising a plurality of structures as in claim 2; and
instructions for use of the composition for diagnosing, preventing, treating or managing a disease or bodily condition.

7. The structure of claim 2, wherein the structure has a binding constant to cholesterol, $K_d$, of less than or equal to about 10 mM.

8. The structure of claim 2, wherein the shell comprises an outer surface phospholipid, wherein the oligonucleotide is non-covalently associated with the outer surface phospholipid.

9. The structure of claim 2, wherein the shell comprises a lipid bilayer, wherein the oligonucleotide is associated with an outer surface lipid of the lipid bilayer.

10. The structure of claim 9, wherein the lipid bilayer comprises 50-200 phospholipids.

11. The structure of claim 8, wherein the phospholipid comprises:

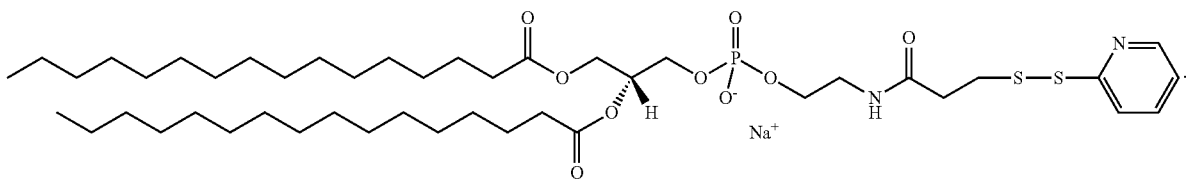 [SMILES: CCCCCCCCCCCCCCCC(=O)OC[C@H](COP(=O)([O-])OCCNC(=O)CCSSc1ccccn1)OC(=O)CCCCCCCCCCCCCCC ; [Na+]]

12. The structure of claim 8, wherein the phospholipid comprises:

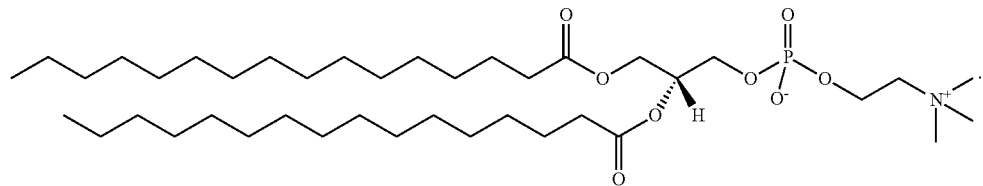 [SMILES: CCCCCCCCCCCCCCCC(=O)OC[C@H](COP(=O)([O-])OCC[N+](C)(C)C)OC(=O)CCCCCCCCCCCCCCC]

13. The structure of claim 9, wherein at least a portion of the lipid bilayer is physisorbed to the core.

14. The structure of claim 2, wherein the nanostructure core comprises a metal, or is substantially formed from a metal.

15. The kit of claim 6, wherein the disease or bodily condition is associated with a cancer.

16. The kit of claim 6, wherein the disease or bodily condition is associated with prostate cancer.

17. The structure of claim 2, wherein the oligonucleotide is physisorbed onto a portion of the shell.

18. The structure of claim 2, wherein the oligonucleotide is adapted and arranged to modulate expression of a target by at least about 50%, at least about 60%, at least about 70%, at least about 80%, or at least about 90% when contacted with a biological sample or patient under physiological conditions and at a concentration where a nonsense or sense control has little or no effect.

* * * * *

SEQUENCE LISTING

```
<160> NUMBER OF SEQ ID NOS: 8

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cholesteryl-TEG

<400> SEQUENCE: 1
aaaaaaaaaa tcagccgctg tcacacgcac ag                                    32

<210> SEQ ID NO 2
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cholesteryl-TEG
<220> FEATURE:
<221> NAME/KEY: misc_feature
<222> LOCATION: (19)..(19)
<223> OTHER INFORMATION: Fluorescent Label

<400> SEQUENCE: 2
aaaaaaaaaa tcagccgctg tcacacgcac ag                                    32

<210> SEQ ID NO 3
```

```
<211> LENGTH: 33
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cholesteryl-TEG

<400> SEQUENCE: 3
aaaaaaaaaa ccccgtaatc ttcataatcc gag                                33

<210> SEQ ID NO 4
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: Cholesteryl-TEG
<220> FEATURE:
<221> NAME/KEY: misc_feature
<222> LOCATION: (20)..(20)
<223> OTHER INFORMATION: Fluorescent label

<400> SEQUENCE: 4
aaaaaaaaaa gccttacgct acccggagac ca                                 32

<210> SEQ ID NO 5
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (32)..(32)
<223> OTHER INFORMATION: -SH

<400> SEQUENCE: 5
tcagccgctg tgacacgcac agaaaaaaaa aa                                 32

<210> SEQ ID NO 6
<211> LENGTH: 33
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (33)..(33)
<223> OTHER INFORMATION: -SH

<400> SEQUENCE: 6
ccccgtaatc ttcataatcc gagaaaaaaa aaa                                33

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: NH2
<220> FEATURE:
<221> NAME/KEY: misc_feature
```

```
<222> LOCATION: (20)..(20)
<223> OTHER INFORMATION: Fluorescent label

<400> SEQUENCE: 7
cccagccttc cagctccttg                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
cccagccttc cagctccttg                                              20
```